US007994146B2

(12) United States Patent
Jefferies et al.

(10) Patent No.: US 7,994,146 B2
(45) Date of Patent: Aug. 9, 2011

(54) METHOD OF ENHANCING AN IMMUNE RESPONSE

(75) Inventors: Wilfred Arthur Jefferies, Surrey (CA); Qian-Jin Zhang, Richmond (CA); Susan Shu-Ping Chen, Vancouver (CA); Judie Barbara Alimonti, Winnipeg (CA)

(73) Assignee: Tapimmune, Inc., Seattle, WA (US)

( * ) Notice: Subject to any disclaimer, the term of this patent is extended or adjusted under 35 U.S.C. 154(b) by 720 days.

(21) Appl. No.: 12/029,080

(22) Filed: Feb. 11, 2008

(65) Prior Publication Data

US 2010/0080776 A1    Apr. 1, 2010

Related U.S. Application Data

(63) Continuation of application No. 10/046,542, filed on Jan. 16, 2002, now Pat. No. 7,378,087, which is a continuation-in-part of application No. 08/817,731, filed as application No. PCT/CA95/00544 on Sep. 22, 1995, now Pat. No. 6,361,770, which is a continuation-in-part of application No. 08/311,442, filed on Sep. 23, 1994, now abandoned.

(51) Int. Cl.
*A61K 48/00* (2006.01)
*A61K 39/12* (2006.01)

(52) U.S. Cl. .................................... 514/44 R; 424/199.1
(58) Field of Classification Search ................ 514/44 R; 424/199.1
See application file for complete search history.

(56) References Cited

U.S. PATENT DOCUMENTS 6,361,770 B1    3/2002  Jefferies et al.

OTHER PUBLICATIONS

Spies et al., (1991) Nature, vol. 351, 323-324.*
Momberg et al. (1992) Nature, vol. 360, 174-177.*
Powis et al., (1991), Nature, vol. 354, 528-531.*
Verma et al. (1997) Nature, vol. 389, 239-242.*
Miller et al. (1995) FASEB, vol. 9, 190-199.*
Monaco, J.J., Immunology Today, Vo. 13, No. 5, May 1992, pp. 173-179.
Ossevoort, M.A. et al., European Journal of Immunology, vol. 23, No. 12, 1993, pp. 3082, 3088.
Zweerink, H.J., et al., Journal of Immunology, vol. 150, No. 5, Mar. 1, 1993, pp. 1763-1771.
Arnold, D. et al., Nature, vol. 360, No. 6400, Nov. 12, 1992, pp. 171-174.
Momburg, F. et al., Nature, vol. 360, No. 6400, Nov. 12, 1992, pp. 174-177.
Kelly, A. et al., Nature, vol. 355, No. 6361, Feb. 13, 1992, pp. 641-644.
Spies, T. et al., Nature, vol. 355, No. 6361, Feb. 13, 1992, pp. 644-646.
Fruh, K. et al., Journal of Biological Chemistry, vol. 267, No. 31, Nov. 5, 1992, pp. 22131-22140.
Yang, Y. et al., Journal of Biological Chemistry, vol. 267, No. 17, Jun. 15, 1992, pp. 11669-11672.
Jefferies, W.A. et al., The Journal of Immunology, vol. 151, No. 6, Sep. 15, 1993, pp. 2974-2985.
Verma, et al. (1997) Nature, vol. 389, 239-242, 1997.
Miller, et al. (1995) FASEB, vol. 9, 190-199, 1995.
Spies, et al., (1991) Nature, vol. 351, 323-324, May 1991.
Franksson, et al. (1993) J. Exp. Med., vol. 177, 201-205, Jan. 1993.
Powis, et al., (1991) Nature, vol. 354, 528-531, Dec. 1991.
Bachmann, et al. (1994) Current Opin. Immunol., vol. 6, 320-327, 1994.
Restifo, et al. (1993) J. of Experimental Medicine, vol. 177, 265-272, Feb. 1993.
Orkin et al. (1995) "Report and Recommendations to the Panel to Assess the NIH Investment in Research on Gene Therapy," Dec. 1995.
Gabathuler, R. et al., The Journal of Experimental Medicine, vol. 180, No. 4, Oct. 1, 1994, pp. 1415-1425.

* cited by examiner

*Primary Examiner* — Anne Marie S Wehbe
(74) *Attorney, Agent, or Firm* — Rissman Hendricks & Oliverio LLP

(57)  ABSTRACT

A method of enhancing an immune response to an antigen is provided. The method involves augmenting the level of a TAP molecule in a target cell bearing the antigen. Preferably, the TAP molecules enhanced by administering a nucleic acid sequence encoding a TAP-1 and/or TAP-2 molecule. The method is useful in treating infectious diseases and cancer.

10 Claims, 45 Drawing Sheets

| | VV-NP | VV-NP + VV - hTAP12 |
|---|---|---|
| VSV pCTL | 1/78,000 | 1/16,000 |

I - CMT.neo

II - CMT.1-10

III - CMT.2-10

IV - CMT.21-21

| TUMOR | ONE MONTH | | TWO MONTHS | | RATIO[b] | |
|---|---|---|---|---|---|---|
| | CD4% | CD8% | CD4% | CD8% | CD4 | CD8 |
| CMTneo | 0.54 | 0.41 | | | | |
| CMT 1-1 | 1.02 | 0.87 | | | 1.9 | 2.1 |
| CMT 1-4 | | | 1.07 | 1.2 | 2.0 | 2.9 |
| CMT 1-10 | 4.19 | 2.94 | | | 7.8 | 7.2 |
| CMT 2-1 | 0.24 | 0.23 | | | 0.4 | 0.6 |
| CMT 2-10 | 0.12 | 0.66 | | | 0.2 | 1.6 |

METHOD OF ENHANCING AN IMMUNE RESPONSE

This application is a continuation of U.S. patent application Ser. No. 10/046,542 filed Jan. 16, 2002 (now allowed) which is a continuation-in-part application of U.S. patent application Ser. No. 08/817,731 filed Jul. 21, 1997 (now allowed), which is a national phase entry application of PCT/CA95/00544 filed Sep. 22, 1995, which claims priority from U.S. patent application Ser. No. 08/311,442 filed Sep. 23, 1994, now abandoned.

FIELD OF THE INVENTION

The invention relates generally to a method of enhancing an immune response to an antigen by augmenting the level of a TAP molecule in a target cell bearing the antigen.

BACKGROUND OF THE INVENTION

The cytotoxic T lymphocyte (CTL) response is a major component of the immune system, active in immune surveillance and destruction of infected or malignant cells and invading organisms expressing foreign antigens on their surface. The ligand of the antigen specific T cell receptor is a complex made up of a peptide fragment of an antigen bound to major histocompatibility complex (MHC) molecules. In particular, cytotoxic T lymphocytes recognise peptide bound to MHC Class I molecules.

MHC class I molecules are normally expressed at the cell surface as ternary complexes formed by a heavy chain of 46 kD, a light chain called β2-microglobulin ($\beta_2$M) of 12 Kd and a peptide composed of 8-10 amino-acids Ivan Bleek, G. M. and S. G. Nathenson, *Nature* 348:213, 1990; Zhang, W. et al., *Proc. Natl. Acad. Sci. USA* 89:8403, 1992; Matsumura, M. et al., *Science* 257:927, 1992; and Latron. F., et al., *Science* 257:964, 1992). Formation of the ternary complex is thought to involve transport into the lumen of the endoplasmic reticulum (ER) of peptides generated by protein degradation in the cytoplasm (Nuchtern. J. G. et al., *Nature* 339:223, 1989; Yewdell, J. W. and J. R. Bennink, *Science* 244:1072, 1989; and Cox. J. H. et al., *Science* 247:715, 1990). The study of mutant cell lines selected for their low expression of MHC class I molecules at the cell surface has provided insights into the molecular events required for antigen processing. These studies have allowed the identification of two genes located in the MHC region which encode proteins of the ATP binding cassette (ABC) family. These genes, called TAP-1 and TAP-2, have been implicated in transport of peptides from the cytoplasm to the lumen of the ER (Deverson, E. V. et a). *Nature* 348:738, 1990; Trowsdale, J. et al., *Nature* 348:741, 1990; Spies, T. et al., *Nature* 348:744, 1990; Monaco, J. J. et al., *Science* 250:1723, 1990; Spies, T. and R. DeMars, *Nature* 351:323, 1991; Bahram, S. et al., *Proc. Natl. Acad. Sci. USA* 88:10094, 1991; Spies, T. et al., *Nature* 355:644, 1992; Kelly, A. et al., *Nature* 355:641, 1992; Powis, S. H. et al., *Proc. Natl. Acad. Sci. USA* 89:1463, 1992; and Colonna. M. et al., *Proc. Natl. Acad. Sci. USA* 89:3932, 1992). Two other MHC linked genes. LMP-2 and -7 (Monaco, J. J. and McDevitt, 1982, *Proc. Natl. Acad. Sci. USA* 79:3001), are components of the proteasome, a cytoplasmic multicatalytic protease complex, which is likely responsible for some aspects of protein degradation for antigen processing (Ortiz-Navarette, V. et al., *Nature* 353:662, 1991; Brown, M. G. et al., *Nature* 353:355, 1991; Glynne, R. et al., *Nature* 353:357, 1991; Martinez, C. K. and J. J. Monaco, *Nature* 353:664, 1991; Kelly, A. et al., *Nature* 353:667, 1991; Yang, Y., et al., *Proc. Natl. Acad. Sci. USA* 89:4928, 1992; Goldberg, A. L. and K. L. Rock, Nature 357:3751 1992).

The mouse mutant lymphoma cell line RMA-S expresses low levels of class I molecules at the cell surface compared to the wild type RMA cells (Ljunggren, H.-G. et al., *J. Immunol.* 142:2911, 1989; and Townsend. A et al., *Nature* 340:443, 1989). Influenza virus infected RMA-S cells present influenza peptides in the context of $D^b$ molecules inefficiently and are only weakly recognized by specific CTL (Townsend, A et al., *Nature* 340:443, 1989). Transfection with the putative transporter gene, TAP-2, complements this deficiency (Powis. S. J. et al., *Nature* 354:528, 1991; and Attaya. M. et al., *Nature* 355:647, 1992). The endogenous TAP-2 gene of RMA-S cells was shown to contain a point mutation which introduces a stop translation codon resulting in an incomplete and defective TAP-2 protein (Yang. Y. et al., *J. Biol. Chem.* 267:11669, 1992). Despite the defective TAP-2 protein in RMA-S cells, antigenic peptides from vesicular stomatitis virus (VSV) bypass the defect and are presented to specific CTL by $K^b$ molecules in RMA-S cells (Esquivel. F., et al., *J. Exp. Ned.* 175:163, 1992; and Hosken. N. A. and M. J. Bevan, *J. Exp. Med.* 175:719, 1992). The VSV-nucleocapsid (N) peptide, VSV-N 52-59, has been shown to be the major peptide presented by $K^b$ molecules on VSV infected cells (van Bleek, G. M. and S. G. Nathenson, *Nature* 348:213, 1990). The presence of the wild-type TAP-1 protein in RMA-S cells may be sufficient for translocation of the VSV-N 52-59 peptide to the ER lumen (Powis. S. J. et al., *Nature* 354:528, 1991; Attaya, M. et al., *Nature* 355:647, 1992; and Yang. Y. et al., *J. Biol. Chem.* 267:11669, 1992). Alternatively, the VSV-N 52-59 peptide may not need a functional transporter for transport into the lumen of the ER. Expression of minigene-encoded viral peptide epitopes in T2 cells (Zweerink. H. J. et al., *J. Immunol.* 150:1763, 1993) and in-vitro translation and translocation using microsomes from T2 cells (Lévy, F. et al., *Cell* 67:265, 1991) support this contention.

A separate class of antigen processing variants are those in which the assembly and the surface expression of MHC class I molecules are entirely inducible by IFN-γ (Klar, D. and G. J. Hc1 immering, EMBO J. 8:475, 1989). For example in the small lung carcinoma cell line. CMT.64, recognition by influenza virus specific CTL does not take place unless induced with IFN-γ (Sibille, C. et al., *Eur. J. Immunol.* 22:433, 1992). The very low amount of all proteasome components present in uninduced CMT.64 cells is presumed to be responsible for their phenotype (Ortiz-Navarette. V et al., *Nature* 353:662, 1991). Exogenous influenza peptides can bind to $D^b$ molecules on CMT.64 cells and complement recognition by influenza specific CTL (Sibille, C. et al., *Eur. J. Immunol.* 22:433, 1992). In addition, it has been found that the $\beta_2$m and the VSV-N 52-59 peptides added exogenously to these cells complement recognition by VSV specific CTL restricted to $K^b$ (Jefferies W. A et al., 1993, *J. Immunol.* 151:2974). The amount of β2m and of heavy chains synthesized in these cells may limit the amount of MHC class I expression on the cell surface (Jefferies et al, supra, 1993). A dysfunction of the putative peptide transporters and/or in the generation of the peptide may be responsible for the CMT.64 phenotype which may represent a mechanism to downregulate MHC class I expression, a feature common to many carcinomas.

Restifo, N. R. et al. (*J. Exp. Ned.* 177:265-272, 1993) studied the antigen processing efficiency of 26 different human tumor lines using a recombinant vaccinia virus (VV) to transiently express the $K^d$ molecule. Three cell lines, all human small cell lung carcinoma, consistently failed to process endogenously synthesized proteins for presentation to $K^d$-restricted, Vac-specific T cells. Pulse-chase experiments showed that MHC class I molecules were not transported by the cell lines from the endoplasmic reticulum (ER) to the cell surface. Northern blot analysis of the cells revealed low to nondetectable levels of mRNAs for MHC-encoded proteasome components LMP7 and LMP-2 as well as the putative peptide transporters TAP-1 and TAP-2.

There is a need in the art for methods to augment or enhance an immune response to various targets including virally infected and malignant cells.

SUMMARY OF THE INVENTION

The present inventors have shown that augmenting either TAP-1 or TAP-2 expression on either virally infected or tumor target cells enhances the immunogenicity of the target cells as demonstrated by an enhanced cytotoxic T lymphocyte response.

Accordingly, the present invention provides a method of enhancing an immune response to antigen by administering an effective amount of an agent that can augment the level of a TAP molecule in a target cell bearing the antigen to a cell or animal in need thereof.

In one embodiment, the level of the TAP molecule is augmenting by administering a nucleic acid sequence encoding the TAP molecule to a target cell bearing the antigen.

The target cell can be any cell to which one wishes to generate an immune response such as a virally infected cell or a cancer cell. The target cell can also be normal or non-infected cell, for example when the method is used as a vaccine or in a prophylactic protocol to generate an immune response to a particular antigen.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. Therapeutic Methods

Figure 1A:
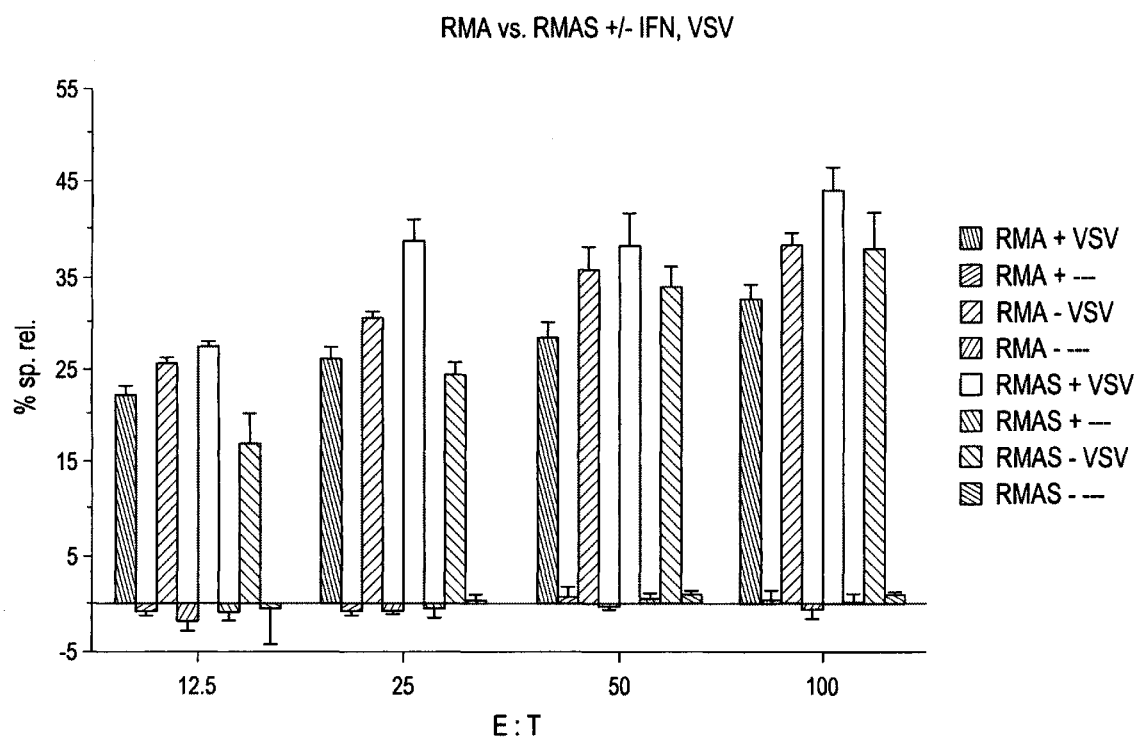
FIG. 1A depicts histograms showing CTL recognition of VSV infected RMA and RMA-S IFN-γ induced (+)

The present inventors have surprisingly shown that TAP-1 alone (in the absence of TAP-2) or TAP-2 alone (in the absence of TAP-1) is sufficient to enhance processing and presentation of VSV peptides to the intracellular site of MHC assembly, permitting stable MHC class I molecule endogenous peptide complexes to be formed, transported and expressed at the cell surface. They also demonstrated that TAP-2 alone in the absence of TAP-1, is sufficient to enhance processing and presentation of the influenza NP366-374 peptide. The inventors have also shown that TAP-1 and/or TAP-2 can enhance the immunogenicity of tumor cells.

In summary, the inventors have shown that the TAP molecules act as an adjuvant that can increase the immunogenicity of targets bearing an antigen. Importantly, the inventors have shown that when TAP is included in a viral vaccine over 10,000 fold less virus can be used to elicit an equivalent immune response that is observed in the absence of TAP. This has important implications as it can allow the use of lower doses of antigen. Using a lower dose of a vaccine increases the safety and reduces the cost per patient.

Accordingly, the present invention provides a method of enhancing an immune response to antigen comprising administering, to a cell or animal in need thereof, an effective amount of an agent that can augment the level of a TAP molecule in a target cell bearing the antigen.

The term "enhancing an immune response" means that the method of the invention evokes and/or enhances any response of the animal's immune system, including of either a cell-mediated (i.e. cytotoxic T lymphocyte mediated) or humoral (i.e. antibody mediated) response. These immune responses can be assessed by number of in vitro or in vivo assays well known to those skilled in the art including, but not limited to, cytotoxic T lymphocyte assays, productions of cytokines, regression of tumors, survival of tumor bearing animals, and antibody assays.

The term "TAP molecule" as used herein includes the TAP-1 molecule alone, the TAP-2 molecule alone as well as combinations of both TAP-1 and TAP-2. Augmenting either or both of these molecules may be useful in the method of the invention. One of skill in the art can readily determine whether or not one or both need to be augmented in order to increase the immunogenicity of a particular antigen.

The term "an agent that can augment the level of a TAP molecule" means any agent that can increase the level or activity of a TAP-1 and/or TAP-2 molecule as compared to the level or activity in same target cell in the absence of the agent. The levels of the TAP-1 and/or TAP-2 molecules in the target cell can be readily determined by one of skill in the art using known methods including Western blotting, SDS-PAGE, immunocytochemistry, RT PCR, Northern blotting, and in situ hybridization.

The levels of the TAP molecule may be augmented using agents that can increase TAP expression including interferon-γ and p53. The levels of the TAP molecule may also be augmented by administering a nucleic acid molecule encoding the TAP molecule.

The term "effective amount" as used herein means an amount effective, at dosages and for periods of time necessary to achieve the desired result. The effective amount of a compound of the invention may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation.

The antigen can be any antigen to which one wishes to generate an immune response including, but not limited to, antigens associated with infectious diseases (e.g. viral antigens, bacterial antigens, parasitic antigens), self antigens (e.g. antigens implicated in autoimmune diseases) and tumor antigens. The term "tumor antigens" used herein includes both tumor associated antigens and tumor specific antigens. The term "tumor associated antigens" means an antigen that is expressed on the surface of a tumor cell in higher amounts than is observed in normal cells or an antigen that is expressed in normal cells during fetal development. A "tumor specific antigen" is an antigen that is unique to tumor cells and is not expressed on normal cells.

Examples of viral antigens include vesicular stomatitis virus (VSV) antigens, influenza antigens. Sendai virus antigens. HIV antigens (e.g. Gag, POL), CMV antigens, Hepatitis B and C antigens, Human Papilloma Virus (HPV) E6 and E7 antigens.

Examples of tumor antigens include carcinoembryonic antigens (CEA), carcinoma associated mutated mucins, for example. MUC-1 gene products, gp100, MART-1/Melan A. gp75 (TRP-1) antigens of MAGE family, for example.

MAGE-1, 2, 3, 4, 6, and 12, antigens of BAGE family, antigens of GAGE family, for example. GAGE-1,2, antigens of RAGE family, for example, RAGE-1. N-acetylglucosaminyl-transferase-V, p15; tumor specific mutated antigens; mutated β-catenin, mutated MUM-1 and mutated cyclin dependent kinases-4 (CDK4), mutated oncogene products: p21 ras. BCR-abl, p53 and p185 HER2/neu, mutated epidermal growth factor receptor (EGFR) EBNA gene products of EBV, for example, EBNA-1 gene product E7. E6 proteins of human papillomavirus, prostate specific antigens (PSA) prostate specific membrane antigen (PSMA). PCTA-1, idiotypic epitopes or antigens, for example, immunoglobulin idiotypes or T cell receptor idiotypes.

The target cell can be any cell to which one wishes to generate an immune response. When the method of the invention is used in a prophylactic therapy or a vaccine the target all is essentially a normal cell (expressing normal TAP levels) that may not have been otherwise exposed to the antigen. In such a case, the agent that augments TAP is co-administered with the antigen to which one wishes to generate an immune response. When the method of the invention is used as a therapeutic, the target cell may be previously infected with a pathogen (such as a virus or bacteria) or may be a cell that is malignant or cancerous.

As hereinbefore mentioned, in a preferred embodiment, the method of the invention involves administering a nucleic acid molecule encoding a TAP molecule in order to augment the level of TAP expression in the target cell.

Accordingly, in one embodiment, the present invention provides a method of enhancing an immune response to an antigen comprising administering an effective amount of a nucleic acid molecule comprising a sequence encoding a TAP molecule to an animal or cell in need thereof.

The term "animal" as used herein includes all members of the animal kingdom, including humans. Preferably, the animal to be treated is a human.

The nucleic acid molecule encoding the TAP molecule can be administered to the animal in vivo where the TAP molecule will be expressed in vivo. When administered in vivo, the TAP molecule can be administered by any route including, but not limited to, intraperitoneally, intravenously, intratumorally, subcutaneously, orally, mucosally, intradermally or submucosally. As an alternative, the TAP molecule can be administered to the target cells ex vivo where the TAP molecule will be expressed in the cells in vitro and then the target cells expressing TAP can be administered to the animal.

The nucleic acid molecule comprising a sequence encoding TAP-1 and/or TAP-2 under control of a suitable promoter may be readily synthesized using techniques known in the art. A sequence encoding TAP-1 includes a sequence encoding a protein having the amino acid sequence as set out in Trowsdale. J. et al., *Nature* 348:741, 1990 and international Application No. PCT/US91/06105 published on Mar. 19, 1992. A nucleic acid molecule comprising a sequence encoding TAP-1 may be isolated and sequenced, for example, by synthesizing cDNAs from RNA—and using rapid amplification of cDNA ends (RACE. Frohman, et al., 1986) using oligonucleotides specific for TAP-1, and analysing the sequences of the clones obtained following amplification. Oligonucleotides specific for TAP-1 may be identified by comparing the nucleic acid sequence of the nucleic acid molecules of the invention to known sequences of TAP-1. Nucleic acid molecules used in the method of the invention encoding TAP-1 or TAP-2 may also be constructed by chemical synthesis and enzymatic ligation reactions using procedures known in the art. The sequence encoding TAP-1 or TAP-2 may also be prepared using recombinant DNA methods.

The method of the invention not only contemplates the use of the known TAP-1 and TAP-2 sequences but also includes the use of: sequences that have substantial sequence homology to the known TAP sequences, sequences that hybridize to the known TAP sequences as well as all analogs or modified forms of the known TAP sequences.

The term "sequence that has substantial sequence homology" means those nucleic acid sequences which have slight or inconsequential sequence variations from the known TAP sequences i.e., the sequences function in substantially the same manner and can be used to augment an immune response. The variations may be attributable to local mutations or structural modifications. Nucleic acid sequences having substantial homology include nucleic acid sequences having at least 65%, more preferably at least 85%, and most preferably 90-95% identity with the known nucleic acid sequences of TAP.

The term "sequence that hybridizes" means a nucleic acid sequence that can hybridize to a TAP sequence under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. For example, the following may be employed: 6.0× sodium chloride/sodium citrate (SSC) at about 45° C., followed by a wash of 2.0×SSC at 50° C.; 0.2×SSC at 50° C. to 65° C.; or 2.0×SSC at 44° C. to 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

The term "a nucleic acid sequence which is an analog" means a nucleic acid sequence which has been modified as compared to the known sequence of a TAP molecule wherein the modification does not alter the utility of the sequence as described herein. The modified sequence or analog may have improved properties over the known sequence. One example of a modification to prepare an analog is to replace one of the naturally occurring bases (i.e. adenine, guanine, cytosine or thymidine) of the known sequence with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-azo thymine, pseudo uracil, 4-thiouracil, 8-halo adenine, 8-aminoadenine, 8-thiol adenine, 8-thioalkyl adenines, 8-hydroxyl adenine and other 8-substituted adenines, 8-halo guanines, 8 amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

Some of the methods contemplated herein use nucleic acid molecules containing sequences encoding truncated non functional forms of TAP-1 or TAP-2. Truncated non functional forms of TAP-1 and TAP-2 may be identified by deleting portions of the TAP-1 or TAP-2 gene to produce fragments. Such fragments should hybridize to the TAP-1 or TAP-2 sequences under stringent hybridization conditions. Stringent hybridization conditions are those which are stringent enough to provide specificity, reduce the number of mismatches and yet are sufficiently flexible to allow formation of stable hybrids at an acceptable rate. Such conditions are known to those skilled in the art and are described, for example, in Sambrook, et al, (1989, molecular Cloning, A Laboratory Manual, Cold Spring Harbor). The ability of the truncated forms of TAP-1 and TAP-2 to transport endogenous peptides may be determined using the methods described herein.

Nucleic acid molecules having a sequence which codes for TAP-1 or TAP-2, including the homologs and modified forms discussed above, may be incorporated in a known manner into an appropriate expression vector which ensures good expression of the protein or part thereof. Possible expression vectors include but are not limited to cosmids, plasmids (including both naked DNA plasmids and liposome encapsulated plasmids), or modified viruses, so long as the vector is compatible with the target cell used.

It is contemplated that the nucleic acid molecules described herein contain the necessary elements for the transcription and translation of the inserted sequence. Suitable transcription and translation elements may be derived from a variety of sources, including bacterial, fungal, viral, mammalian, or insect genes. Selection of appropriate transcription and translation elements is dependent on the target cell chosen as discussed below, and may be readily accomplished by one of ordinary skill in the art. Examples of such elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, and sequences conferring inducibility of transcription may be incorporated into the expression vector. It will also be appreciated that the necessary transcriptional and translation elements may be supplied by the native TAP-1 gene, TAP-2 gene and/or their flanking regions.

The nucleic acid molecules may also contain a reporter gene which facilitates the selection of transformed or transfected host cells. Examples of reporter genes are genes encoding a protein such as β-galactosidase, chloramphenicol acetyltransferase, firefly luciferase, or an immunoglobulin or portion thereof such as the Fc portion of an immunoglobulin preferably IgG. In a preferred embodiment, the reporter gene is lac Z. Transcription of the reporter gene is monitored by changes in the concentration of the reporter protein such as β-galactosidase, chloramphenicol acetyltransferase, or firefly luciferase. This makes it possible to visualize and assay for expression of TAP-1.

Nucleic acid molecules comprising a sequence encoding TAP-1 or TAP-2 can be introduced into target cells via transformation, transfection, infection, electroporation etc. Methods for transforming transfecting, etc. host cells to express foreign DNA are well known in the art (see, e.g., Itakura et al., U.S. Pat. No. 4,704,362; Hinnen et al., PNAS USA 75:19291933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989, all of which are incorporated herein by reference).

Suitable expression vectors for directing expression in mammalian cells generally include a promoter, as well as other transcriptional and translational control sequences. Common promoters include SV40. MMTV, metallothionein-1, adenovirus Ela, CmV, immediate early, immunoglobulin heavy chain promoter and enhancer, and RSV-LTR. Protocols for the transfection of mammalian cells are well known to those of ordinary skill in the art.

In a preferred embodiment, the nucleic acid molecule is introduced into the target cell in a viral vector, preferably vaccinia viral vectors, andenovirus based vectors, lenti virus based vectors and herpes simplex virus based vectors. The vectors may be live, attenuated, replication conditional or replication deficient. Most preferably the viral vectors are attenuated. Suitable promoters for use with vaccinia viruses include P7.5 (Cochran, M. A. at al, 1985, *J. Virol.* 54:30), P11 (Bertholet, C. et al, 1985, *Proc. Natl. Acad. Sci. USA* 82:2096), CAE-1 (Patel, D. D. et al, 1988, *Proc. Natl. Acad. Sci. USA* 85:9431).

The nucleic acid molecule may be inserted into a non-essential site of a vaccinia viral vector. Such non-essential sites are well known and are described, for example, in Perkus et al, 1986. *Virology* 152:285; Hruby et al, 1983, *Proc. Nacl. Acad. Sci. USA* 80: 3411 and; Weir and Moss, 1983, *J. Virol.* 46:530). Recombinant viruses expressing TAP-1 may be readily identified using techniques known in the art and discussed, for example, in Moss, B, 1992, (*Curr. Topics Microbiol. Immunol.* 158:25).

In a preferred embodiment, the nucleic acid molecule comprising a sequence encoding a TAP molecule is co-administered with an additional nucleic acid molecule comprising a sequence encoding an antigenic peptide, such as a pathogenic peptide or tumor antigen. Examples of pathogenic peptides include viral peptides such as the ones hereinbefore mentioned. Administering the nucleic acid sequence encoding a TAP molecule with an antigenic peptide will increase the immune response to the antigen.

The nucleic acid sequence encoding a TAP molecule can also be administered in conjunction with other stimulatory molecules including growth factors, accessory molecules, anti-angiogenic therapies and chemokines. Examples of growth factors include interferon-γ, IL-1. IL-2, and GM-CSF. Examples of accessory molecules include 87 and ICAM as well as accessory molecules involved in antigen presentation such as tapasin, calnexin, calreticulin, p58. MHC class I heavy chain, $\beta_2$M, LMP2 and other interferon inducible genes. Examples of chemokines include molecules such as MCP1. These molecules will help stimulate the expansion of lymphocytes involved in the specific responses that were initiated by enhanced MHC class I restriction antigen process in that it occurs when TAP is expressed above normal levels. Other stimulatory molecules include genes that are inducible by retinoic acid, tumor necrosis factor, interferon alpha, beta or gamma, tapasin, calnexin, calreticulin, p53, p58, MHC I heavy chain. HSP 70, HSP 90, BIP, GRB94, interferon response proteins 3 and 7.

The additional molecules can either by administered in the form of a nucleic acid or as a protein. When administered as a nucleic acid, the stimulatory molecules may be administered as a chimeric nucleic acid construct that encodes the TAP molecule, the antigen as well as the stimulatory molecule. In addition, each of the molecules may be administered in different constructs and administered in different vectors.

The method of the present invention can be used as an adjunct to surgery, chemotherapy, radiation therapy, immunotherapy or photodynamic therapy as one of its uses is to treat cancer.

In one embodiment, the target cell is one that normally expresses low or non-detectable levels of MHC Class I molecules and low or non-detectable levels of TAP-1 and/or TAP-2 proteins. Such a phenotype is common in malignant cells.

Accordingly, the present invention provides a method of enhancing expression of MHC class I molecules bearing endogenous peptides on the surface of a target cell expressing low or nondetectable levels of MHC class I molecules and possibly expressing low or nondetectable levels of TAP-1 and TAP-2 transporter proteins comprising: introducing into the target cell a nucleic acid molecule comprising a sequence encoding TAP-1 or TAP-2 under control of a suitable promoter and; expressing TAP-1 or TAP-2 in the target cell under suitable conditions, thereby enhancing processing and presentation of MHC class I molecules bearing endogenous peptides.

Target cells expressing low or non-detectable levels of MHC Class I molecules and expressing low or nondetectable levels of TAP-1 and TAP-2 transporter proteins may be selected by methods known in the art. For example, a target cell may be infected with a recombinant viral vector such as VSV, and tested for lysis by VSV specific cytolytic T cells. FACS analysis may also be used to detect MHC class I molecules on the surface of a putative target cell. The biosynthesis and intracellular transport of MHC class I molecules may also be biochemically characterized. For example, endo H which cleaves N-linked oligosaccharides only when they are in the high mannose form characteristic of proteins present in the ER and cis-Golgi complex may be used to measure intracellular transport. Pulse-chase methodology may also be utilized to confirm target cells expressing low levels of MHC class I molecules. The above methods are illustrated in the Examples herein. See also Restifo. N. P. et al, supra, 1993.

Examples of cells which express low levels of MHC class I molecules are tumor cells derived from colon, breast, lung mesothelioma and lung cancers of the small cell histology (See Restifo, N. P., supra 1993).

Cells expressing low or nondetectable levels of TAP-1 and TAP-2 transporter proteins may be detected by assaying for mRNA encoding these proteins, for example using Northern Blot analysis as described in the Examples herein. Examples of cells which express low levels of TAP-1 and TAP-2 are tumor cells derived from lung cancers of the small cell histology.

Target cells may, in addition to expressing low or nondetectable levels of the transporter proteins TAP-1 and TAP-2, express low or nondetectable levels of one or more of the components of the proteasome, for example LMP7 and LMP-2.

The present inventors have demonstrated that TAP-1 or TAP-2 alone can enhance expression of MHC class I molecule-endogenous peptide complexes on the surface of tumor cells, thereby rendering the tumor cells susceptible to immune surveillance by CTL.

Accordingly, the present invention provides a method of augmenting the immune response of a mammal to a tumor cell comprising: introducing a nucleic acid molecule comprising a sequence encoding a TAP molecule into the tumor cell under control of a suitable promoter and; expressing the TAP molecule in the tumor cell under suitable conditions, thereby enhancing the immune response to tumor cell. For the treatment of tumors, the TAP molecule can be administered directly in vivo or can be used to transfect tumor cells ex vivo which are re-infused into the patient. When the TAP molecule is administered directly in vivo it can be administered by any route including, but not limited to, intraperitoneally, intravenously, intratumorally, subcutaneously, intradermally, mucosally, submucosally or orally.

In a preferred embodiment, the method further comprises: introducing an additional nucleic acid molecule into the tumor cell, said additional nucleic acid molecule comprising a sequence encoding an antigenic peptide under control of a suitable promoter and; expressing the antigenic peptide in the tumor cell under suitable conditions, thereby enhancing presentation and processing of the antigenic peptide permitting recognition by the mammal's immune response.

The invention still further relates to a method of preparing tumor specific T cells which have anti-tumor properties comprising removing tumor cells from a subject; introducing a nucleic acid molecule encoding TAP-1 or TAP-2 under the control of a suitable promoter into the tumor cells; implanting the tumor cells in the subject or a mammal have a reconstituted immune system of the subject; and harvesting tumor specific T cells. It will be appreciated that in an embodiment the nucleic acid molecule may also encode both TAP-1 and TAP-2 or that separate nucleic acid molecules encoding TAP-1 and TAP-2 may be introduced into the tumor cells. The tumor specific T cells may be used as a therapeutic agent in vivo in the subject. Methods such as those described in Restifo. N. P. et al *J. Exp. Med.* 175:1423-1431 may be used to prepare specific T cells which anti-tumor properties in vivo using tumor cells transfected with IFN-γ. Adoptive immunotherapy models can be used to confirm the utility of the preparation against established non-modified tumor cells in vivo.

The invention also contemplates that nucleic acid molecules encoding TAP-1 and/or TAP-2 may be incorporated into recombinant viral vector vaccines for use in augmenting the immune response to a pathogen or tumor. Such vaccines can be used to treat infectious agents or to treat cancers. Such vaccines are expected to have particularly useful application for mammals, including humans, which are unable to mount an immune response to certain viral or tumor antigens or where their HLA makeup does not permit adequate processing and presentation of the relevant antigenic peptide. For example, for use in persons or for tumor cells lacking in components of the antigen presentation system, such as TAP-1, TAP-2 and proteasome components. It will be appreciated that the nucleotide sequences encoding TAP-1 and TAP-2 may be used separately or may be included together, either under the control of separate promoters or under the control of the same promoter.

Recombinant vaccinia virus vaccines may be constructed using techniques known in the art. For example, the pJS5 shuttle vector which contains two early/late compound promoters may be used to express both TAP and the relevant antigen in an infected cell simultaneously. The TAP gene or genes may be cloned behind one promoter and the protein or peptide gene can be cloned behind the second promoter, or in a second vaccine. TAP-1 may be cloned behind one promoter and TAP-2 may be cloned behind a second promoter. The cloned genes may be flanked by the thymidine kinase gene. The pJS5-TAP antigen vector can be transfected into a vaccinia infected cell so the homologous recombination can occur between the thymidine kinase sequence in both vaccinia and the cloned shuttle vector, resulting in either a recombinant vaccinia virus containing TAP and the antigen, or a recombinant vaccinia virus containing both TAP-1 and TAP-2 which would allow particular peptides to be transported and presented.

The invention also contemplates a method for inhibiting rejection by a recipient animal of a transplanted tissue comprising modifying, eliminating, or masking expression of TAP-1. TAP-2 or both TAP-1 and TAP-2 in cells of said tissue to inhibit endogenous antigen processing and presentation on the surface of cells of said tissue which cause a T-lymphocyte mediated response in said animal. Expression of TAP-1, TAP-2 or TAP-1 and TAP-2 may be modified, eliminated or masked using TAP-1. TAP-2 and/or TAP-1 and TAP-2 antisense. Class I MHC molecules may also be eliminated from the cells of the transplant tissue and truncated forms of TAP-1. TAP-2 and/or TAP-1 and TAP-2 may be used to compete with the functional transporters resulting in down-regulation of expression of TAP-1 and/or TAP-2.

II. Compositions

The present invention also includes pharmaceutical compositions or vaccines for carrying out the methods of the invention. Accordingly, the present invention provides a pharmaceutical composition for use in enhancing an immune response comprising an effective amount of an agent that can augment the level of a TAP molecule in admixture with a suitable diluent or carrier. In a preferred embodiment, the pharmaceutical composition comprises an effective amount of a nucleic acid molecule comprising a sequence encoding a TAP molecule in admixture with a suitable diluent or carrier.

The above described nucleic acid molecules encoding a TAP molecule or a vector comprising the nucleic acid molecules may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals.

The vaccines or pharmaceutical compositions can contain other molecules such as the antigen to which one wishes to generate an immune response and/or stimulatory molecules as hereinbefore described.

The pharmaceutical composition may be administered in a convenient manner such as by injection (subcutaneous, intravenous, intraperitoneal, intratumoral etc.), oral administration, inhalation, transdermal application, or rectal administration. Depending on the route of administration, the nucleic acid molecules may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985) or Handbook of Pharmaceutical Additives (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456. As will also be appreciated by those skilled, administration of substances described herein may be by an inactive viral carrier.

The following examples are offered by way of illustration only, and not by way of limitation.

EXAMPLES

The following materials and methods were utilized in the investigations outlined in Examples 1 to 8.

Animals and Viruses

C57Bl/6 mice were bred at the University of British Columbia breeding facility. Mice were 6-12 weeks old and were maintained in accordance with the guidelines of the Canadian Council on Animal Care. VSV was grown on vero cell monolayers. Vaccinia and a human $\beta_2M$ (h$\beta_2$m) vaccinia recombinant were gifts from Dr. J. Yewdell.

Cell Lines and Antibodies

CMT.64 cells (H-2b), were provided by Dr. L. M. Franks (Franks, L. M. et al 1976, Cancer. Res. 36:1049). RMA and RMA-S cells were maintained in DMEM supplemented with 10% heat activated FCS, 20 Mm Hepes, 2 mM glutamine, and antibiotics. The mABS used were as follows: 142-23.3 anti H-2 $K^b$, 28-11-5s anti H-2 $D^b$ ($\alpha1+\alpha2$), 28-14-8s anti H-2 $D^b$ ($\alpha3$) and BBM.1 against human $\beta_2$m (Brodsky, F. M. et al, 1979, Eur. J. Immunol. 9:536). A rabbit antiserum against h$\beta_2$M (Bikoff. E. K et al, 1991, Nature 354:235), against exon-8 of H-2$K^b$ (Williams, D. et al, 1989, J. Immunol. 142: 2796) and against rat proteasome (Brown. M. G. et al, 1991, Nature 353:357) were also used.

Transfection

Transfection of CMT.64 cells with cDNA from rat TAP-1 in the pHb Apr-l-neo expression vector (provided by Dr. G. Butcher) was achieved by lipofection (Lipofectin, Gibco BRL, Gaithersburg, Md.) using IOµg of DNA. Selection was in I mg/ml G418 (Gibco BRL). Positive clones were selected and screened by Northern blotting for expression of the rat TAP-1 gene. The results obtained with a representative clone are reported (See FIG. 9). As negative controls, clones obtained from a vector DNA transfection were analyzed by Northern Blotting. The results obtained with a representative clone are reported (See FIG. 9).

Flow Cytometry Analysis

To determine the cell surface expression of MHC class I molecules fluorescence-activated cell sorter (FACS) analysis (Becton Dickinson & Co., Mountain View, Calif.) was used. RMA, RMA-S and CMT.64 cells were treated with or without recombinant murine gamma interferon (IFN-γ) at 150-300 units/ml (Genzyme Cytokine Research Products) for 48 hours. The cells were collected and incubated overnight in medium without FCS, with VSV-N 52-59 peptide (50 µM) and/or h$\beta_2$m (2.5 µg). Peptides were purchased from the University of Victoria, Peptide Synthesis Facility (Victoria, BC, Canada). The cells were subsequently removed from culture, washed, and incubated with 1:50 dilution of 142-23.3 ascites, or 200 µl of cell culture supernatant from 28-11-5s and 28-14-8s cells for 45 min on ice. After two washes, the cells were incubated with 100 µl of 1:20 dilution of goat anti-rabbit, or goat anti-mouse FITC conjugated secondary antibody for another 45 minutes on ice. The samples were then fixed in paraformaldehyde (1.5% in phosphate buffered saline) and analyzed on a FACScan® cell sorter using the FACScan® program (Becton Dickinson & Co.). Values reported in Table 1 are in linear terms representing the average of 5,000 cells. The corrected value (minus the value without first antibodies) is reported.

Cell Labeling, Pulse-Chase Experiments, Immuoprecipitation, Isoelectric Focusing and SDS-PAGE Cells were washed in MEM medium without methionine 1 hour before labeling and labeled with 150 µCi/Ml of $^{35}$S methionine for 1 hour or as indicated. For the pulse-chase experiments, cells were labeled 15 minutes and then chased with normal medium containing an excess of cold methionine. Labeled cells were solubilized with 1 ml of 20 Mm Tris-Hcl (pH 7.6) containing 0.12 M NaCl, 4 Mm $MgCl_2$ and 1% Nonidet P-40, phenylmethylsulfonylfluoride (PMSF, a protease inhibitor) was added to a final concentration of 20 µg/ml before use. After 15 min on ice, particulate material was removed by centrifugation. The supernatant was used for immunoprecipitation of labeled antigens. Labeled solubilized antigens were first precleared with 2 of normal rabbit serum for 45 min at 4° C. followed by 50 µl of protein A-Sepharose (1:1 in solubilization buffer) for another 45 minutes at 4° C. Protein A-Sepharose was removed by a quick centrifugation. The precleared supernatant was reacted with the appropriate antibody or immune serum for 1 hour at 4° C. 35 µl of protein A-Sepharose was added and incubation continued for a further 30 minutes. After centrifugation the beads were washed twice with 0.2% NP-40 in 10 mM Tris-HCl pH 7.5, 0.15 M NaCl and 2 mM EDTA, once with 0.2% NP40 in 10 Mm Tris-HCl, pH 7.5, 0.5 M NaCl, 2 mM EDTA and finally with 10 mM Tris-HCl pH 7.5. One-dimensional isoelectric focusing was performed as previously described in Celis. J. E. et al (1990. *Electrophoresis* 11:989). SDS-PAGE was carried out as described in Kvist, S. et al, (1982, *Cell* 29:61).

CTL Response Against VSV-Infected, IFN-γ Induced Cells

RMA, RMA-S and CMT.64 cells were treated with or without IFN-γ at 200 units per ml for 48 hours. They were subsequently washed 3× with PBS and treated with VSV at a multiplicity of infection (MOI) of 5 min in 0.5 ml of medium for one hour. The cultures were then incubated in a total of 3 ml of growth medium for an additional 4-8 hours (as indicated), to allow infection to proceed. Single cell suspensions were treated with 100 µCi $^{51}$Cr per $10^6$ cells for 2 hours in RPMI 1640 supplemented with L-glutamine and penicillin/streptomycin in the absence of fetal bovine serum (FBS) and sodium bicarbonate. Alternatively. CMT.64 cells were infected with Vaccinia (V), and/or Vaccinia-β2m (Vb2) at an MOI of 5 for 5 hours followed by superinfection with VSV (MOI, 5) for an additional 4 hours. The cells were washed 3× and subsequently incubated at $10^4$ cells per well in 96-well plates with the effector population at ratios of 100 to 12.5. Mock infected cells were used as negative controls. The effector CTL population was generated by immunizing C57Bl/6 mice with VSV at $5×10^6$–$1×10^7$ $TCID_{50}$ in the foot pads and ears. On day 5 post immunization the draining lymph nodes (retropharyngeal and popliteal) were harvested and cultures initiated at $4×10^6$ cells per ml in a total volume of 5 ml in 6-well plates. The culture medium consisted of RPMI-1640 supplemented with $5×10^{-5}$ M 2-mercaptoethanol (ME), 10% heat inactivated FBS, sodium pyruvate, penicillin, streptomycin, L-glutamine. HEPES, sodium bicarbonate, and 50% NCTC-109. Cultures were incubated for three days at 37° C. and 5% $CO_2$ in the absence of exogenous stimulation. The $^{51}$Cr release was measured by a compugamma counter (model 1282 CS; LKB Instruments, Gaithersburg, Md.) and the specific $^{51}$Cr release calculated as [(experimental−media control)/(total−media control)]×100%. The spontaneous release never exceeded 17% of the maximum release.

RNA Extraction and Northern Analysis

Total cellular RNA was prepared from cell lines using guanidinium isothiocyanate (GITC). Briefly, the cells were lysed in 4 M GITC then centrifuged (130,000 g for 16 hours at 23° C.) through a cushion of cesium chloride. After ethanol precipitation, the purified RNA was resuspended in DEPC-treated $H_2O$. 10 µg of each sample was loaded and separated on a 1% agarose gel containing 2.2 M formaldehyde. The gel was blotted onto Hybond N (Amersham Corp., Arlington Heights, Ill.) and UN fixed prior to hybridization. The $^{32}$P-labelled probes used for hybridization were as follows: MTP1 and MTP2 (TAP-1 and -2 respectively, kindly provided by Dr. Geoff Butcher), prepared by random priming, and an oligonucleotide specific for β-actin labelled by terminal transferase. Hybridization was carried out at 42° C. in buffer containing 0.4 M $Na_2HPO_4$, 50% formamide and 7% SDS. Several washes were performed at 42° C. under conditions of increasing stringency and the filter exposed to X-OMAT AR film (Kodak) overnight.

Example I

Comparison of the Phenotypes of CMT.64 and RMA-S Cells

The small lung carcinoma cell line. CMT.64, was shown to express and assemble MHC class I molecules on the cell surface after IFN-γ treatment (Klar D. and Hammerling, 1989, EMBO J. 8:475; Sibille, C. et al, 1992, *Eur. J. Immunol.* 22:433; and Jefferies W. A. et al. 1993, *J. Immunol.* 151: 2974). In order to understand the molecular deficiency in antigen processing of CMT.64 cells, the contrasting phenotypes of CMT.64 cells versus RMA-S cells were analyzed. CTL recognition of VSV infected RMA, RMA-S, CMT.64 IFN-γ induced or uninduced cells was investigated generally following the methods outlined in the methodology section herein. More particularly, target cells were treated with or without IFN-γ for 48 hours prior to infection with VSV and the results are shown in FIG. 1. Panel A in FIG. 1 illustrates a representative experiment using RMA and RMA-S cells as targets, whereas panel B is the equivalent experiment with CMT.64 cells (abbreviated: C). All cells were infected with VSV at an MOI of 10 for 4 hours. IFN-γ treatment is denoted in FIG. 1 with a + sign following the cell line designation. Spontaneous release did not exceed 15%.

Figure 1B:
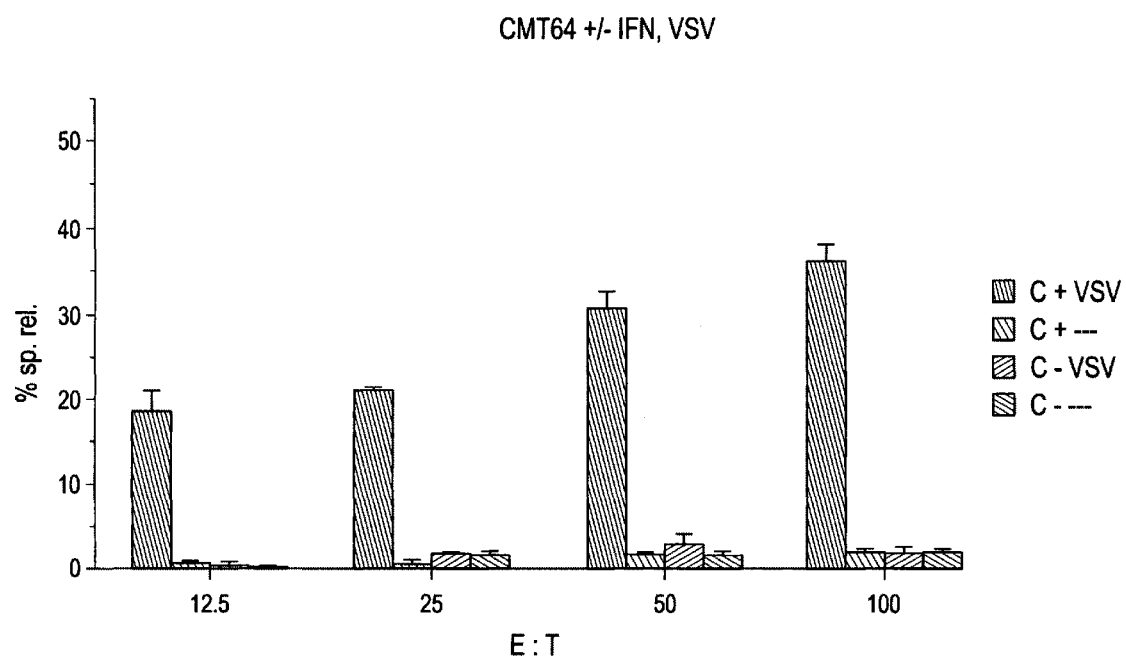
FIG. 1B depicts histograms showing CTL recognition of VSV infected CMT.64 cells (abbreviated: C) IFN-γ induced (+) or uninduced cells.

VSV infected RMA-S cells are recognized as efficiently as the wild-type RMA cells with or without IFN-γ treatment (FIG. 1A), in comparison to VSV infected CMT.64 cells which are not recognized by specific CTL unless induced by IFN-γ (FIG. 1B). It should be noted that RMA-S, RMA and CMT.64 cells are equally permissive to infection with VSV as indicated by the number of infective particles produced following infection measured by a $TCID_{50}$ assay (data not shown). Therefore, uninduced CMT.64 cells have a different or additional deficiency to the functionally defective peptide transporter TAP-2 present in RxA-S cells.

Example 2

The Effect of Exogenous and Endogenous Peptide on the Phenotypes of CMT.64 and RMA-S Cells Previous experiments have demonstrated that treatment of mutant cells with exogenous peptides and/or human β$_2$m can stabilize "empty" class I molecules at the cell surface (Townsend. A. et al. 1989, *Nature* 340:443; Vitiello, A., et al., 1990. *Science* 250:1423; and Ljunggren, H.-G., et al. 1990. *Nature* 346:476). RMA, RMA-S and CMT.64 cells uninduced or induced with IFN-γ were treated overnight with exogenous peptides VSV-N 52-59 at 50 μM in the presence or absence of human $\beta_2$m. VSV-N 52-59 peptides and $\beta_2$m synergistically increase the expression of the $K^b$ conformational specific epitope recognized by 142.23.3 mAb (Table 1) on RMA and RMA-S cells. VSV-N 52-59 peptides specifically affect the stability and the conformation of the $K^b$ molecules and have no effect on $D^b$ molecules. Human $\beta_2$m binds to $K^b$ and $D^b$ molecules, which is detected by BBM.1 (anti-human $\beta_2$m mAb), and appears to stabilize heavy chains before they can disassemble at the cell surface. A stabilizing effect was not seen after CMT.64 treatment with peptides or $\beta_2$m alone. Additional treatment of CMT.64 cells with IFN-γ was required for high expression of $K^b$ and $D^b$ conformation specific epitopes on the cell surface (Table 1). Therefore, CMT.64 cells express much lower amounts of 'empty' class I molecules at the cell surface than RMA-S cells.

Figure 2:
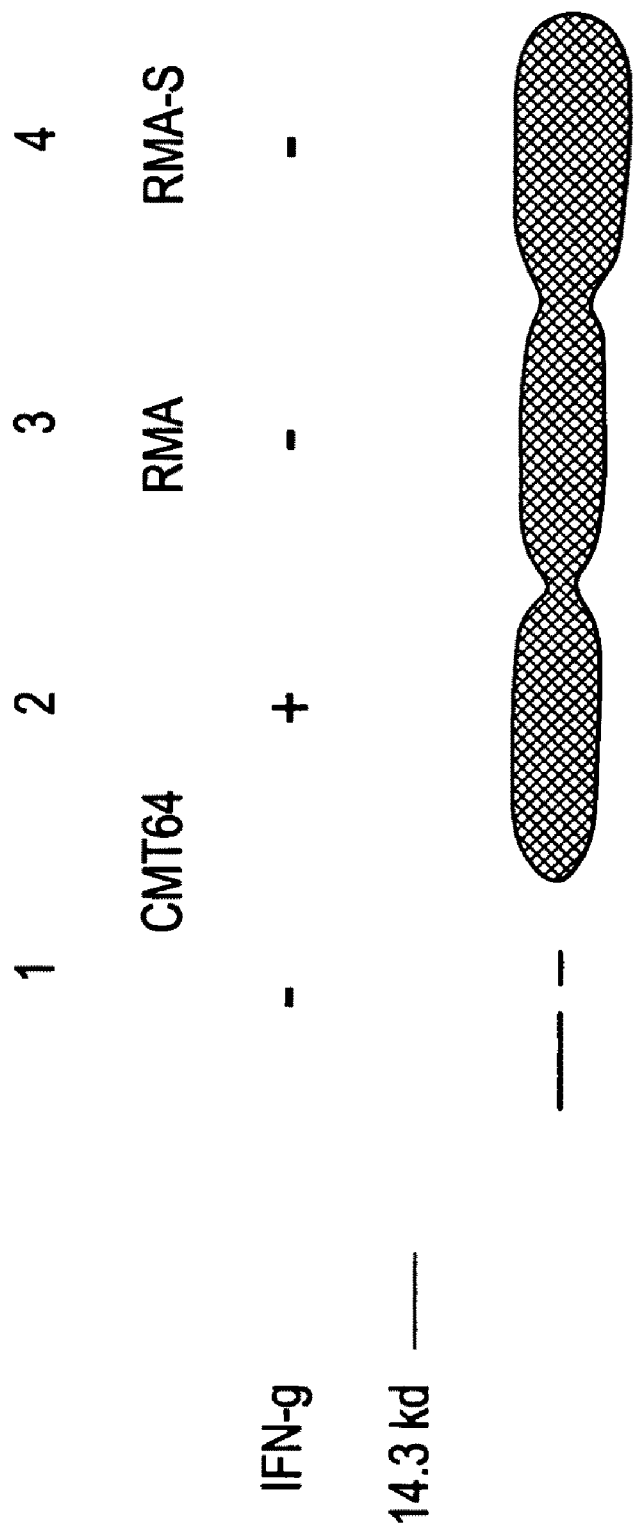
FIG. 2 is an autoradiogram showing the amount of $\beta_2 m$ synthesized in RMA. RMA-S and CMT.64. IFN-γ induced (+) or uninduced (−) cells.

Earlier work has shown that the presence of $\beta_2$m and peptides within the lumen of the ER is necessary for efficient assembly and cell surface expression of MHC class I molecules (Rock, K., et al., 1991, *Cell* 65:611). FIG. 2 shows the amount of $\beta_2$m synthesized in RMA. RMA-S and CMT.64 IFN-γ induced or uninduced cells. Cells were labeled for 2 hours with $^{35}$S-methionine lysed, immunoprecipitated with a rabbit anti-h$\beta_2$m serum, and analyzed by SDS-PAGE. Radioactive proteins were detected after 6 hours exposure to a JAR film. CMT.64 cells treated (+) or not (−) with IFN-γ, RMA and RMA-S cells were used (FIG. 2). The migration of the molecular weight marker is indicated on the left of FIG. 2.

As illustrated in FIG. 2, CMT.64 cells express a low amount of endogenous $\beta_2$m (FIG. 2, lane 1). IFN-γ induced CMT.64 cells express a much higher amount of $\beta_2$m, which is comparable to the level expressed in RMA and RMA-S cells (FIG. 2, lanes 2-4).

Figure 3:
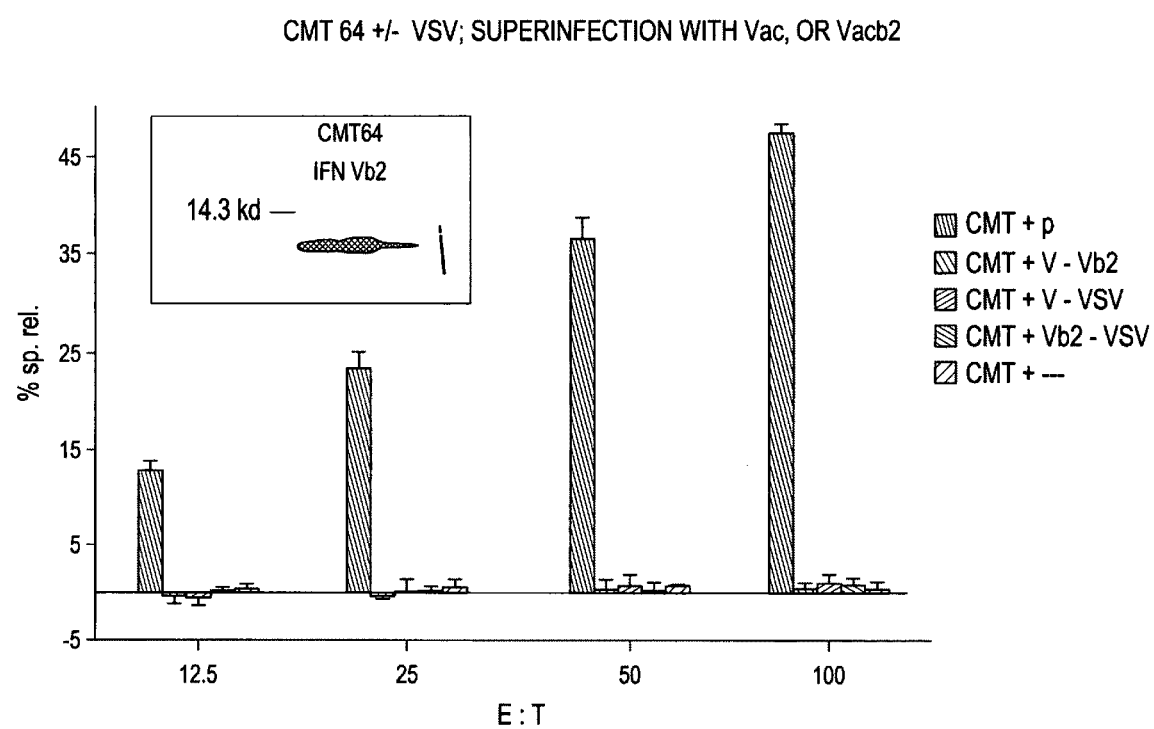
FIG. 3 is a histogram showing the effect of $\beta_2 M$ on the CTL response against CMT.64 cells superinfected with vaccinia virus (VV) and Vaccinia-$\beta_2 m$ recombinant (VV-$\beta_2 m$), Vaccinia and VSV (V-VSV), rVV-VSV or Vaccinia-$\beta_2 m$, and VSV (Vb2-VSV), the insert shows the level of $\beta_2 m$ synthesized after immunoprecipitation with the anti-h$\beta_2 m$ rabbit serum.

To investigate the effect of $\beta_2$m in CMT.64 cells, a recombinant vaccinia virus was used to increase the amount of endogenous $\beta_2$m. The effect of $\beta_2$m on the CTL response against CMT.64 cells is shown in FIG. 3. Infected CMT.64 cells were superinfected with Vaccinia and Vaccinia-$\beta_2$m recombinant (V-Vb2), Vaccinia and VSV (V-VSV), or Vaccinia-$\beta_2$m and VSV (Vb2-VSV) in FBS free media (MOI 3) for up to an additional 12 hours. In the inset in FIG. 3, the level of $\beta_2$m synthesized is shown after immunoprecipitation with the anti-h$\beta_2$m rabbit serum. CMT.64 cells treated with peptide VSV-N52-59 at 500 μM for 2 hours (CMT+---) was used as the positive control, whereas mock treated CMT.64 cells (CMT+---) were used as the negative control. Radioactivity released is the average of quadruplicate wells. Spontaneous release did not exceed 16%.

As illustrated in FIG. 3, elevating the amount of $\beta_2$m synthesized using a recombinant vaccinia virus did not restore CTL recognition of VSV infected CMT.64 cells. Therefore, increasing expression of $\beta_2$m does not induce presentation of VSV-N peptides in the context of $K^b$ molecules. The CMT.64 antigen processing phenotype is not caused by the low amount of endogenous $\beta_2$m.

Example 3

Intracellular Transport of MHC Class I Molecules $D^b$ and $K^b$

Figure 4:
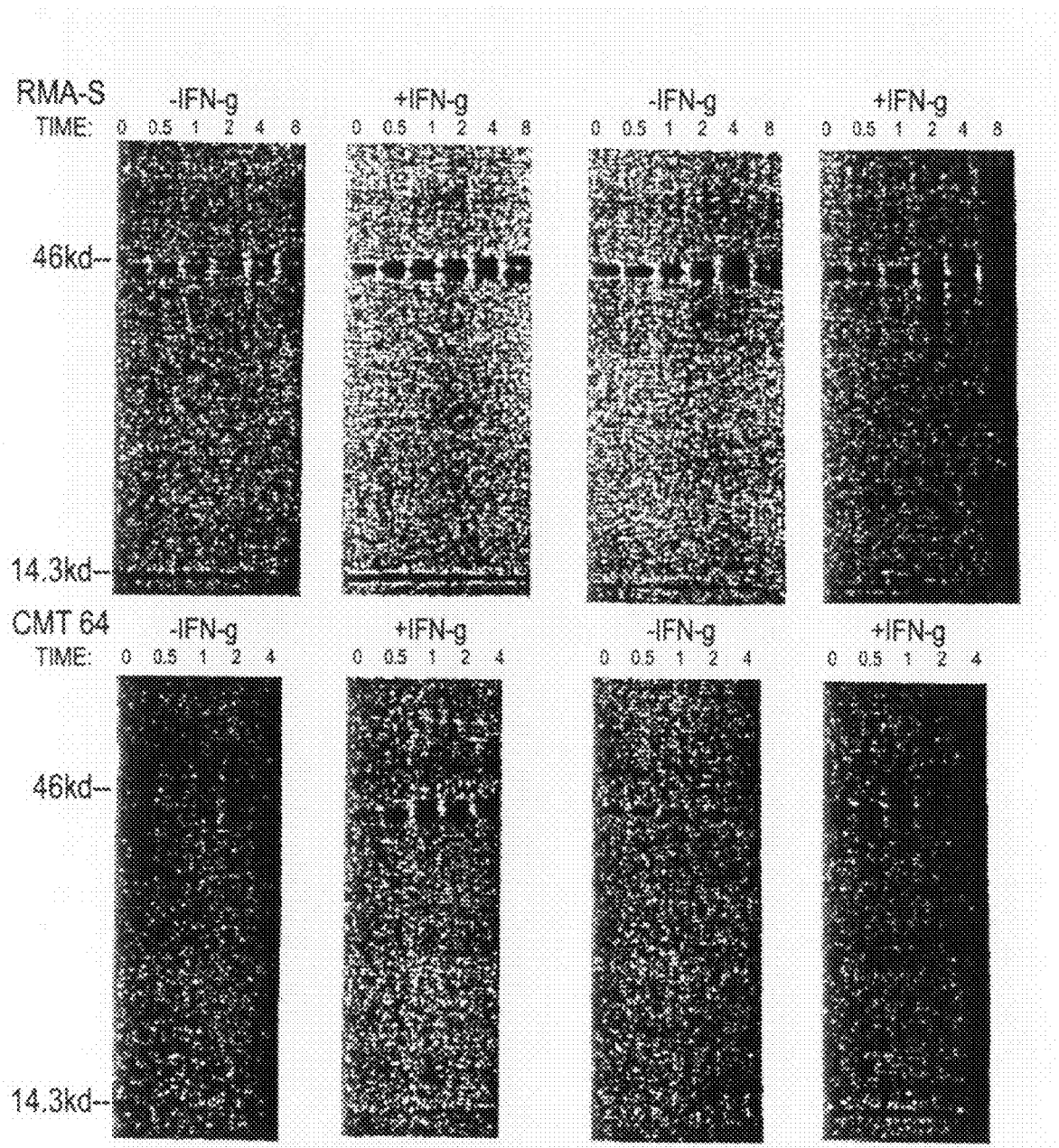
FIG. 4 depicts autoradiograms showing the intracellular transport of MHC class I molecules, $D^b$ and $K^b$.

The transport of $K^b$ and $D^b$ molecules was examined after a pulse-chase labelling of CMT.64, RMA and RMA-S cells and SDS-PAGE analysis of the immunoprecipitated material (for $K^b$, 142.23.3 mAb was used and for $D^b$, 28-14-8s an α3 specific mAb was used). Intracellular transport of MHC class I molecules, $D^b$ and $K^b$ is shown in FIG. 4. Cells were labelled with $^{35}$S-methionine and chased in an excess of cold methionine for the times indicated in hours at the top of FIG. 4. Solubilized antigens were immunoprecipitated with 142.23.3 mAbs for $K^b$ or 28-14-8s mAbs for $D^b$. Treatments are indicated on top and the migration of the molecular weight markers is indicated on the left of FIG. 15. Communoprecipitation of the heavy chains (46 kD) and $\beta_2$M (12 kD) can be seen for all cells except for CMT.64 uninduced cells. Radioactive proteins were detected after 8 days exposure for RMA-S cells and 4 days for RMA and CMT.64 cells to a XAR film.

Despite a similar amount of $K^b$ molecules synthesized in RMA and RMA-S cells (FIG. 4, 0 hour chase time), only low amounts of $K^b$ are processed to a higher mol. weight form indicative of the level of transport which accounts for the surface expression of $K^b$ in RMA-S cells. The processed form is resistant to endoglycosidase H digestion (data not shown) indicating transport out of the ER. The observation that much more $\beta_2$M was immunoprecipitated with $K^b$ molecules than with $D^b$ molecules in RMA-S cells (FIG. 4) may indicate that the mAb 142.23.3 only recognizes the assembled form, heavy and light chains of $K^b$ molecules, whereas the mAb 28-14-8s recognizes the α3 region of $D^b$ molecules. The presence of a functional TAP-1 protein in RMA-S cells (Yang. Y. et al., 1992, *J. Biol. Chem.* 267:11669) may be sufficient to enable some peptides to cross the ER membrane and bind a small number of $K^b$ molecules allowing them to go to the cell surface. Also, peptides with lower affinity for $K^b$ molecules may bind and aid the molecules to assemble and go to the cell surface where they dissociate. Much fewer mature processed $D^b$ molecules were detected in RMA-S cells after 4 hours chase (FIG. 4). This may indicate a lower affinity of $D^b$ for $\beta_2$M and/or fewer peptides available for $D^b$ binding. In RMA cells, $K^b$ molecules were processed within 1 hour. In comparison, $D^b$ molecules were processed more slowly (2 hours) (FIG. 4). These results are in agreement with the relative transport rate of $K^b$ and $D^b$ in RMA-S cells. IFN-γ treatment augments the synthesis of heavy chains causing more $K^b$ and $D^b$ molecules to be transported to the cell surface of RMA and RMA-S cells. The rate of transport of $K^b$ and $D^b$ molecules was not affected by IFN-γ treatment in RMA and RMA-S cells. In contrast, no $K^b$ molecules were detected in CMT.64 cells using the 142.23.3 mAb Example 4

Intracellular Transport of Free and Assembled Forms of $K^b$, Molecules in Uninduced and IFN-γ Induced CMT.64 Cells As discussed above, the 142.23.3 mAb may not recognize the unassembled and peptide free heavy chains of $K^b$ molecules (FIG. 4). In order to address this issue, a rabbit anti-exon 8 serum directed against a conformation independent epitope recognizing a peptide in the cytoplasmic tail of H-2$K^b$ molecules (Williams, D. et al, 1989, *J. Immunol.* 142:2796) was used to detect and follow the processing of K' molecules in uninduced or IFN-γ induced CMT.64 cells.

Figure 5:
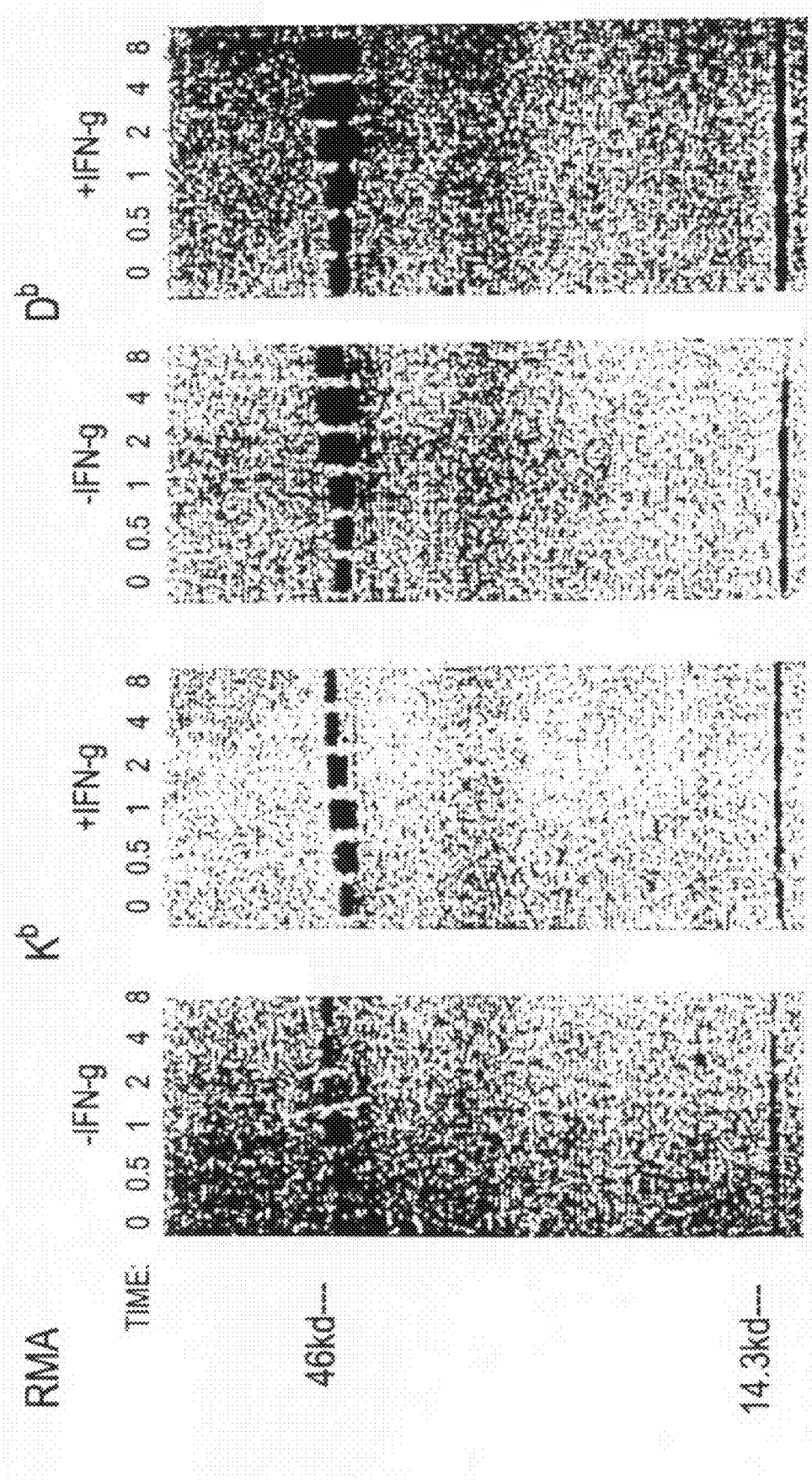
FIG. 5 depicts autoradiograms showing the intracellular transport of free and assembled forms of $K^b$ molecules in uninduced and IFN-γ-induced CMT.64 cells.

Cells were labelled with $^{35}$S-methionine and chased in an excess of cold methionine for the times indicated in hours at the top of FIG. 5. Solubilized antigens were immunoprecipitated with a rabbit anti-exon 8 of H-2$K^b$ serum recognizing the cytoplasmic tail of free and assembled $K^b$ heavy chains as described herein. Treatments are indicated on top and the migration of the molecular weight markers is indicated on the left of FIG. 5. Radioactive proteins were detected after 4 days exposure to a RPN-30 film (Amersham, Corp.).

In uninduced CMT-64 cells, $K^b$ molecules were detectable early after synthesis (FIG. 5, 0 h, 0.5 h and 1 h chase time), but were unstable and mostly degraded after 8 h chase with very few molecules processed to a higher mol. weight (FIG. 5, 8 h chase time). In induced cells. $K^b$ molecules were synthesized in higher amounts and a greater proportion of the molecules were processed to a higher mol. weight (FIG. 5). The decrease in the amount of material immunoprecipitated by this anti-serum during the chase could not be explained. A loss or degradation of the epitope recognized by the anti-serum during transport is possible. Furthermore, $D^b$ molecules are also synthesized and are then degraded or denatured (FIG. 4). In uninduced CMT.64 cells, no processed $D^b$ molecules were detected even after 4 hours chase. Only treatment with IFN-γ results in higher expression, increased transport and increased transport rate of $K^b$ and $D^b$ molecules in CMT.64 cells. Thus, components necessary for the assembly and transport of $K^b$ heavy chains and $β_2$m were induced by IFN-γ in CMT.64 cells, while similar induction did not significantly alter the transport of $D^b$ and $K^b$ in RMA or RMA-S cells. This indicates that CMT.64 cells are likely deficient in components necessary for MHC class I assembly which differ from the TAP-2 defect in RMA-S cells.

Example 5

VSV-N 52-59 Peptide Response in CTL Recognition

Figure 6:
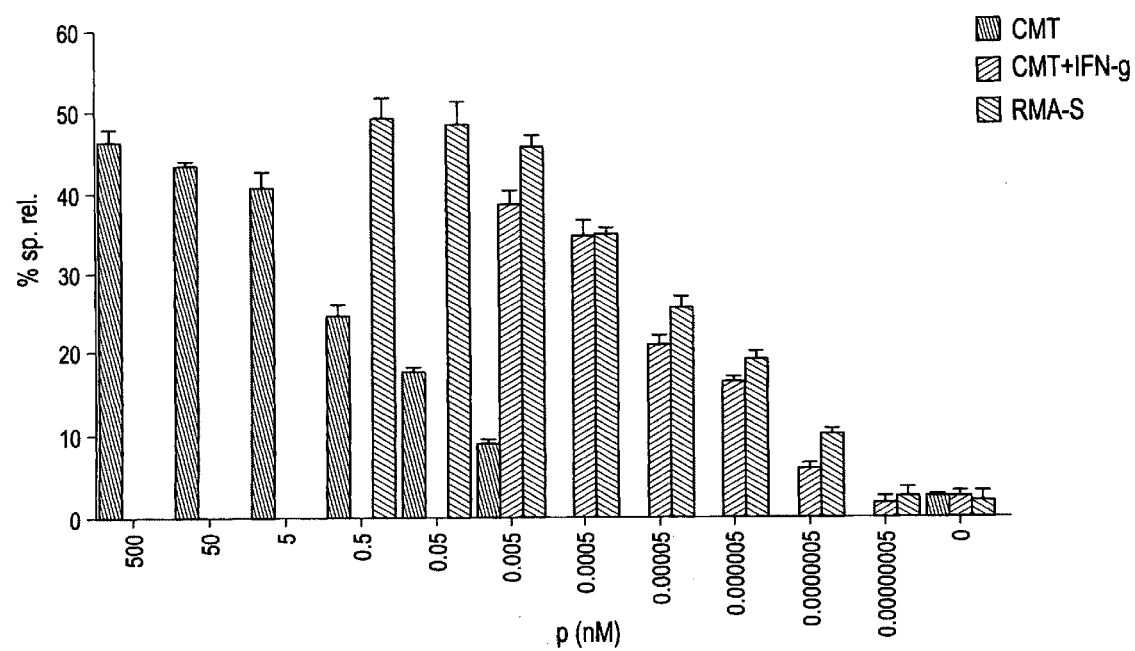
FIG. 6 is a histogram showing VSV-N 52-59 peptide dose response in CTL recognition for CMT.64 cells (CMT), CMT.64+IFN-γ (CMT+IFN-γ) and RMA-S cells (RMA-S)

In order to assay the function of the MHC class I molecules, the CTL recognition of CMT-64 cells IFN-γ induced or uninduced and RMA-S cells treated with exogenous peptides was examined. CMT.64 cells (CMT), CMT.64+IFN-γ (CMT+IFN-γ) and RMA-S cells (RMA-S) were treated with peptide N52-59 at the concentrations indicated in FIG. 6. The radio-activity released by specific CTL recognition and lysis was measured and represented as indicated in materials and methods described above. Radioactivity released, shown in FIG. 6, is the average of quadruplicate wells. Spontaneous release did not exceed 13%.

In a dose dependent manner. RMA-S and CMT.64 IFN-γ treated cells were 10,000 times more sensitive than CMT.64 cells to killing by specific CTL after 2 hours treatment with exogenous peptides (FIG. 6). These results provide evidence for the low expression of peptide receptive MHC class I molecules on the surface of uninduced CMT-64 cells. In the dose-response on RMA-S cells, a maximum of 15,000 peptide molecules per cell were needed to achieve 50% killing by specific CTL, whereas a lower threshold of 150 molecules per cell resulted in the release of 5-10% of $^{51}$Cr. These data may be explained by a high amount of receptive molecules or high affinity of the 5 MHC class I molecules for the peptide on the surface of RMA-S and IFN-γ induced CMT.64 cells. Under the conditions of the present assay, where there is no exogenous $β_2$m, the exogenously added peptides likely stabilize the empty $K^b$ molecules which arrive at the cell surface of RMA-S before they dissociate from $β_2$m (Rock. K. et al, 1991, Cell 65:611 and Jefferies W. et al, supra, 1993). The low amount of empty Kb transported in uninduced CMT.64 cells would explain the difference in sensitization to exogenous peptides.

Example 6

Expression of TAP-1 and TAP-2 Genes in CMT.64 and RMA-S Cells

The results shown in FIGS. 2 to 6 indicate that despite its lower expression, $β_2$m alone is not responsible for the lack of antigen presentation in CMT.64 cells. In addition, $K^b$ $D^b$ and $D^b$ molecules are synthesized in these cells but very few are transported to the cell surface where they bind exogenously added peptides. Besides heavy and light chains, peptides are necessary for the efficient assembly of MHC class I molecules in the ER (Spies, T. et al, 1990, Nature 348:744; Monaco, J. J. et al, 1990, Science 250:1723; Spies, T. and DeMars. R, 1991, Nature 351:323 and; Townsend. A. et al, 1989, Nature 340:443). The possibility that the absence of components responsible for the generation and transport of these peptides within the ER may be responsible for the CMT.64 phenotype was investigated.

Figure 7:
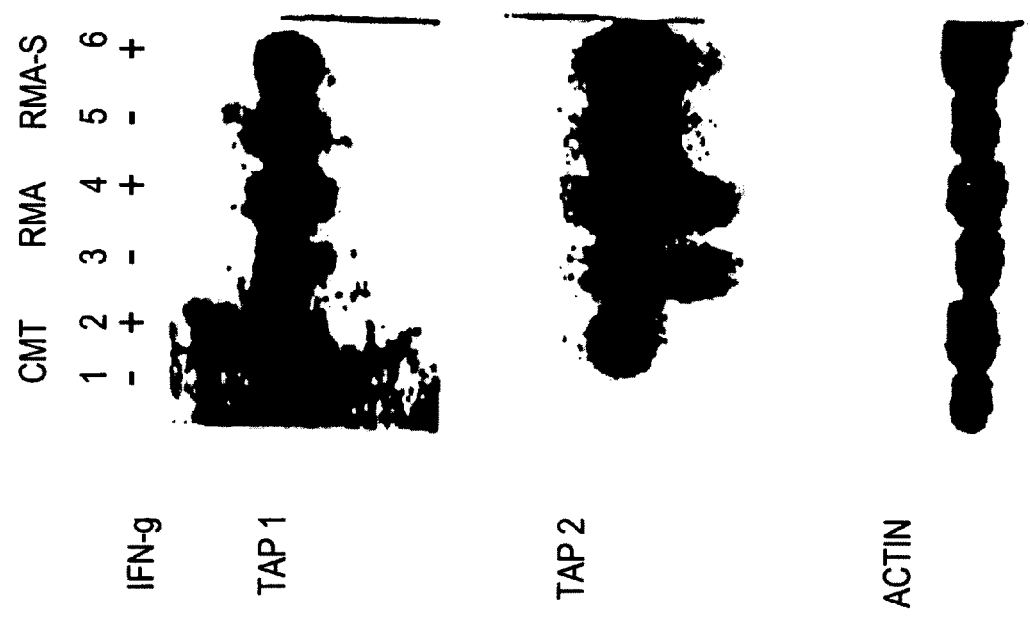
FIG. 7 shows Northern blot analysis of cytoplasmic RNA from RMA, RMA-S, CMT.64 IFN-γ induced and uninduced cells.

A putative peptide transporter, presumed to be composed of a heterodimer of two half-ABC type transporter 35 called TAP-1 and TAP-2, has been implicated in translocating peptides into the ER for MHC class I assembly (Kelly. A. et al, 1992, Nature 355:641 and; Powis. S. H. et al. 1992. Proc. Natl. Acad. Sci. USA 89:1463). To characterize the difference of phenotypes between RMA-8 and CMT.64 cells, the expression of TAP-1 and TAP-2 genes in these cell lines was examined by Northern blot analysis of total cellular RNA from RMA, RMA-S, CMT.64 IFN-γ induced and uninduced cells (FIG. 7). 10 μg of cytoplasmic RNA from CMT.64, RMA and RMA-s cells IFN-γ induced (+) or uninduced (−) were analyzed and the results are shown in FIG. 7. TAP-1, TAP-2 and β-actin probes were hybridized with the membrane. The radioactivity bound to specific RNA sequences was detected after overnight exposure of the membrane to a XAR film.

In FIG. 7, Northern Blot analysis shows that uninduced CMT-64 cells did not express a detectable amount of TAP 1 and TAP-2 mRNA and that the amount of these mRNAs was highly increased after IFN-γ treatment of these cells. in addition. FIG. 7 shows that no major difference exists between TAP-1 and TAP-2 gene expression in RMA-S and RMA cells, and that IFN-γ treatment only marginally affected TAP-1 and -2 expression in these cells. The amount of actin mRNA gives an indication of the near equal amount of mRNA loaded on the gel for Northern blotting. The IFN-γ inducibility of TAP-1 and -2 has been previously demonstrated in mouse tissues (Gaskin. H. R. et al, 1992, Science. 256:1826), however this has not been examined in RMA. RMA-S or CMT.64 cells before this study. The results reported here show that the TAP-1 and TAP-2 genes are IFN-γ inducible in CMT.64 cells and to a lesser degree in RMA and RMA-S cells. The absence of TAP-1 and TAP-2 mRNA expression in CMT-64 cells likely causes a lack of antigenic peptides in the ER for binding to and assembly of MHC class I molecules. This results in the nonrecognition of VSV-infected CMT.64 cells. In contrast, RMA-S cells express a functional TAP-1 molecule that may aid peptides to cross the ER membrane. This would explain the assembly and transport of MHC class I in RMA-S cells and their CTL recognition after VSV infection. The lack of TAP-1 and TAP-2 in uninduced CMT.64 cells may be one of the factors responsible for the phenotype of CMT.64 cells characterized by the formation of unstable and inefficiently transported MHC class I complexes.

Example 7

Proteasome Components from RMA, RMA-S and CMT.64 IFN-γ Induced or Uninduced Cells Before concluding that TAP deficiencies are the likely or only defects in CMT.64 cells, the presence of proteasome components in these cells was examined. Viral peptides are thought to be generated in the cytoplasm by the proteasome (Ortiz-Navarette. V. at al., Nature 353:662, 1991; Brown, M. G. et al., Nature 353:355, 1991; Glynne, R. et al., Nature 353:357, 1991; Martinez, C. K. and, J. J. Monaco, Nature 353:664, 1991; Kelly, A. et al., Nature 353:667, 1991; Yang, Y. et al., Proc. Natl. Acad. Sci. USA 89:4928, 1992; and Goldberg, A. L. and K. L. Rock, Nature 357:375, 1992) before crossing the ER membrane. The proteasome components are likely key players in antigen processing which could be absent in these cells. A rabbit anti-rat proteasome serum was used which recognizes the mouse proteasome. After immunoprecipitation of the proteasomes, the different component low molecular mass polypeptides (LMP) produced in these mouse cells can be analysed by two dimensional gel electrophoresis.

Figure 8:
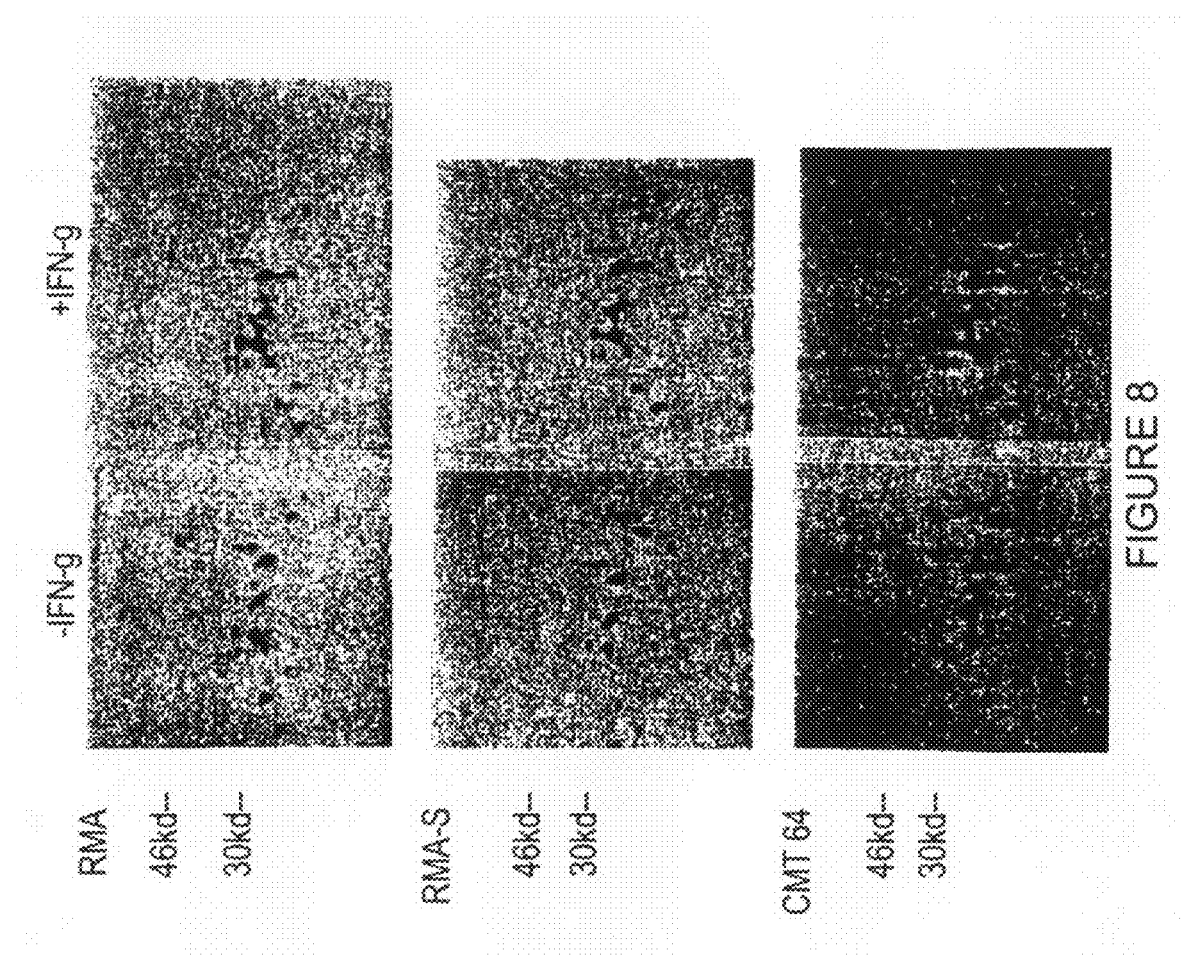
FIG. 8 shows two dimensional gel analysis of proteasome components from RMA. RMA-S and CMT.64 IFN-γ induced or uninduced cells.

Two dimensional gel analysis of proteasome components from RMA, RMA-S and CMT.64 IFN-γ induced or uninduced cells are shown in FIG. 8. Cells were labeled for 2 hours with $^{35}S$ methionine. Solubilized antigens were immunoprecipitated with a rabbit anti-rat proteasome serum and analyzed after isoelectric focusing in a first dimension and 10-15% SDS-PAGE in a second dimension. The radioactive proteins were detected after 10 days exposure to XAR film. Treatment of the cells is indicated on the top of FIG. 8. The acidic side of the gel is on the right and the basic side is on the left of the gel. The migration of the molecular weight markers is indicated on the left of the gel. The missing proteins are indicated by an arrow and are numbered (FIG. 8). Proteins numbered 1 and 7 correspond to LMP-7 and LMP-2, respectively.

Two dimensional gel analysis of immunoprecipitations revealed that the major components of the proteasome are not affected by IFN-γ treatment of CMT.64 cells but that seven components, including LMP-2 and -7, were missing in uninduced CMT.64 cells. According to the results of others (Fruh. K. et al, 1992, J. Biol. Chem. 267:22131), the proteins numbered 1 and 7 in FIG. 8 correspond to LMP-7 and LMP-2, respectively. LMP-2. LMP7 and five other components of the proteasome were upregulated slightly by IFN-γ in RMA and RMA-S cells and induced from a state of an undetectable expression to a higher detectable level of expression in IFN-γ treated CMT.64 cells (FIG. 8). LMP-7 (FIG. 8, 1) is particularly highly induced in CMT.64 cells treated with IFN-γ. These results contrast the results of others which suggested that CMT.64 express a low level of all proteasome components (Ortiz-Navarette, V. et al, 1991, Nature 353:662) and these new results indicate that these induced proteasome components affect the activity of the proteasome and allow the generation of the VSV-N peptides in induced CMT.64 cells. Recent data (Arnold, D. et al., 1992, Nature 360:171, and Momburg. F. et al., 1992, Nature 360:174) suggest that LMP-2 and -7 may not be necessary for influenza virus antigen presentation in mutant cells transfected with the TAP-1 and -2 genes.

The above results show that IFN-γ treatment in addition to inducing transcription of TAP-1 and TAP-2 genes also upregulates the synthesis of seven components of the proteasomes, including LMP-2 and -7. Others describe that components in addition to LMP-2 and LMP-7 are upregulated in Hela cell proteasomes by IFN-γ treatment (Yang. Y. et al., Proc. Natl. Acad. Sci. USA 89:4928, 1992; and Fruh, K. et al., J. Biol. Chem. 267:22131, 1992). However, as these cells are functionally wild-type, the functional ramification of this regulation has not been addressed. Furthermore, as LMP-2 and LMP-7 are first synthesized as precursor proteins which are cleaved into smalled products (Fruh. K. et al., J. Biol. Chem. 267:22131, 1992), it is possible that some of the five additional proteins missing from uninduced CMT.64 cells may be precursor proteins of LMP-2 and LMP-7.

Example 8

Recognition of VSV infected TAP-1 Positive CMT.64 Cells

Consideration of the accumulated data regarding antigen processing in RMA-S and CMT.64 cells leads to the contention that a functional TAP-1 protein homodimer alone may facilitate the transport of the VSV-N 52-59 peptide from the cytosol to the ER lumen where binding to the heavy chains takes place. An alternative explanation is that this peptide does not require a transporter for translocation across the ER membrane but is not generated in the CMT.64 cells. In order to more clearly define the defect affecting the recognition of VSV infected CMT.64 cells by specific CTL, the rat TAP-1 gene was introduced in CMT.64 cells.

Figure 9:
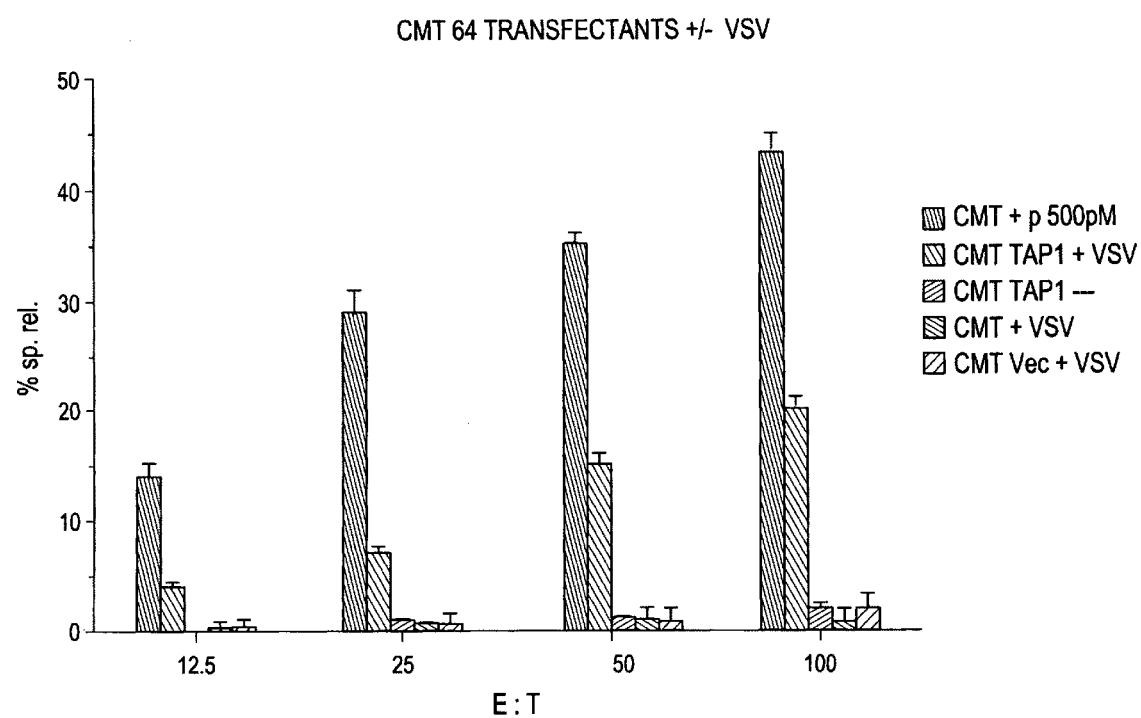
FIG. 9 shows CMT 64 (CMT), and CMT 64 transfected with TAP-1 (CMT TAP 1) infected with or without VSV for 8 hr at MOI of 5, or treated with N52-59 peptide for 2 hr at 500 μM (50% dose response)

CMT 64 (CMT), CMT 64 transfected with TAP-1 (CMT TAP 1), and CMT.64 cells transfected with the vector only (CMT Vec) were infected with or without VSV for 8 hours at MOI of 5, or treated with N52-59 peptide for 2 hours at 500 pM (50% dose response). Spontaneous release did not exceed 12%. FIG. 9 shows that VSV infected TAP-1 positive CMT.64 cells were recognized by specific CTL.

This result explains the RMA-S phenotype and its apparent "leakiness" regarding VSV presentation (Esquivel. F., et al., J. Exp. Med. 175:163, 1992; Hosken, N. A. and M. J. Bevan, J. Exp. Med. 175:719, 1992). TAP-1 alone appeared to be sufficient for VSV presentation in RMA-S cells and in transfected CMT.64 cells and may form a homodimer capable of translocation of specific peptides into the lumen of the ER. In addition to transporters, the difference in the RMA-S and CMT.64 phenotype may be explained at one level by the higher amount of viral peptides generated in RMA-S cells. Interestingly it appears that a total repression of the expression of both LMPs and TAPs localized in the same region of class II may be sufficient for avoiding any expression of class I the cell surface. This may be very important for some cancer cells (Brodsky. F. M. et al., Eur. J. Immunol. 9:536, 1979; Restifo, N. P. et al., J. Exp. Med. 177:265, 1993; and Bikoff. E. K. et al., Eur. J. Immunol. 21:1997, 1991) by providing a method by which tumour cells avoid immunosurveillance.

Example 9

Tap Gene Expression Profiles of CMT.64 and CMT64/R1-4

Figure 10:
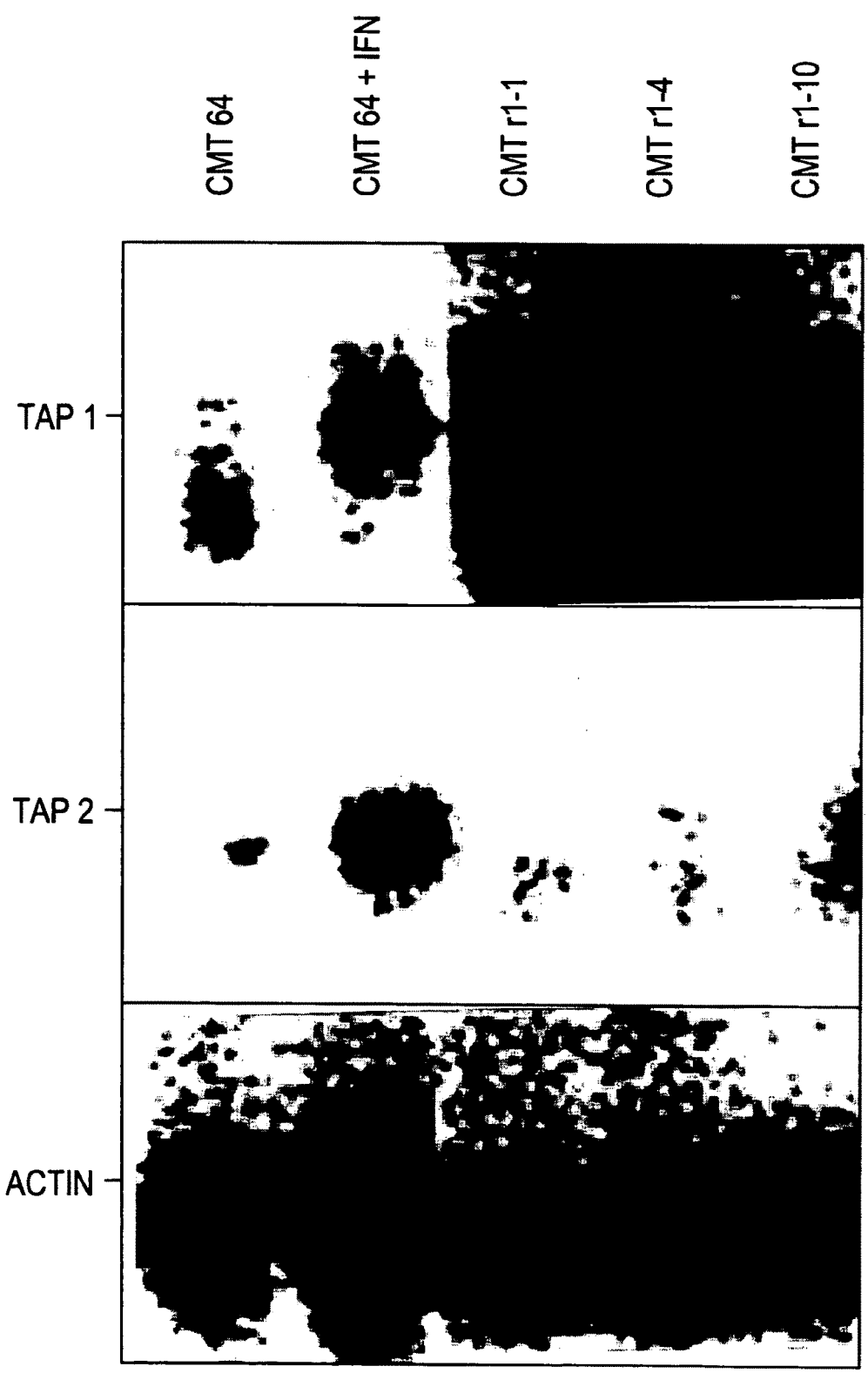
FIG. 10 shows TAP gene expression profiles of CMT.64 and CMT64/rl-4.

In order to investigate the ability of TAP-1 to function independently in peptide transport, the rat TAP-1 cDNA was introduced into the murine small lung carcinoma cell line CMT.64 which does not express endogenous TAP-1 or TAP-2 mRNA (FIG. 10). The endogenous TAP genes, as well as those coding for the putative proteasome components LMP2 and 7, are expressed only after IFN-γ treatment (FIG. 10). Positive transfectants were selected using the neophosphotransferase selection system and constitutive expression of the TAP-1 gene was confirmed by northern blotting.

In particular, transfection of CMT.64 cells with rat cDNA TAP-1 (in the pHb APr-1-neo expression vector as described in Powis, S. J. et al. Nature 354, 528-531 (1991)) was achieved by lipofection (Lipofectin, BRL) using 10 μg of DNA. Selection was in I mg/ml G418 (Gibco). Total RNA was isolated using guanidine isothiocyanate and electrophoresed on a 1% agarose gel containing 2.2M formaldehyde (10 μg/lane). Blotting and hybridisation with [$^{32}$P]-labelled cDNAs (TAP-1 and 2) or oligonucleotide (actin) were carried out as described herein.

Both TAP-1 and 2 mRNA transcripts were absent in uninduced CMT-64 cells but were detected in CMT.64 cells cultured in the presence of 200 units/ml of mouse recombinant IFN-γ for 48 hours (FIG. 10), CMT64/rl-4 expressed high levels of vector-derived TAP-1 mRNA but remained negative for TAP-2. Actin mRNA was used to demonstrate that equal amounts of RNA had been loaded.

Three high expressing clones were selected for subsequent experiments (FIG. 10). Three clones transfected with vector alone were also selected and used as controls in the subsequent experiments.

Example 10

TAP-1 Expression is Sufficient to Increase Levels of $K^b$ and at the Cell Surface of CMT.64 Cells CMT.64 cells also express virtually no surface MHC class I molecules, despite synthesis of both $D^b$ and $K^b$ heavy chains (Jefferies, W. A. et al., supra, 1993). To determine the influence of TAP-1 on surface class I expression, flow cytometry was carried out using antibodies against $D^b$ and $K^b$. In particular, the cells were incubated with or without primary antibody for 1 hour. All incubations were carried out at 4° C. After washing, the cells were incubated with fluorescein isothiocyanate-conjugated goat anti-mouse Ig antibody (20 mg/ml) for an additional hour. Following two rounds of washing, the cells were fixed in 1.5% paraformaldehyde. The fluorescent profiles were obtained by analysing 5,000 cells in a semi-logarithmic plot using a FACScan® programme.

Figure 11:
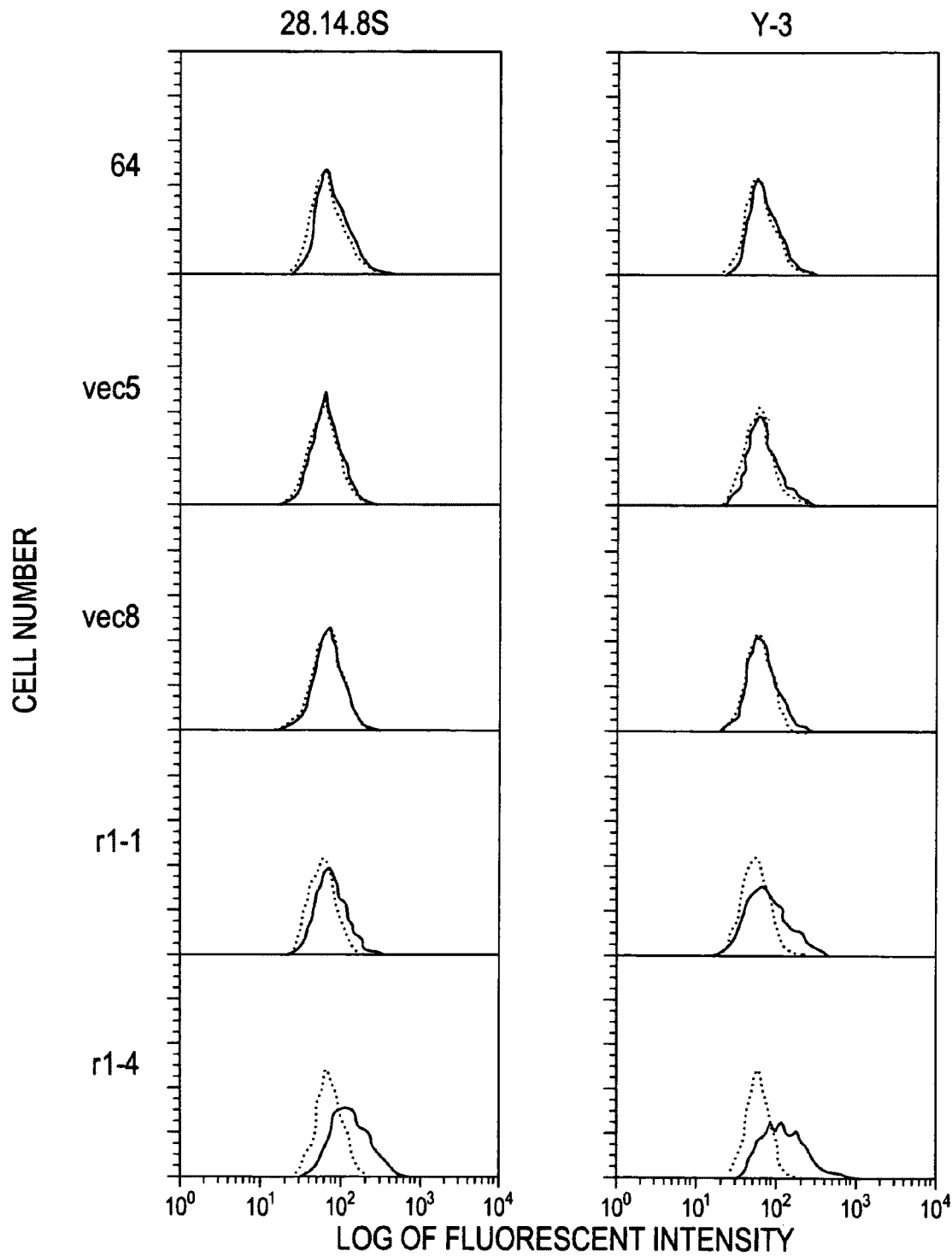
FIG. 11 shows flow cytometric analysis demonstrating that TAP-1 expression is sufficient to increase levels of $K^b$ and $D^b$ at the cell surface of CMT.64 cells.

Flow cytometric analysis demonstrated that TAP-1 expression was sufficient to increase levels of $K^b$ and $D^b$ at the cell surface of CMT.64 cells as shown in FIG. 11. The antibodies 28.14.8s and Y-3 recognise $D^b$ and $K^b$ respectively. In all panels the results obtained with the indicated primary antibody are shown by a solid line. The dotted line represents the values obtained in the absence of a primary antibody. The results shown are representative of three independent experiments.

For both antibodies tested there was a detectable increase in surface expression in the CMT-TAP-1 transfectants compared to CMT.64 and the vector controls, suggesting TAP-1 alone had delivered peptides to the site of MHC assembly, allowing stable complexes to be formed, transported and expressed at the cell surface. The amount of transferrin receptor expressed at the cell surface was unchanged by the transfection of TAP-1, indicating that this was not a general effect on plasma membrane proteins (data not shown). In contrast to other systems where it has not been possible to discount the involvement alternative mechanism of peptide transport (Hosken, N. A. & Bevan, M. J. *J. Exp. Med.* 175:719-729 1992; Esquivel, 5 F., Yewdell, J. & Bennink, J. *J. Exp. Med.* 175:163-168, 1992; Zweerink, H. J., et al. *J. Immunol.* 150: 1763-1771, 1993), these results clearly demonstrate the ability of TAP-1 to increase surface class I expression in the absence of TAP-2 in CMT.64 cells.

Example 11

Pulse-Chase Analysis of $K^b$ and $D^b$ Molecules from CMT.64 and TAP-1 Transfected CMT.64 Cells Intracellular transport of class I heavy chain to the cell surface is accompanied by processing to a higher molecular weight form by modification of the N-linked glycans during successive exposure to Golgi-specific enzymes. Pulse-chase experiments were therefore performed to determine if such processing was achieved in the CMT-TAP-1 transfectants, as predicted by the increase in surface expression of $K^b$ and $D^b$.

Pulse-chase and immunoprecipitation of $K^b$ and $D^b$ were performed using a 15 minute pulse with $^{35}$S-methionine (Amersham) and immunoprecipitated 28.14.8S (anti-$D^b$) and Y-3 (anti-$K^b$) monoclonal antibodies, following the methods described above. Samples were analysed by SDS-PAGE on 10-15% gels and treated with an amplifying solution. The autoradiogram was developed after 10 days.

Figure 12:
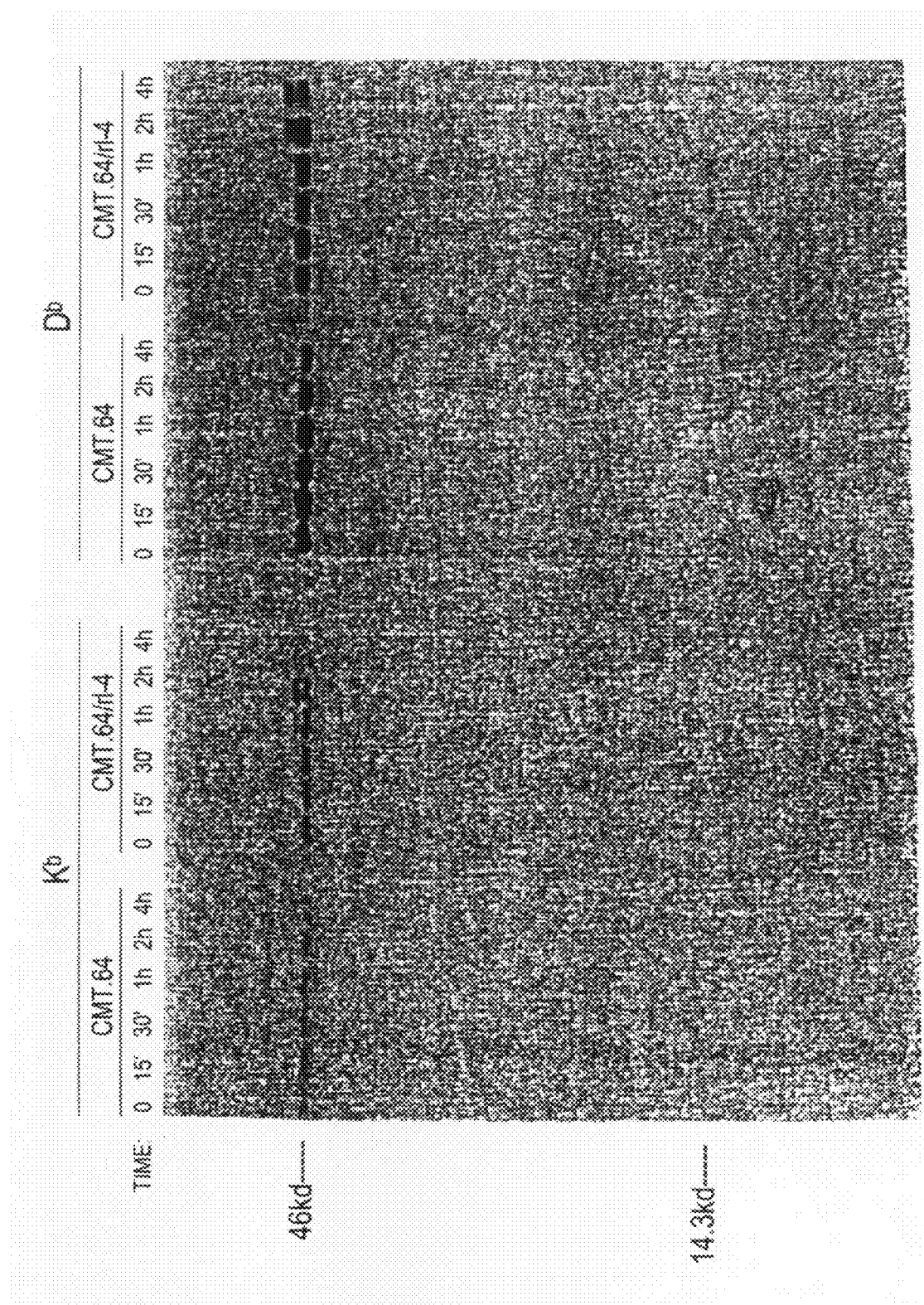
FIG. 12 shows pulse-chase analysis of $K^b$ and $D^b$ molecules from CMT.64 and TAP-1 transfected CMT.64 cells (CMT64/rl-4)

Transport of $K^b$ and $D^b$ molecules to the cell surface occurred in the TAP-1 transfected cells, as indicated by the increase in molecular weight of the heavy chain during oligosaccharide side chain processing (FIG. 12). In untransfected CMT.64 cells no processing was observed (FIG. 12), indicating retention within the endoplasmic reticulum or cis golgi. This was confirmed by sensitivity to endoglycosidase H (data not shown).

In summary, comparison between CMT.64 and CMT64/rl-4 revealed that the presence of TAP-1 was sufficient to allow the processing of $D^b$ and $K^b$ to occur (FIG. 12). In addition, it was determined by endoglycosidase H treatment that the higher molecular weight processed forms of Kb and Db were resistant to digestion (data not shown). These results further confirm the importance of TAP-1 for the transport and surface expression of MHC class I molecules in these cells.

Example 12

TAP-1 Transfected CMT.64 Cells Efficiently Present Antigen to VSV Specific CTL

In previous studies it was established that CMT.64 cells were unable to present VSV peptides to cytolytic T lymphocytes (CTL) unless pretreated with IFN-γ or incubated directly with a synthetic peptide derived from the VSV N protein (Jefferies, et al. *J. Immunol.*, 151:2974-2985, 1993). To examine the ability of TAP-1 expression to complement functional antigen processing and presentation, chromium release assays were carried out with VSV-specific CTL using CMT.64 and CMT-TAP-1 and CMT vector transfectants as targets.

In particular, CMT.64 cells (CMT) and CMT-TAP-1 transfectants were infected with VSV (MOI:2) for 8-10 hours, or treated with Influenza strain A/PR/8/34 for 48 hours (at 300 HA units for RMA, and 500 HA units for CMT.64 and their derivatives). Effector CTL populations were generated by infecting C57bl/6 mice with VSV in the foot pads and ears or 700 HA units of Influenza i.p, VSV CTL were derived from draining lymph nodes as collected on day 5 post immunization and single cell suspensions were cultured at 4×10$^6$ cells per ml for 3 days in the absence of any restimulation. Influenza CTL were derived from splenocytes, 4-5 weeks post-immunization, cultured in the presence of influenza infected stimulators for 6 days. The culture medium consisted of a 1:1 ratio of RPMI-1640 and NCTC-109 supplemented with 10% FBS, L-Glutamine, Pen/Strep, and 2 ME. Targets and effectors were mixed and incubated for 4 hours. Mock infected cells (+---) were used as negative controls. The results are expressed as % specific release, as detailed in Jefferies, W. A., Kolaitis, G. & Gabathuler, R. *J. Immunol.* 151, 2974-2985 (1993).

Figure 13:
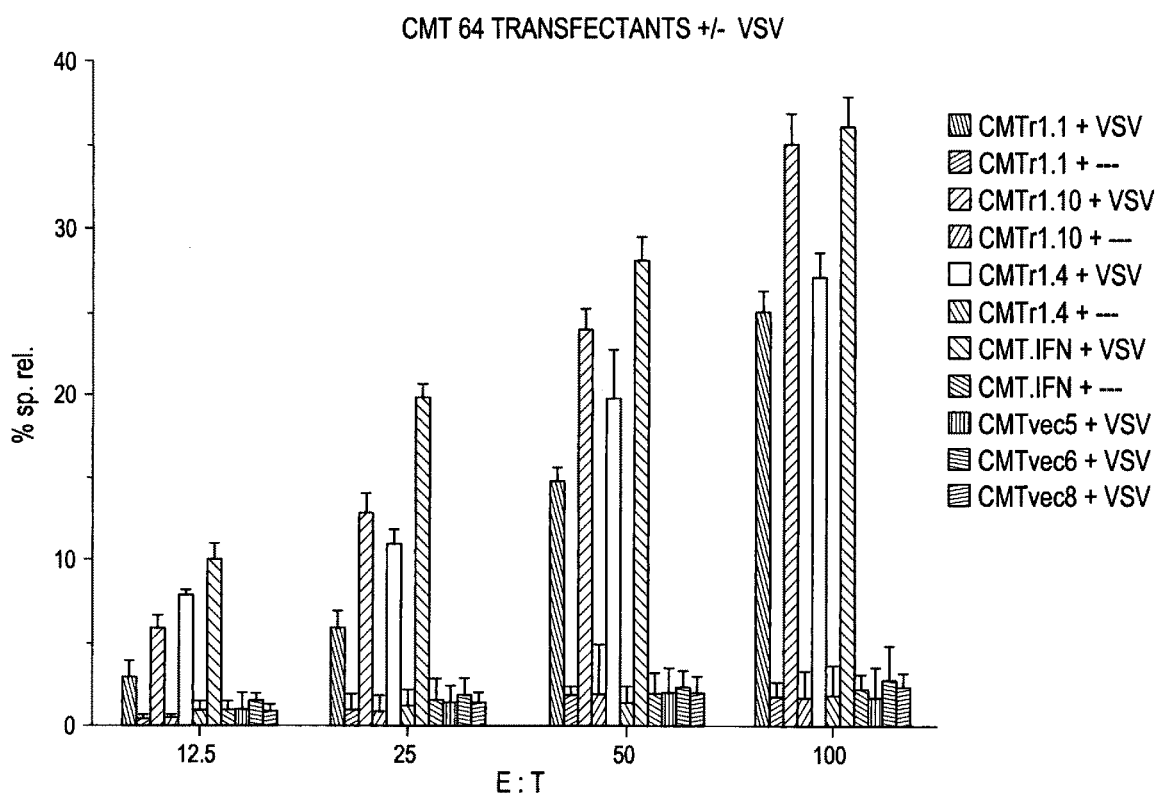
FIG. 13 is a histogram showing that TAP-1 transfected CMT.64 cells (CMT-rl.4) efficiently present antigen to VSV specific CTL.
Figure 17:
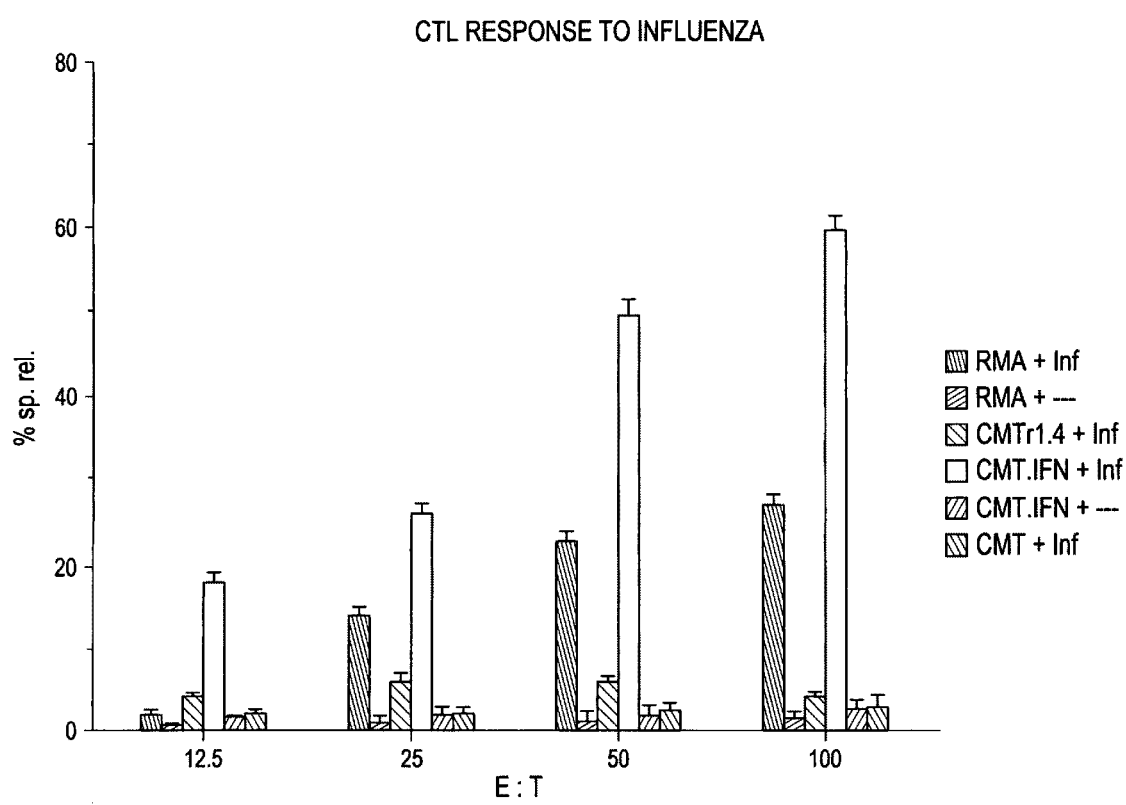
FIG. 17 is a histogram showing that RMA cells and CMT.64 cells treated with IFN-γ are recognized efficiently after influenza infection and CMT.64 cells transfected with the rat TAP-1 gene are not recognized.

The results illustrated in FIG. 13 show that TAP-1 transfected CMT.64 cells (clones CMT-r1.1, r1-4 and rl-10) efficiently present antigen to VSV specific CTL. Introduction of TAP-1 into CMT.64 cells restores antigen presentation following VSV infection. Wild type CMT.64 cells and vector transfected CMT cells infected with VSV are not recognised by CTL. FIG. 17 shows that Influenza virus is not presented to specific CTL by CMT-TAPI cells. CMT.64, RMA and CMTr1.4 cells were infected with Influenza virus and exposed to influenza-specific CTL. In this case however there was no recognition of the CMT-TAP-1 cells. Both positive controls. RMA and CMT.64+Inf, were efficiently lysed by the CTL.

Figure 14:
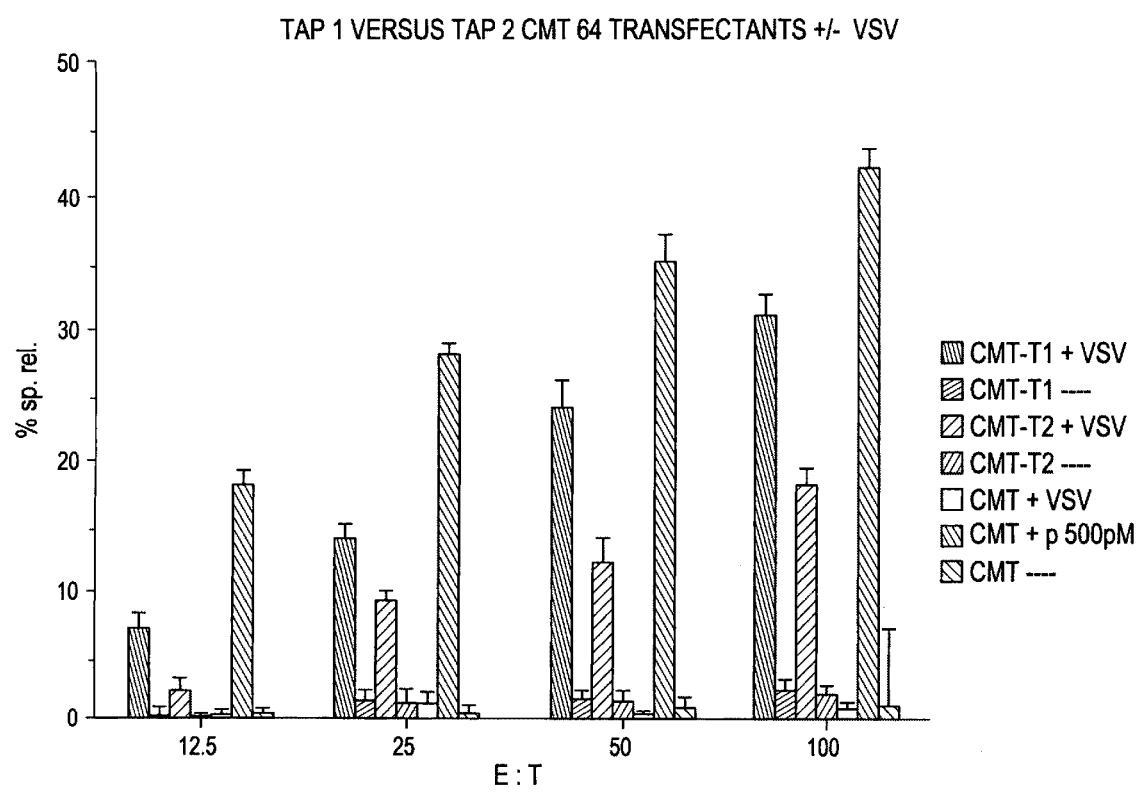
FIG. 14 is a histogram showing that TAP-1 and TAP-2 transfected CMT.64 cells efficiently present antigen to VSV specific CTL.
Figure 15:
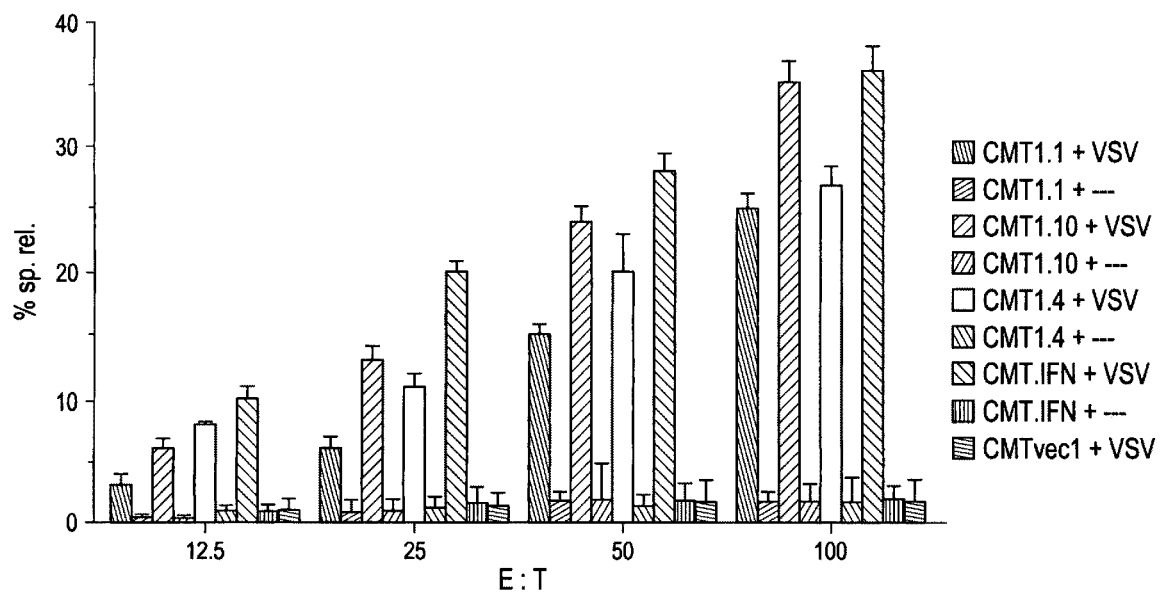
FIG. 15 is a histogram showing that various TAP-1 transfected clones efficiently present antigen to VSV specific CTL.

Additional experiments were carried out showing that VSV expression requires only the expression of the TAP-1 transporter, and that recognition of CMT.64 cells expressing the rat TAP-1 gene alone is almost as efficient 20 as cells expressing both transporters, TAP 1 and TAP-2. Expression of TAP-2 alone did not appear to be as efficient (FIG. 14). Different rat TAP-1 clones were also analyzed and confirmed the previous conclusions (FIG. 15).

Figure 16:
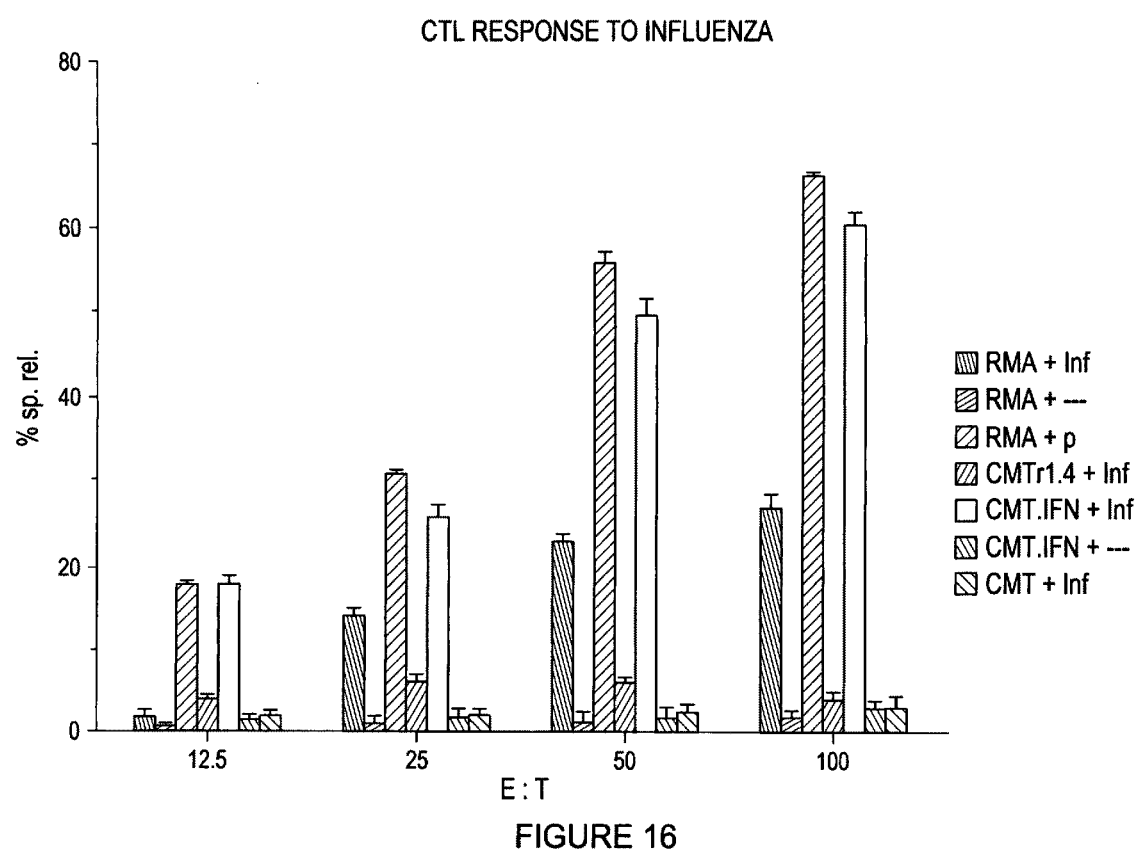
FIG. 16 is a histogram showing that RMA cells and CMT.64 cells treated with IFN-γ are recognized efficiently after influenza infection and CMT.64 cells transfected with the rat TAP-1 gene are not recognized.
Figure 18:
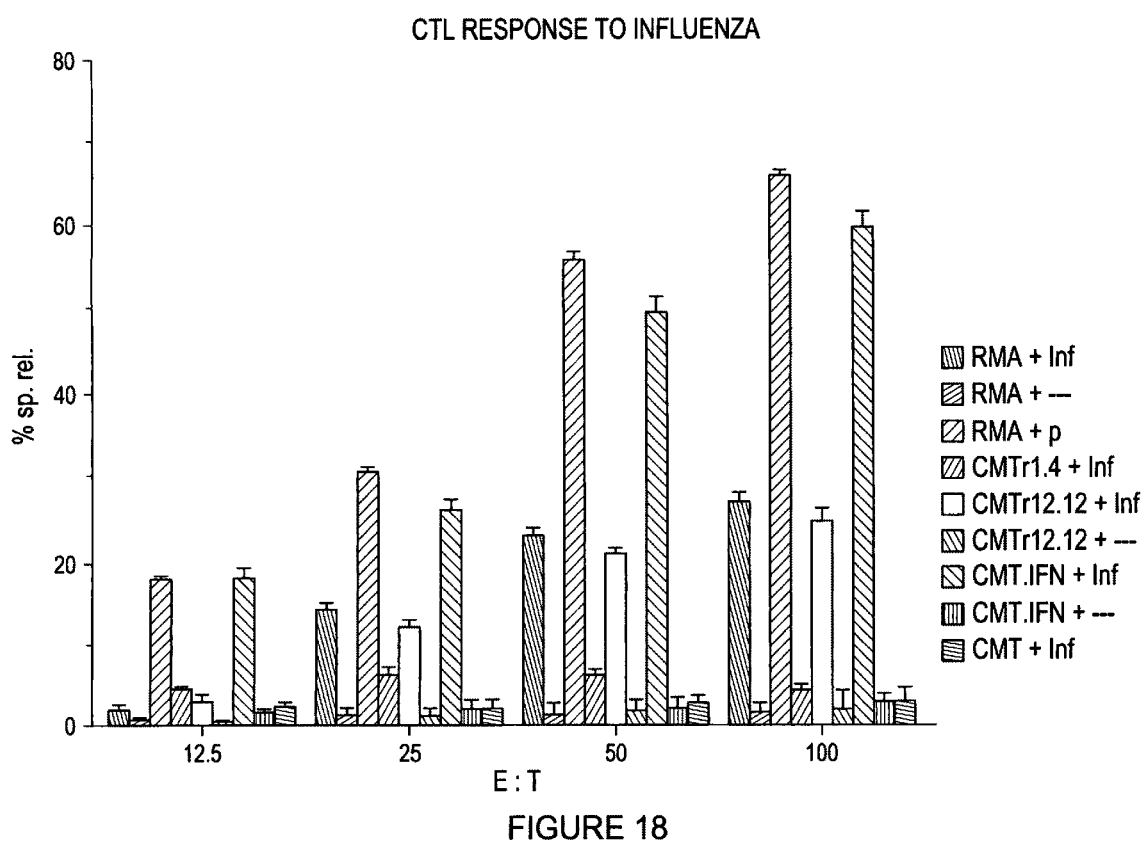
FIG. 18 is a histogram showing that RMA cells and CMT.64 cells treated with IFN-γ. CMT.64 cells transfected with both rat TAP genes are recognized after influenza virus infection.
Figure 19:
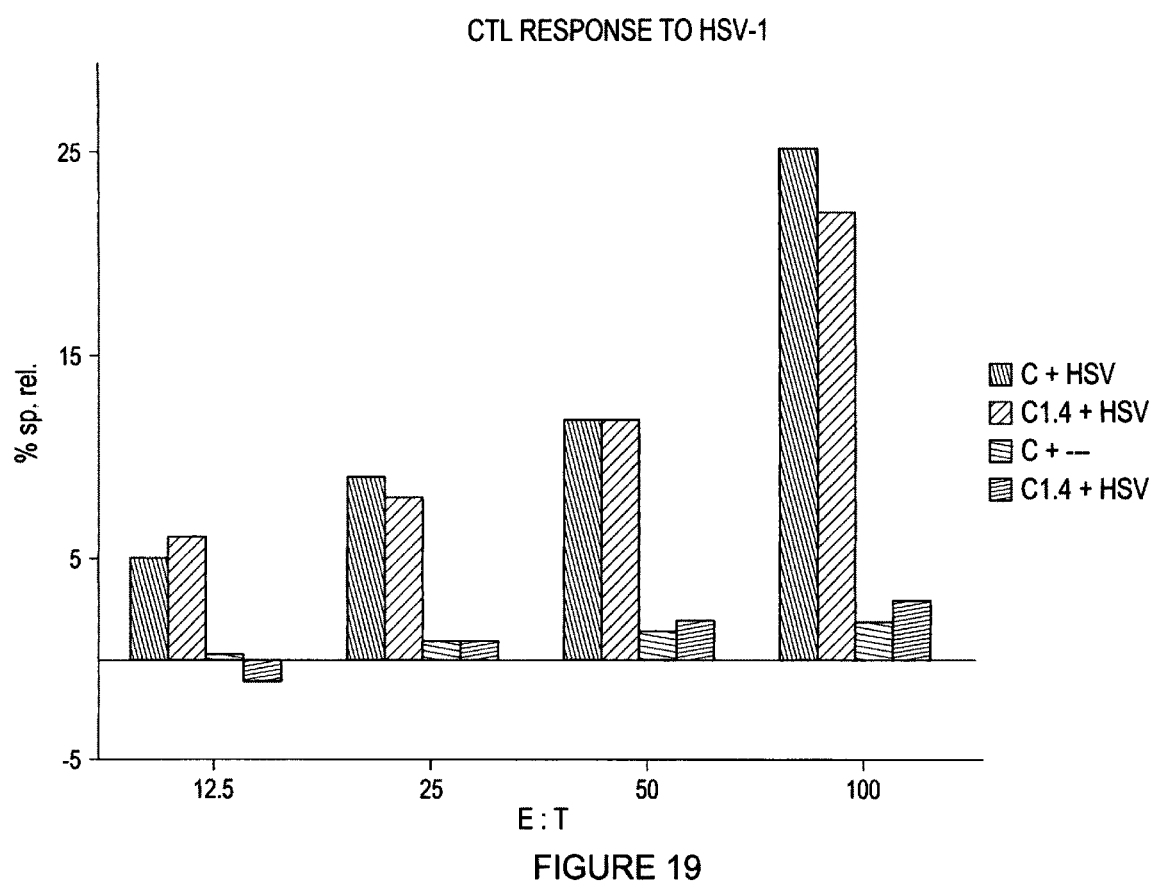
FIG. 19 is a histogram showing that HSV infected cells are recognized by specific CTL independently of the expression of the rat TAP-1 and/or TAP-2 transporter genes.

Influenza virus infected cells were found to be efficiently recognized only if both rat TAP genes are present (FIGS. 16 to 18). FIG. 16 shows that RMA cells and CMT.64 cells treated with IFN-γ are recognized efficiently after influenza infection. CMT.64 cells 30 transfected with the rat TAP-1 gene are not recognized. FIG. 17 shows the same results observed in a second independent experiment. FIG. 18 shows that in addition to RMA cells and CMT.64 cells treated with IFN-γ. CMT.64 cells transfected with both rat TAP genes are recognized after influenza virus infection. FIG. 19 shows that HSV infected cells are recognized by specific CTL independently of the expression of the rat TAP-1 and/or TAP-2 transporter genes.

These results provide evidence that an individual TAP-1 transporter molecule can restore the antigen presentation capability to a deficient cell in the absence of TAP-2. This finding correlates with the recent observation that the TAP-1 protein interacts with MHC class I heavy chain in cells that do not express TAP-2 (Suh, W-K., et al. *Science* 264:1322-1326, 1994). This calls into question the absolute requirement for heterodimer formation between the two putative transporter molecules and demonstrates that different forms of transporter complex are functional and mediate transport of distinct subsets of the antigenic peptide pool for assembly with MHC class I molecules.

Example 13

Effects of TAP on Tumor Survival

Mice were injected with CMT-64 cells or CMT.12.12 cells (a rat TAP-1 and TAP-2 transfected clone) ip at $2 \times 10^5$ and $5 \times 10^5$ cells per mouse. The cell lines were resuspended in PBS prior to inoculation into recipient mice. The results are shown in Table 2. One of the mice treated with $5 \times 10^5$ CMT.64 cells was sacrificed and an autopsy clearly revealed the presence of a solid tumor at the site of injection. Furthermore, all mesenteric lymph nodes were grossly enlarged.

Example 14

The following is an experimental approach for finding peptides translocated in the ER by TAP-1 transporters, TAP-2 transporters and TAP1-TAP-2 transporters.
1. Use of cell lines expressing TAP-1. TAP-2 and TAP-1 TAP-2 transporters; for example CMT.64 cells transfected with cDNA from TAP-1 and TAP-2, CMT.64, CMT.14, CMT.2-10, CMT.12-12.
2. Subcellular fractionation of these cells.
3. Isolation of the ER (endoplasmic reticulum).
4. Extraction of the peptides from the ER in 0.1% TFA.
5. Gel filtration.
6. Reverse-Phase HPLC.
7. Fractions can be collected and tested for CTL sensitization or for radioactivity if cells were labelled.
8. Finally, sequenced for amino acid.

Comparison of HPLC profile from different cell lines expressing different TAP transporters will provide information about peptide transport dependency on TAP molecules. Peaks of peptide can be isolated and analyzed. Sequencing of the peptides will provide information on the motif necessary for transport using TAP-1 alone, TAP-2 alone or TAP-1 and TAP-2 molecules. The protocol for peptides analysis and sequencing is standard and described in Rammensee papers and in Engelhard's papers.

Example 16

Anti-Sense Knockout in RMA-S Cells

This preliminary experiment was carried out on bulk selected populations of cells. The construct used was the same pHβA-neo that all the MTP 1 and 2 clones were obtained with as described above. In this study the MTP1 cDNA insert was cut out and it was replaced with a sequence in the opposite orientation. RMA-S cells only have TAP-1 not TAP-2, so only the MTP1 antisense was used. The data below are from single-colour FACS analysis, the numbers are linear (5000 events counted/sample). The 28.14.8s antibody is specific for $D^b$, and the Y-3 antibody is specific for $K^b$. The antisense construct is designated RMA-S.ptml.

| CELL | ANTIBODY | MEAN FLUORESCENCE |
| --- | --- | --- |
| RMA-S | — | 56.6 |
| RMA-S | 28.14.8s | 129.9 |
| RMA-S | Y-3 | 222.2 |
| RMA-S.ptml | — | 53.4 |
| RMA-S.ptml | 28.14.85 | 96.7 |
| RMA-S.ptml | Y-3 | 148.8 |

Example 17

Effect of TAP-1 and TAP-2 on Survival of Mice Injected with Tumor Cells

The survival of syngeneic C57BL/6 and control allogeneic Balb/C mice injected with very high doses of CMT.64 cells (from C57BL/6 mice) or CMT.12.12 cells (CMT.64 cells transfected with TAP-1 and TAP-2) was investigated as follows.

Figure 20:
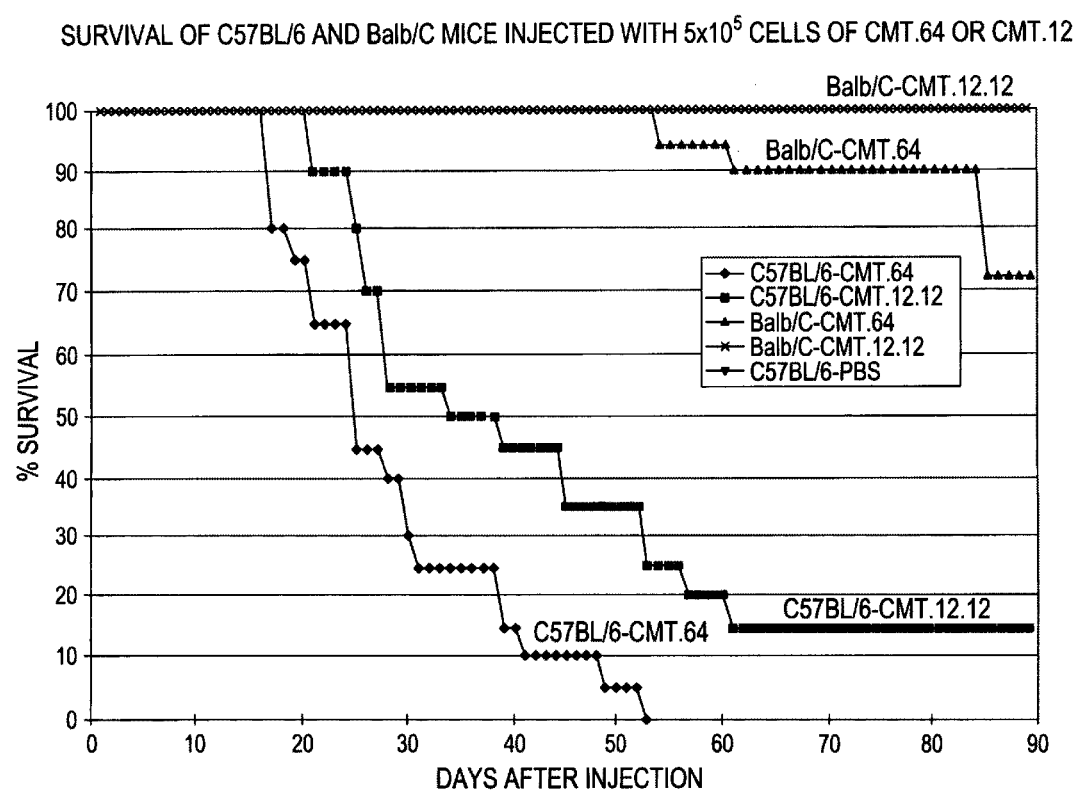
FIG. 20 is a graph showing survival of C57Bl/6 and Balb/C mice injected with 5×10⁵ CMT.64 or CMT.12.12 cells.

$5 \times 10^5$ CMT.64 or CMT.12-12 cells were injected into the mice intraperitoneally and the mice were followed for 90 days. Mice were autopsied after death or after 90 days. Survival of the mice is shown in FIG. 20. Results of the autopsies are summarized in Table 3. All of the syngeneic C57BL/6 mice injected with CMT.64 cells were dead before 60 days. These mice were found to have invasive generalized metastasized tumors throughout the body, and exhibited ruptured organs and/or perforated intestines with excessive fluid in the peritoneal cavity. This was classed as type B pathology.

Approximately 20% of the syngeneic mice injected with CMT.12.12 cells were alive at 60 days and 3 out of 20 were alive at 90 days. Seventeen of these mice out of a total 20 had type B pathology two had no apparent pathology and one had type A pathology, described below.

Approximately 70% of the allogeneic control mice injected with CMT.64 cells were alive at 90 days exhibiting no significant pathology. The few mice which did exhibit any pathology had only small tumors (4-15 mm) at the site of the injection. This was classed as type A pathology. 100% of the allogeneic mice injected with CMT.12.12 cells were alive at 90 days, exhibiting no pathology.

The results show that syngeneic mice injected with CMT.12.12 cells survived longer than those transfected with CMT.64 cells, probably due to improved MHC Class I antigen presentation and recognition by the host immune system. The syngeneic mice transfected with CMT.12.12 surviving at 90 days showed no or little pathology.

Example 18

Materials and Methods

Animals

The mouse strains C57BL/6 (H-$2^b$), and Balb/C(H-$2^d$). were obtained from Jackson Laboratories. The mice were maintained according to the guidelines of the Canadian Council on Animal Care. The mice used in the experiments were between 6 and 12 weeks of age.

Plasmids and Bacterial Strains

The plasmid pJS5 (a generous gift from Dr. B. Moss, NIH, Bethesda, USA) was a shuttle vector used first in bacteria to clone in the gene for rTAP1, or the minigene for amino acids 52-59 of the VSV N protein (VSV NP). The minigene included a methionine start site in front of the 8 amino acid coding sequence, as well as a translational stop codon at the end. DNA sequencing verified that the correct sequence and orientation of the minigene in pJS5 were correct. The pJS5 plasmid containing the cloned gene was then transfected into mammalian cells for homologous recombination with wild type Vaccinia Virus (VV). The pJS5 plasmid contains an *E. coli* ampicillin resistance gene for plasmid selection in bacteria, as well as an *E. coli* guanine phosphoribosyl transferase (gpt) resistance gene for selection of recombinant VV (rVV) in cells. pJS5 contains two synthetic W promoters in front of a multiple cloning site (MCS) where either rTAP1 or VSV NP were cloned into, giving the plasmid pJS5-VSV NP. The entire section including the two promoters. MCS, and gpt resistance gene is flanked by the 5' end of a thymidine kinase (tk) gene downstream, and the 3' end of the tk gene upstream, for homologous recombination into the tk gene of W. The plasmids were amplified in the *E. coli* strain DH5aF' grown in Luria-Bertani (LB) medium or on LB agarose plates containing 50 μg/ml ampicillin.

Oligonucleotides

The two complementary oligonucleotides used to make the minigene for VSV N52-59 were synthesized using an Applied Biosystems automated DNA synthesizer model 380A at the NAPS unit (U.B.C., Vancouver, Canada). The oligonucleotides and the amino acids they coded for were as follows:

```
                                                        (SEQ ID NO: 1)
SacI overhang                                       NheI overhang
1)      3'-TCGAG-TAC-TCT-CCT-ATA-CAG-ATG-GTT-CCG-GAG-ACT-CGATC-P (SEQ ID NO: 2)
2)      5'-P-C-ATG-AGA-GGA-TAT-GTC-TAC-CAA-GGC-CTC-TGA-G (SEQ ID NO: 3)
Peptide start-arg-gly-tyr-val-tyr-gly-gly-leu-stop

P = PO3
```

After purification on Pharmacia nick spin columns, equimolar amounts of each oligonucleotide were annealed in ligase buffer (Boehringer Mannheim) for 2 minutes at 95° C. before cooling slowly to room temperature. The oligonucleotides were designed to provide overhangs corresponding to cleaved restriction sites for direct ligation into the NheI and SacI cut pJS5 vector.

Viruses

The rVV were made by transfecting the plasmids into the VV infected B-SC-1 cell line where the wild type VV and transfected plasmids underwent homologous recombination at the thymidine kinase (tk) gene of VV. Once the rVV were isolated by selection with XMH, and recombination was verified by Southern blotting, large rVV cultures were grown for later purification of the rVV on sucrose gradients. Purification of the rVV from the cellular debris was considered essential in order to eliminate any immunological responses by the mice to cellular material from Hela. CV-1, or BS-C-1 cells. Crude cell viral lysates were used for infecting cells in vitro. VSV stocks were grown on Vero cells in DMEM medium containing 10% FBS, P/S, and aliquots of the culture supernatant kept at −80° C. according to (ref.). Vaccinia virus (VV) stocks were grown on CV-1 cells for small stocks and Hela S3 cells for the larger stocks. CV-1 cells were used to titre the VV stocks. The infections of the cell lines by VV were generally carried out at a MOI of 5-10. The VV was first trypsinized with 0.1 volume of 2.5 mg/ml trypsin (1:250: Difco Laboratories Inc., Detroit, Mich.) at 37° C. for 30 minutes, vortexing every 10 minutes, to break up the aggregated VV before being diluted in a small volume of DMEM media containing 2% FBS. This viral inoculum was added to cells previously washed with PBS and allowed to incubate for 60-90 minutes at 37° C. in a humidified, 5% $CO_2$/95% air environment. Then, complete medium containing 7-10% HI FBS was added and the cells allowed to grow until needed for an assay, or until the culture demonstrated 95% cytopathicity. When VV infected cells were required for an assay the infection was generally performed for 4-24 hours before the cells were removed with 0.25% trypsin, or versene plus 0.05% trypsin.

Recombinant VV was constructed by homologous recombination of the wild type VV WR strain by infecting CV-1 cells transfected with the plasmids pJS5 or pJS5-VSVNP according to previously described protocols (Macket et al., 1989).

Generation of Effector Cell Populations

Virus-specific CTL populations were generated by infecting mice intraperitoneally (ip) with $10^7$ tissue culture infection dose (TCID) units of VSV or at the suggested plaque forming units (pfu) for VV-VSV NP and VV-TAP. CTL were collected on day 5 post immunization from the cervical lymph nodes (LN), or spleen and cultured in RPMI-1640 medium containing 10% HI HyClone FBS (Gibco), 20 mM Hepes, 2 mM L-glutamine, 0.1 mM essential amino acids, 1 mM sodium pyruvate, 50 mM b-mercaptoethanol (b-ME), and penicillin/streptomycin (henceforth referred to as RPMI complete medium). The LN cell suspensions were cultured at $4 \times 10^6$ cells/ml for 3 to 5 days in the absence of stimulation before being used in a CTL assay, whereas the splenocyte suspension was cultured for 7 days with peptide stimulation. Bulk populations of VSV-specific CTL were maintained by weekly restimulation with 1 μM VSV N peptide (amino acids 52-59) plus pulsed irradiated (2200 rads) stimulator splenocytes. Irradiated stimulator cells and CTL were incubated together at a ratio of 4:1 in RPMI complete medium containing 20 units/ml hIL-2. Seven days later, this bulk population was used in a CTL assay.

Cytotoxicity Assays

Target cells for the CTL assays were loaded with $^{51}Cr$ by incubating $10^6$ cells with 100 μCi of $^{51}Cr$ (as sodium chromate. Amersham) in 250 μl of CTL medium (RPMI-1640 containing 10% HI FBS, 20 mM Hepes) for 1 hour. Following three washes with RPMI, 2% FBS, the target cells were incubated with the effector cells at the indicated ratios for 4 hours. 100 μl of supernatant from each well was collected and the $^{51}Cr$ release was measured by a compugamma computer (LKB Instruments). The specific $^{51}Cr$ release was calculated as follows: [(experimental−media control)/(total−media control)]×100%. The total release was obtained by lysis of the cells with a 5% Triton-X 100 (BOH) solution.

Results and Discussion

The TAP complex is responsible for maintaining a supply of peptides to MHC class I molecules and it has been suggested that the supply of peptides may be a limiting factor in the number of stable MHC class I on the cell surface (SUH. W. K., et al., *Science* 264:1322; Ortmann, B. at al. *Nature* 368: 864). TAP retains 'empty' MHC class I in the ER until it binds peptides. If increasing the expression of TAP to a cell could increase the number of MHC class I molecules on the cell surface presenting immunogenic peptides, then perhaps the inclusion of genes encoding TAP, and a gene encoding a cytotoxic epitope in VV vectors could increase the specific antigen presentation.

A subunit vaccine was required in order to investigate whether the presence of TAP could enhance antigen presentation in vivo, thus a model subunit vaccine (VV-NP) was created using VV as a carrier, and the immunodominant cytotoxic epitope (amino acids 52-59) of the VSV N peptide. The VSV N peptide was chosen because it is known to bind to H-2K$^b$ and elicit a specific CD8+ CTL response (van Bleek, G. M. et al. *Nature* 348:213; Fremont, D. H. et al. *Science* 257:919; Kundig, T. M. et al. *Proc. Natl. Acad. Sc. USA* 89:7757) and is the dominant immunogenic epitope in VSV. More than 80% of CTL are directed against this epitope (Rotzschke t al. *Nature* 348:252; Byrne et al., *J. Virol.* 51:682; Harty, J. T. et. al. *J. Exp. Med.* 175:1531; Feltkamp, M. C. W., et al. *Mol. Immunol.* 31:1391; Weidt, G. et al. *J. Immunol.* 153:2554). A min(gene encoding the cytotoxic epitope of the VSV N protein, amino acids 52-59, was created using oligonucleotides which were inserted into the pJS5 plasmid to create pJS5-VSV/NP. Once the pJS5-VSV/NP plasmid was constructed it was used to create the rVV containing the VSV N52-59 peptide (VV-NP). A rVV vector only control (VV-pJS5) was also constructed.

Figure 21A:
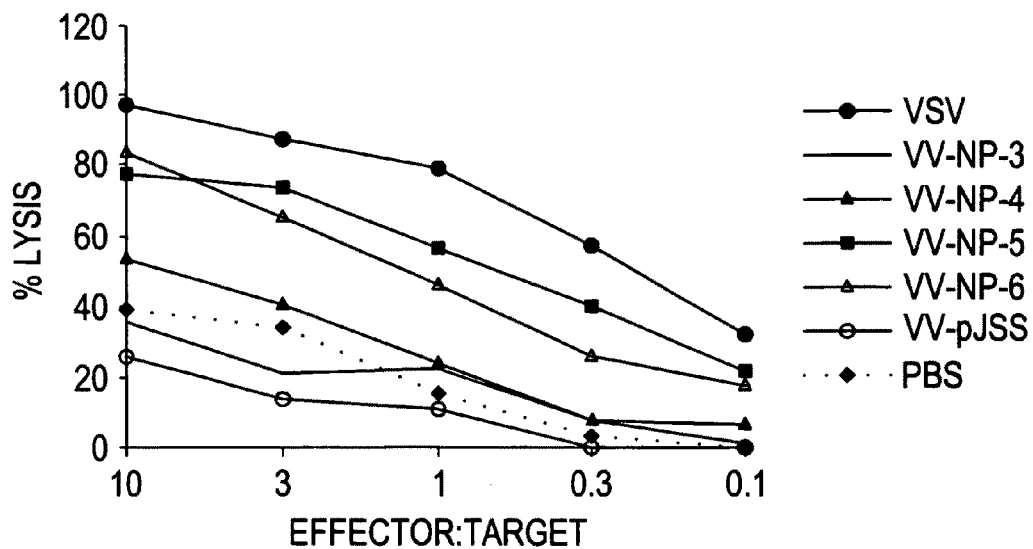
FIGS. 21A and B are graphs showing the immune response to varying VV-NP dosage. Splenocytes from immunized C57Bl/6 mice were tested for their ability to recognize VSV infected targets in a 4 hour $^{51}Cr$ release CTL assay. The mice were injected ip. with either VSV (3×10⁷ TCID50), or VV-NP at 10³ (3), 10⁴ (4), 10⁵ (5), 10⁵ (6) pfu, or VV-pJS5 (10⁶ pfu), or PBS. The splenocytes were tested for their ability to recognize either A) RMA targets infected with VSV (MOI=10 for 8 hours) or B) uninfected RMA targets.
Figure 21B:
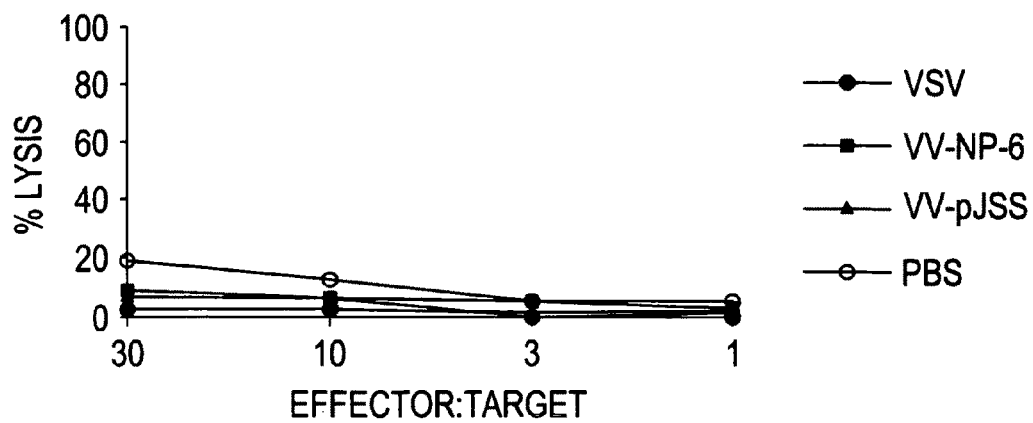

The VV-NP was tested in vivo to see if it could elicit an anti-VSV response. As seen in the CTL assay in FIG. 21 the splenocytes from mice injected with VV-NP were able to lyse RMA targets infected with VSV but not uninfected RMA targets. The minimum amount of VV-NP required to elicit an immune response in C57BL/6 mice was $10^4$ plaque forming units (pfu) and the maximum immune response was achieved at $10^5$-$10^6$ pfu. At a higher titer of $10^8$ pfu ($10^7$ and $10^8$ not shown) the response decreased and VV levels above $10^8$ pfu were lethal. There does not appear to be any significant difference in the response elicited by doses of VV-NP between $10^5$ and $10^7$ pfu, so the median dose of $10^6$ pfu was chosen for the remaining assays.

Figure 22A:
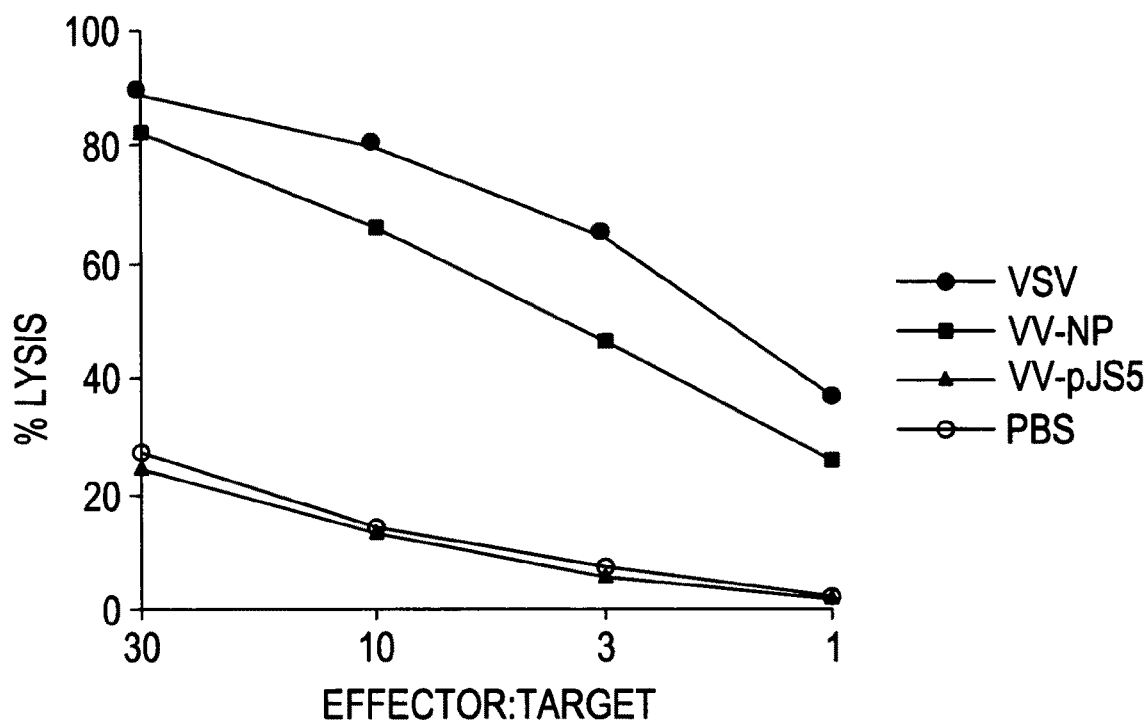
FIGS. 22A and B are graphs showing the specificity of splenocytes from VV-NP immunized mice. Splenocytes from immunized { }57Bl/6 mice were tested for their ability to recognize targets in a 4 hour $^{51}Cr$ release assay. The mice were injected ip. with either VSV (3×10⁷ TCID50), or VV-NP (10⁶ pfu), or VV-pJS5 (10⁶ pfu), or PBS. They were tested for their ability to recognize either A) RMA targets pulsed for one hour with VSV N peptide or B) RMA targets infected with VV-pJS5 (MOI=10 for 8 hours)
Figure 22B:
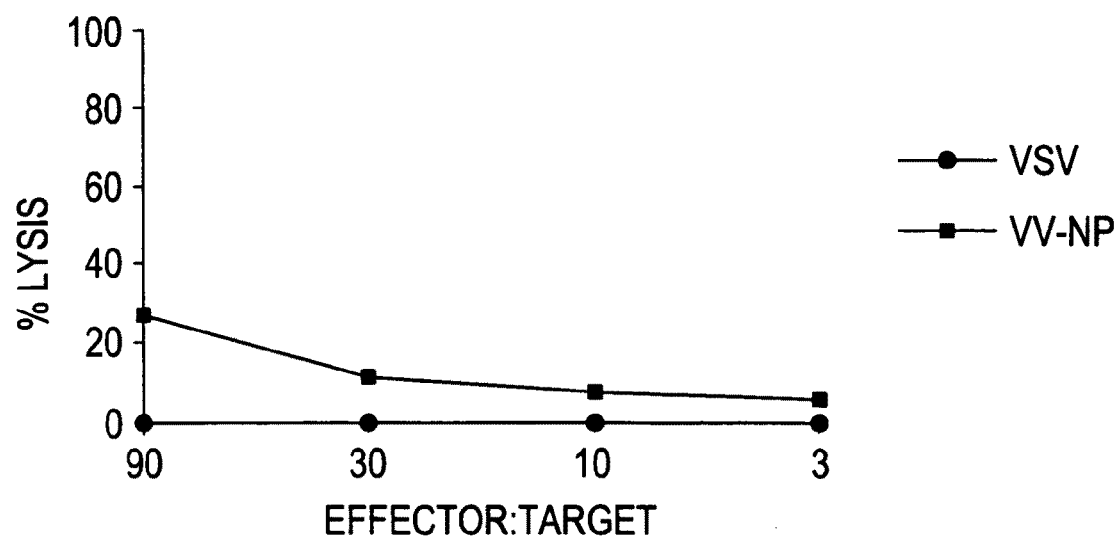

The splenocytes in the mice injected with VV-NP include cytotoxic lymphocytes that were specific for VSV (FIG. 22). It was also determined in a CTL assay with VSV N52-59 pulsed targets, that the immune response elicited in mice injected with VV-NP included CTLs that were specific for the VSV N52-59 cytotoxic epitope (FIG. 22). The mice injected with the control vector VV-pJS5 did not contain VSV specific lymphocytes as they gave the same low response seen in mice injected with PBS. Splenocytes from the VV-NP primed mice were also able to recognize VV infected RMA targets but to a much lesser degree than they recognized the VSV N peptide epitope.

As the TAP complex is responsible for transporting peptides across the ER lumen and for binding to MHC class I, a functional assay for the TAP activity involves the restoration of antigen presentation in a TAP deficient cell. In order to demonstrate this, a CTL assay specific for the VSV N52-59 cytotoxic epitope was used to verify that the TAP 1 and 2 produced by VV are functional (FIG. 22).

Figures 23A, 23B:
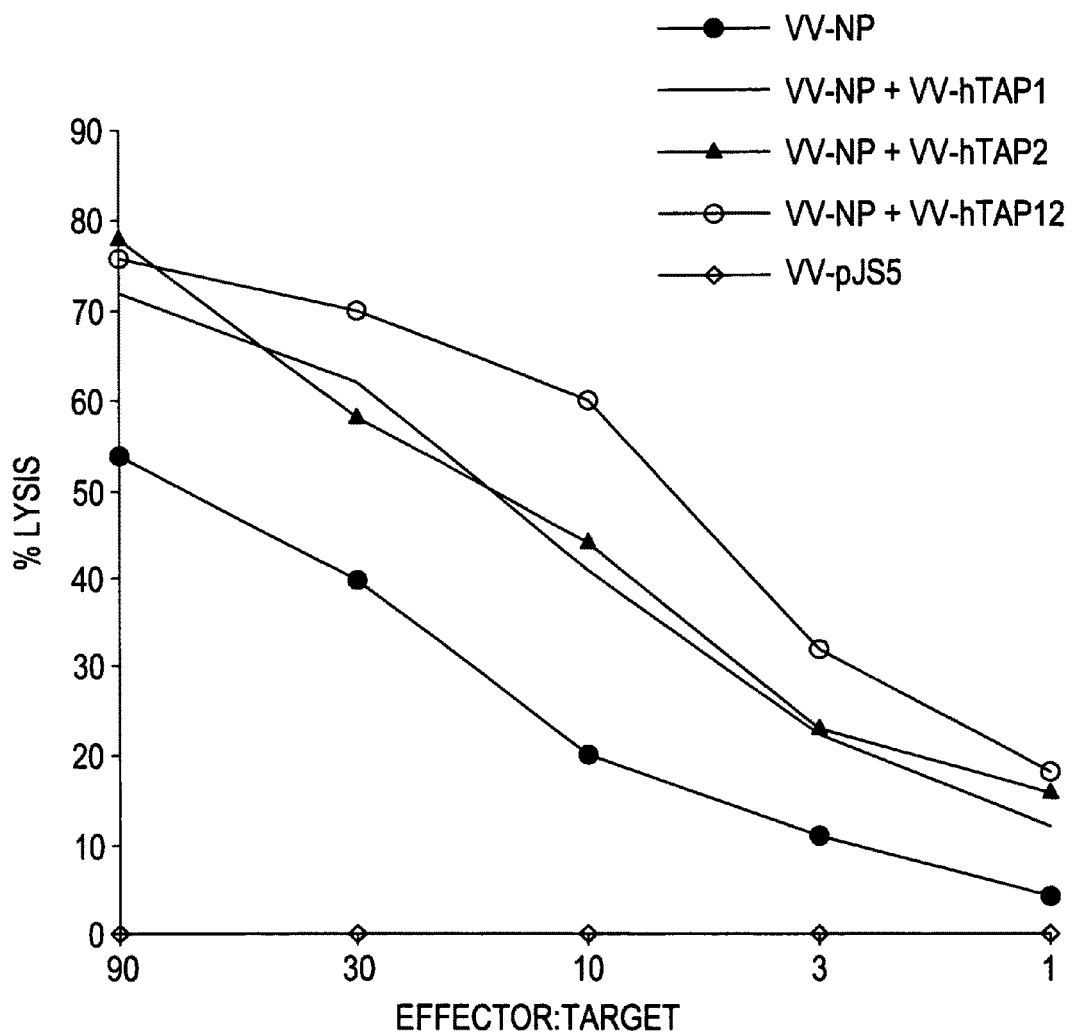
FIG. 23 is a graph showing the effect of TAP on VV-NP immunization. (A) Splenocytes from C57Bl/6 mice immunized ip. with VV-NP (106 pfu) with or without VV-hTAP ($5 \times 10^6$ pfu) were tested for their ability to recognize VSV infected RMA targets (MOI=10 for 9 hours) in a 4 hour $^{51}$Cr release assay. (B) Frequencies of VSV specific CTL in splenocytes from mice injected with VV-NP alone or with VV-hTAP12 were determined in a limiting dilution analysis.
Figure 24:
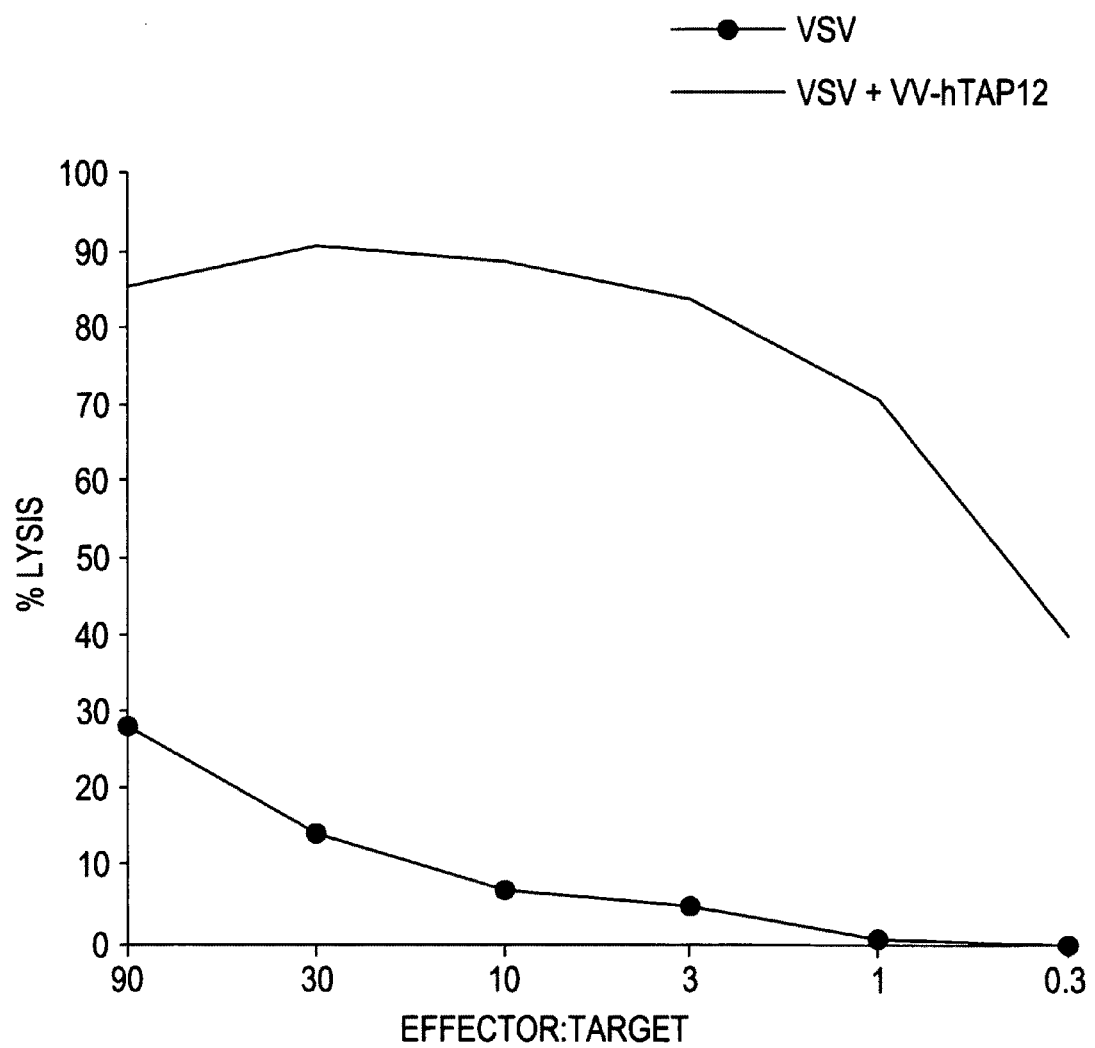
FIG. 24 is a graph showing the effect of TAP on a low dose immunization Splenocytes from C57BI/6 mice were tested against VSV NP (1 mM) pulsed RMA targets in a standard 4 hour $^{51}$Cr release assay. The mice were immunized with VSV ($2.7 \times 10^3$ TCID$_{50}$) alone or with VV-hTAP12 ($1.35 \times 10^4$ pfu)
Figure 25:
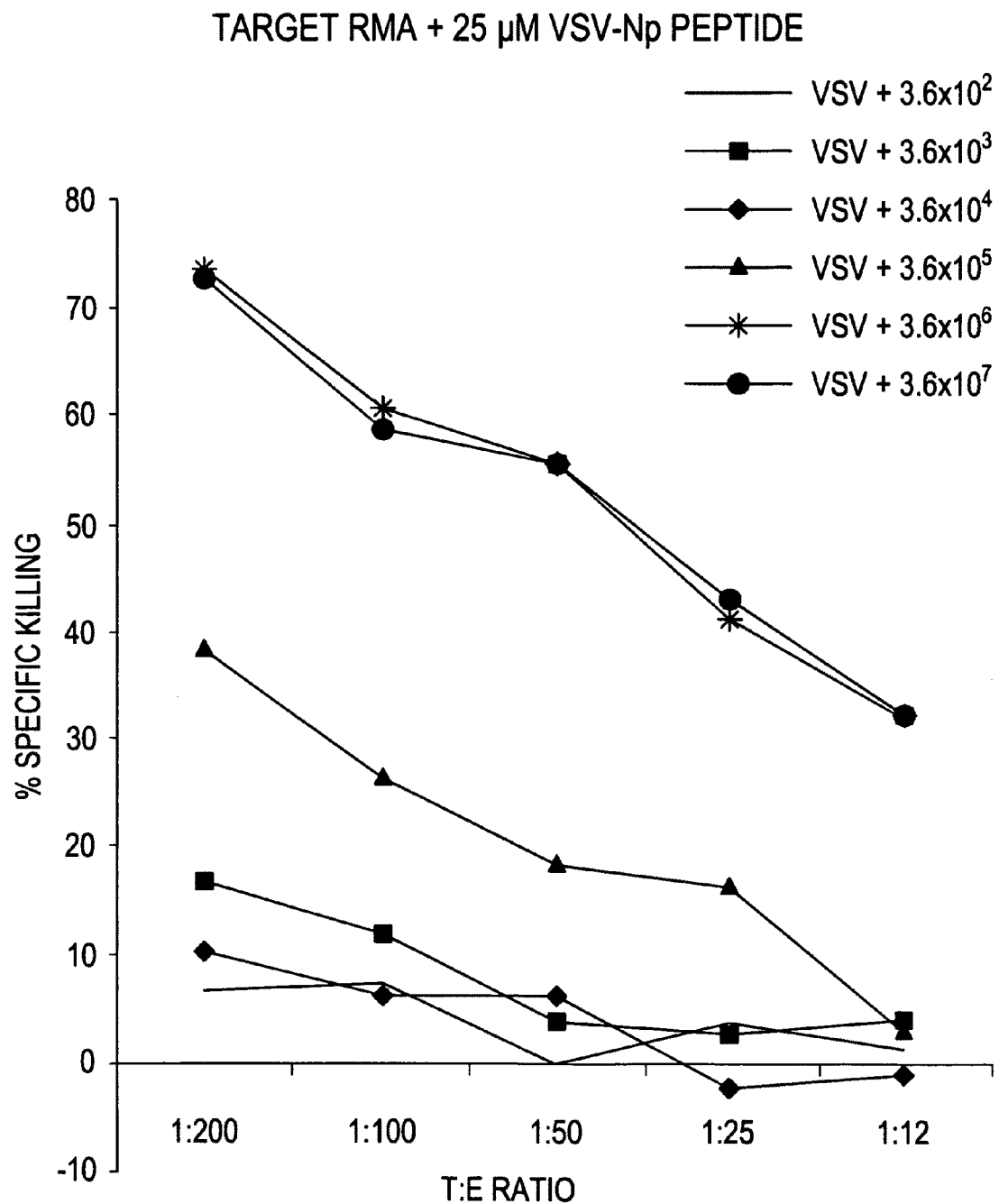
FIG. 25 is a graph showing the VSV-specific primary CTL generation in VSV-infected mice is viral dose-dependent. The immunized splenocytes derived from the mice injected with the indicated VSV TCID50 doses were tested of their cytotoxic activity by using VSV-Np peptide-pulsed RMA cells as target. A standard 4-h 51Cr release assay was performed.
Figure 26:
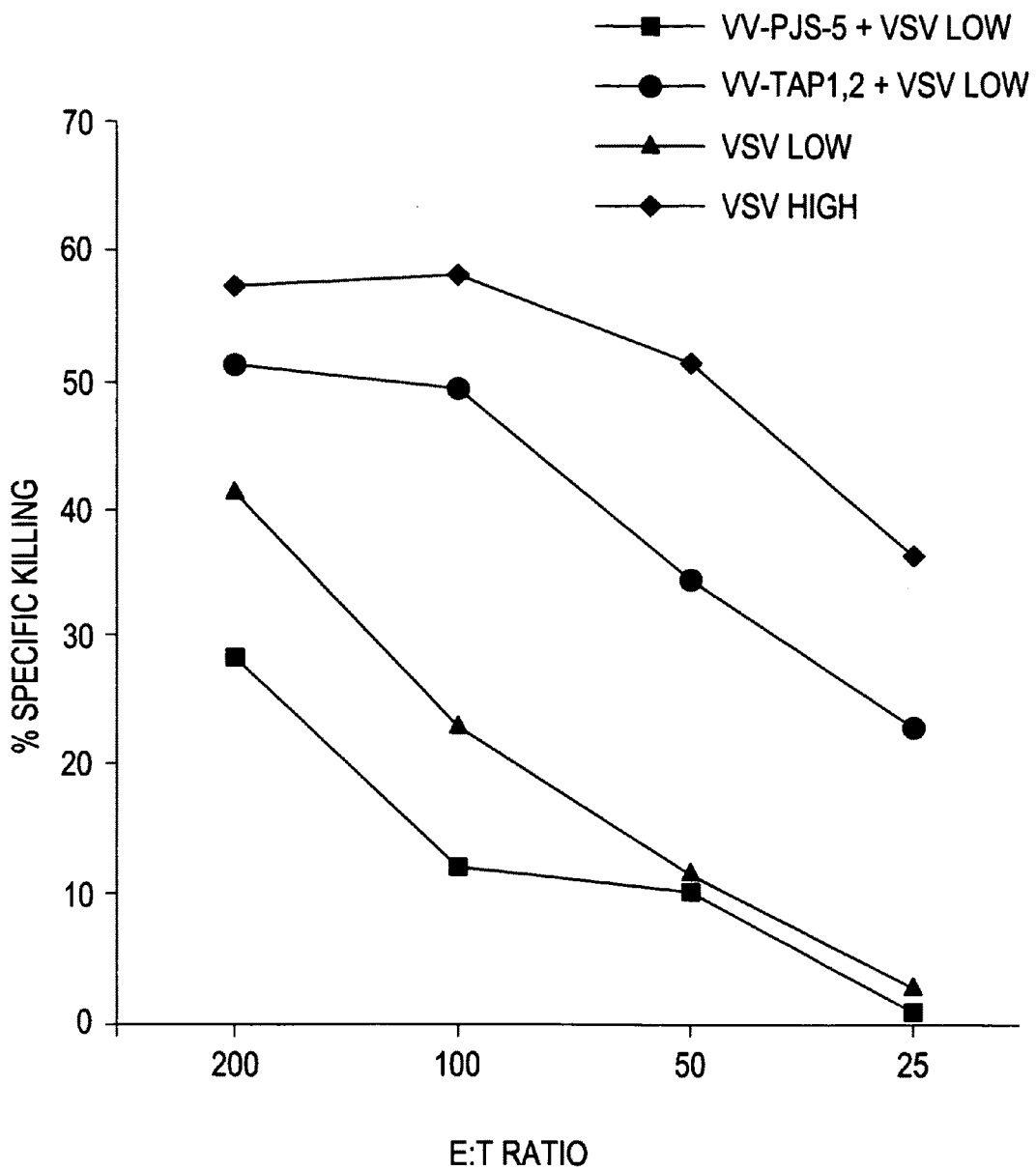
FIG. 26 is a graph showing that TAP heterodimer enhances the VSV-specific primary CTL response. The immunized splenocytes derived from the mice injected either VSV alone or VSV plus VV carrying with or without human TAP 1 and 2 genes were tested for their cytotoxic activity by using VSV-Np peptide-pulsed RMA cells as target. A standard 4-h 51Cr release assay was performed. Each legend is shown as following, VV-PJS-5+VSV low—$3 \times 10^4$ (PFU) VV alone+$3.6 \times 10^4$ (TCID50) VSV, VV-TAP1,2+VSV low—$3 \times 10^4$ (PFU) VV carrying human TAP 1 and 2+$3.6 \times 10^4$ (TCID50) VSV, VSV low $3.6 \times 10^4$ (TCID50) VSV and VSV high—$1.5 \times 10^7$ (TCID50)
Figure 27:
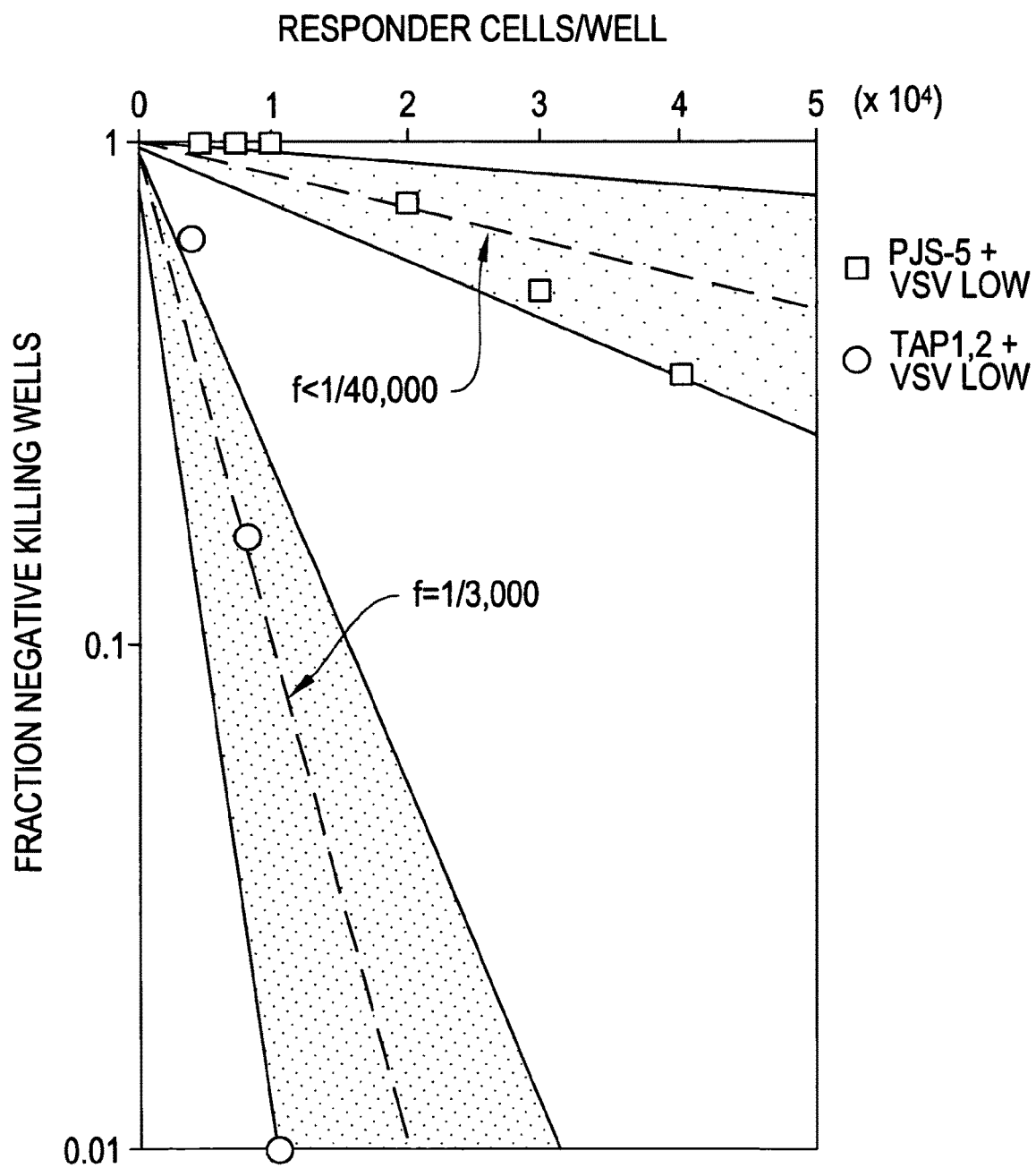
FIG. 27 is a graph showing VSV-Np epitope specific CTLp frequency was tremendously enhanced by introducing TAP 1 and 2 genes into VSV-immunized mouse. The immunized splenocytes from the mice injected with either VV-TAP1,2+VSV low or VV-PJS-5+VSV low with viral doses indicated in FIG. 26 legend were analyzed for VSV-Np epitope specific CTLp frequency. A limiting dilution analysis was performed by using VSV-Np peptide-pulsed RMA cells as target.
Figure 28A:
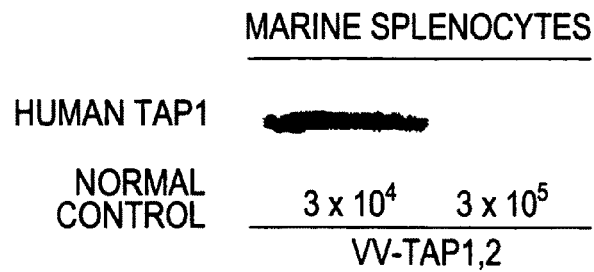
FIG. 28 is a bar graph showing murine splenocytes express introduced human TAP protein and efficiently transport a peptide-library. 3x104 or 3x105 PFU of either VV-PJS-5 or VV-TAP1,2 were injected i.p. into mice. After injection one day, the splenocytes were removed and detected for human TAP1 expression and TAP transport activities. The naive (Normal) and TAP-/- mice splenocytes are used as controls. A. The immunobloting analysis was performed to detect human TAP 1 expression. B. TAP function was tested by a peptide transport assay using a $^{125}$I-labeled peptide library as reporter.
Figure 28B:
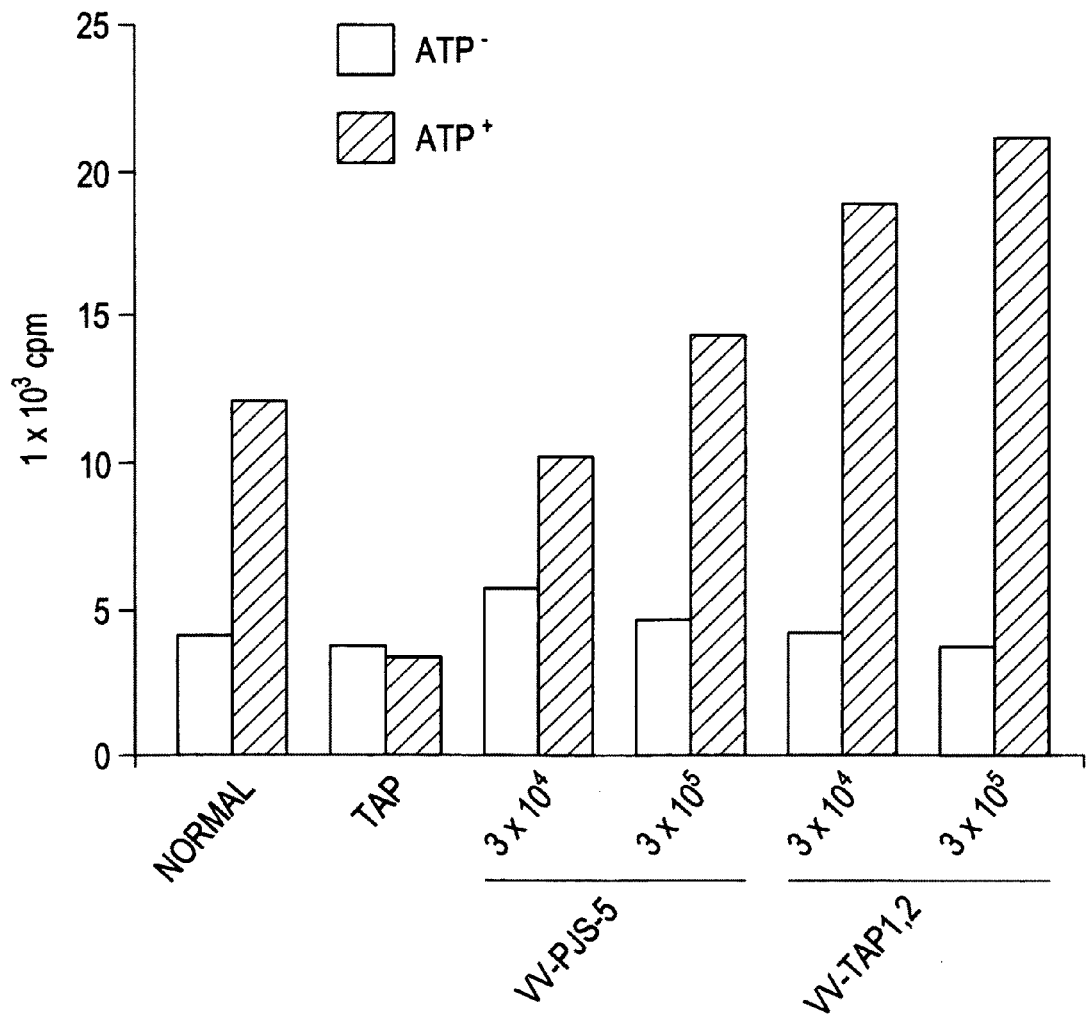
Figure 29:
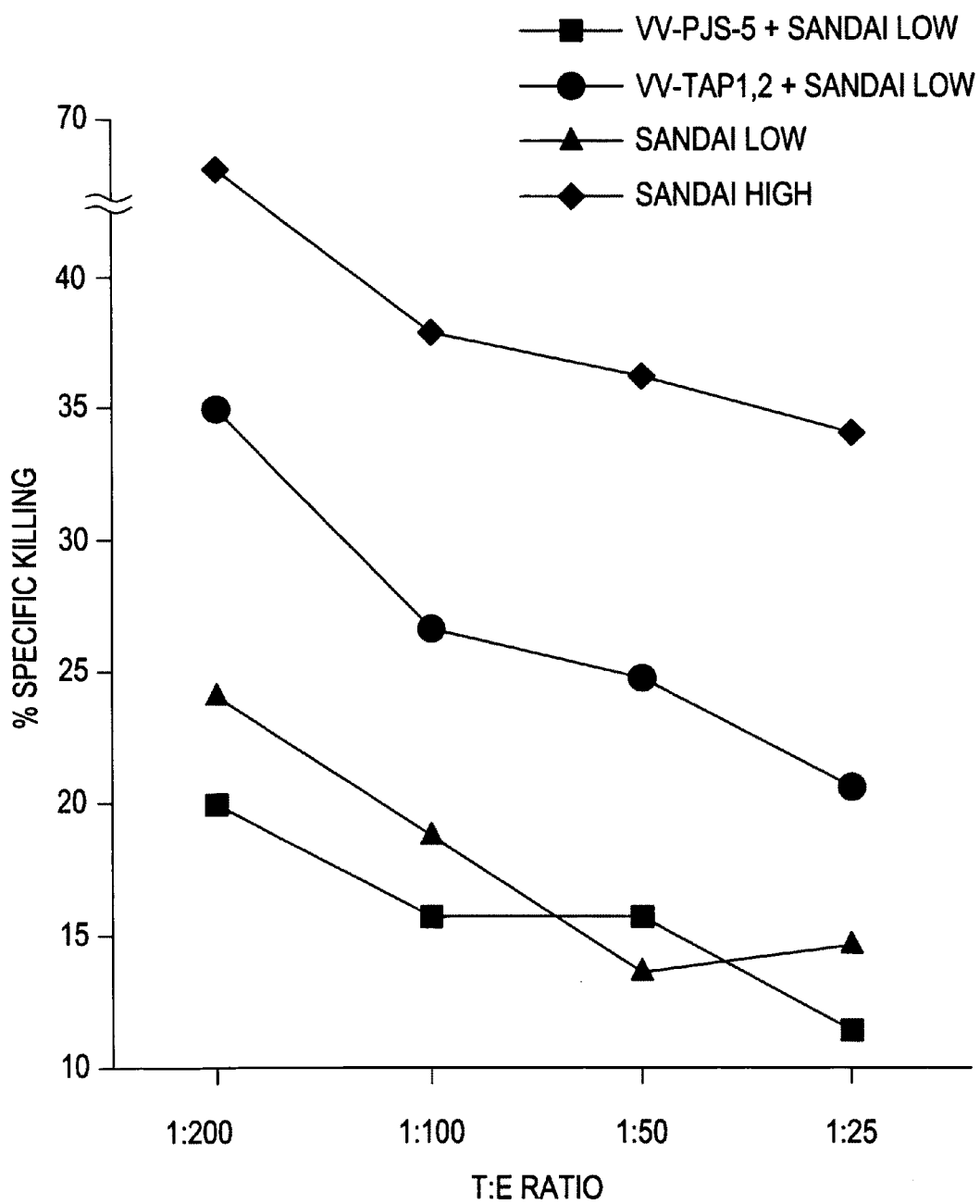
FIG. 29 is a graph showing TAP heterodimer enhances the Sandai virus-specific primary CTL response. The immunized splenocytes derived from the mice injected either Sandai virus alone or Sandai virus plus VV carrying with or without human TAP 1 and 2 genes were tested for their cytotoxic activity by using 5 µM Sendai-Np (324-332) peptide-pulsed RMA cells as target. A standard 4-h 51Cr release assay was performed. Each legend is shown as following, VV-PJS-5+Sandai low $3 \times 10^4$ (PFU) VV alone+$1.58 \times 10^5$ (CEID50) VSV, VV-TAP1,2+VSV low—3x104 (PFU) VV carrying human TAP 1 and 2+$1.58 \times 10^5$ (CEID50) Sandai virus, Sandai low—$1.58 \times 10^5$ (CEID50) Sandai virus and Sandai high $1.58 \times 10^7$ (CEID50) Sandai virus.

In order to determine whether TAP gene expression is limiting in the VSV response, the number of VSV N peptide-specific cytotoxic lymphocytes in the spleen was quantified. An increase in lysis of the VSV infected RMA targets were indicated, suggesting an increase in the number of VSV specific CTL (FIG. 23A). The in vivo immune response to VV-NP was amplified when the mice were simultaneously injected with the VV-hTAPs. The largest increase in response over VV-NP alone was seen with VV-hTAP1 and 2, and to a lesser degree with VV-hTAP1 and VV-hTAP2. This suggests that the addition of a TAP gene enhanced the VSV NP-specific CTL response. It also demonstrated that including both TAP1 and TAP2 genes was more effective than using either TAP1 or TAP2 alone (FIG. 23A). A limited dilution analysis (LDA) was performed to confirm that mice, which received VV-hTAP12 and VV-NP, contained more VSV specific CTL. The LDA data demonstrates that mice that received VV-NP had 1 VSV specific pCTL for every 78,000 splenocytes, whereas mice that also received VV-hTAP12 had 1 pCTL for every 16,000 splenocytes (FIG. 23B). The addition of TAP, therefore increased the number of VSV specific CTL approximately 5 fold. In order to directly assess whether TAP expression would directly augment responses against the wild-type virus, the same experimental protocol was attempted using a low dose of wild type VSV ($2.1 \times 10^3$ TCID50) along with $1.35 \times 10^4$ pfu VV-hTAP1 and 2 (FIG. 24). The dose of VSV used to give the minimum immune response was approximately 10,000 times less than the usual dose used for VSV immunization. It is clear that immunizing with VV-hTAP1 and 2 and VSV resulted in a large increase in immune responsiveness against VSV. This suggests that TAP could be a suitable candidate for increasing an immune response to low doses of antigen.

With the use of adjuvants, the immune response can be modulated for a MHC class I or II response. Adjuvants like immunostimulating complexes (ISCOMs), that are made of non-covalenty bound complexes of Quil A, cholesterol, and amphipathic antigen can stimulate a CD8+ CTL response (Takahashi. H. et al. *Nature* 344:873). Similarly, the T cell costimulatory molecule B7 has been shown to enhance protection against poorly immunogenic tumours (Townsend. S. et al. *Science* 259:368; Chen, L. P. et al. *Cell* 71:1093). In addition a wide variety of cytokines have been used to direct responses to either a CTL mechanism or T helper response. For example, interleukin-2 (IL-2) and IL-12 have been used to elicit a Th1 response which is more conducive to cytotoxic mechanisms (Hughes et al. *Immunol,* 74:461; Flexner et al. *Vaccine* 8:17; Heath et al. *Vaccine* 10:427); Meuer et al. *Lancet* 1:15). One adjuvant that has been widely used in animals is Freund's complete adjuvant (FCA) which is an emulsion containing heat killed mycobaterium tuberculosis. Despite the strong antibody responses that FCA produces, it is too toxic to be used in humans. However, derivatives for the minimal structure of the mycobaterium in FCA that is needed for adjuvanticity. N-acetyl muramyl-L-alanyl-D-isoglutamine (MDP), such as murabutide do not have as many toxicity problems (Cox et al. *Vaccine* 15:248).

The inventors have shown that augmentation of TAP expression does increase the immune response to the VSV. These data surprisingly imply that TAP expression or activity is limiting in normal cell lines and is the first component of the antigen processing pathway demonstrated to be in short supply in healthy mice. TAP is so effective that over 10,000 fold less wild-type virus could be used to illicit the equivalent immune response. When designing subunit vaccines, one may want to reduce the amount of innoculum used for vaccination. This is important not only for efficiency in distributing large amounts of vaccine but is also important when larger doses of a weakly immunogenic peptide are required (Melnick, *Acta Virol.* 33:482; Arnon et al. *Cur. Op. In Immunol* 4:449). The inclusion of TAP in vaccination regiments could address these problems. An additional advantage of including TAP as an adjuvant is that its ability to increase peptide transport of a number of immunogenic peptides simultaneously. In a virus containing a complex array of peptides, one could envisage that the inclusion of TAP would increase the delivery of most epitopes. Furthermore, this would aid in the delivery of diverse peptide for binding to most HLA alleles expressed in the population being immunized. TAP could be used as an adjuvant in peptide vaccines but it does not have to be restricted to viral vectors. For example, it could also be injected in other forms such as in DNA plasmids attached to gold particles or any other system which inserts the TAP complex directly into the cell's protein processing pathway (Dertzbaugh *Plasmid* 39:100). Future clinical experiments will help to further establish whether the inclusion of TAP in vaccine regiments has advantages over existing protocols, whether other components of the intracellular antigen processing pathway(s) are also limiting in healthy individuals.

Example 19

Material and Methods

Mice

C57BL/6 (H-$2^b$) mouse strains were bred at the Animal Care Centre at the University of British Columbia. All mice used for the experiments were 6- to 12-weeks-old and were maintained in accordance with the guidelines of the Canadian Council on Animal Care.

Generation of CTL Cultures and Cytotoxicity Tests

H-$2K^b$-restricted VSV- or Sendai virus-specific CTLs were generated by i.p. injection of either VSV or Sendai virus alone or one of these viruses plus recombinant vaccinia virus (VV) carrying with (VV-TAP1,2) or without (VV-PJS-5) human TAP 1 and 2 genes into C57BL/6 mice with the viral dose indicated in each figure. After 5-6 days immunization, the splenocytes were removed and cultured in RPMI-1640 complete medium containing 10% heat-inactivated HyClone FBS (GIBCO BRL), L-glutamine, 100 IU/ml penicillin, 100 mg/ml streptomycin, Hepes, 0.1 mM non-essential amino acids, 1 mM Na-pyruvate, and 50 mM 2-ME. The splenocyte cultures were incubated at $3\times10^6$ cells/ml at 37° C. for 3 days with the peptide (1 μM Sendai-Np 324-332 peptide, FAPGNYPAL) for Sendai-specific effectors or without a peptide for VSV-specific effectors. The erythrocytes were removed from the splenocytes before 3 days culture (for VSV-specific effectors) or after (for Sendai-specific effectors).

The cytotoxic activity was measured in standard 4-h $^{51}Cr$ release assays. The RMA target cells were pulsed with 5-25 μM either VSV-Np (RGYVYQGL (SEQ ID NO:5)) or Sendi-Np (FAPGNYPAL (SEQ ID NO:6)) peptide for relevant CTL response. The targets were labeled with $Na^{51}CrO4$ (100 μCi/$10^6$ cells) for 1 hr at 37° C. and cytotoxic activity was assayed in a standard 4 h $^{51}Cr$ release assay. The cytotoxicity tests were done in 96 V-shaped well plates at many effector:target ratios.

Analysis of Frequency of VSV-specific CTL Precursor

The frequency of CTL precursor was detected by limiting dilution analysis (LDA). Briefly, the assay was performed in U-bottom 96-well plate supplied with the complete medium containing 20 U/ml recombinant murine IL-2, 5% supernatent of con A-stimulated rat splenocytes and 0.1 M μ-methyl-D-mannoside. Wells contained graded concentrations of the immunized splenocytes and both irradiated cells, $1\times10^5$ syngenic splenocytes as the feeders and $3\times10^3$ VSV-Np 52-59 peptide-pulsed RMA cells as the stimulators. The cells were cultured at 37° C. for 7 days and at day 6, 80 μl cultured medium in each well was replaced with same amount of fresh one. On day 7, a standard CTL assay was performed by replacing 100 μl supernatant with 5 μM VSV-Np peptide-pulsed, 51Cr-labeled RMA cells in each well as targets. Kinetic analysis and CTL precursor (CTLp) frequency determinations were performed by the statistical methods of $X^2$ minimization as described by Taswell [Taswell, 1981 #1].

Detection of TAP Expression and Activities

Human TAP1 expression in immunized mouse splenocytes were determined by immunoblotting. Total extracts from $1\times10^5$ cells were separated on 10% polyacrylamide-SDS gels and blotted onto nitrocellulose filters. The blots were probed with TAP C-terminus-specific rabbit antisera (gifts from Dr. Monaco, J. J.) at a 1:1000 dilution for anti-human TAP1. The blots were then incubated with horseradish peroxidase-labelled anti-rabbit antibodies at a 1:10,000 dilution. The immunocomplexes were visualized by enhanced chemiluminescence (ECL) according to the instructions of the manufacturer (Amersham, UK). The naive mouse splenocytes were used as negative controls.

TAP heterodimer activities were detected by streptolysin-O mediated peptide transport assays as described by Androlewicz et al. [Androlewicz, 1993 #2] with minor modifications. Briefly, a peptide-library which contains 3240 different peptides with a glycosylation site (NXT) in each was labeled with $^{125}$I by chloramine T-catalyzed iodination to a specific activity of 10 Ci/mmol. $2\times10^6$ splenocytes from naive, TAP–/–. VV-PJS-5- or VV-TAP1,2-immunized mice were permeabilized with 2 IU/ml streptolysin-O (Murex, Norcross, Ga.) for 15 min at 4° C. After removing unbound streptolysin-O and the cells were resuspended in 37° C. intracellular transport buffer (50 mM Hepes, pH 7.0, 78 mM KCl, 4 mM $MgCl_2$, 8.37 mM CaCl2, 1 mM EGTA, 1 mM dithiothreitol (DTT). Adjust pH to 7.3 with KOH) for 5 min to initiate pore formation. The iodinated peptide-library (~66 ng) was then added immediately. The incubation was continued for another 10 min in the presence or absence of 10 mM ATP (Sigma Chemical Co., St. Louis, Mo.). Afterwards, the cells were transferred to ice and were lysed in a buffer containing 1% NP40, 150 mM NaCl, 5 mM $MgCl_2$, 50 mM Tris-HCl pH 7.5. The nuclei were removed by centrifugation of samples at 14,000 rpm for 10 min. Translocated peptides that had been glycosylated in the ER were recovered by absorption to concanavalin A-Sepharose beads (Pharmacia Diagnostics, AB). The beads were washed five times in lysis buffer. The associated radioactivity was measured in a γ-counter (model 1282CS; LKB Pharmacia).

Example 20

TAP1 increases the expression of MHC Class I on the Surface of a Metastatic Prostate Cancer Cell Line Background The inventors have examined the effect of TAP1 gene transfection on the level of MHC Class I displayed by cells derived from a metastatic cancer model developed by the laboratory of Timothy C. Thompson from the Baylor College of Medicine, Houston, Tx. (1). This model of metastatic disease makes use of a primary prostate cancer cell line 148-1 PA and a metastatic cell line 148-1 LMD derived from the same clone. The parental, primary cell line has been shown to be more immunogenic than the metastatic 148-1 LMD line as examined by the growth of the tumor in immune competent, syngeneic mice. Interestingly, while both cell lines were capable of inducing syngeneic and allogeneic antitumor CTL, only the parental cell line was susceptible to killing by antitumor CTL. Both tumors, however, express reduced levels of genes involved in antigen presentation such as: TAP1, TAP2, LMP-2 and LMP-7 (24). It is possible that the expression of these genes is not sufficient for effective presentation to specific CTL as is the case for the metastatic derivative of this prostate tumor model.

Materials and Methods

The cell lines described by Lee et al. (24) were maintained in DMEM and 10% Fetal Calf Serum (FCS) at 37 C and 5% $CO_2$. Human TAP1 cloned in the mammalian expression vector pCEP4 (Invitrogen) was obtained with permission of use from Ping Wang, University of Lund, Sweden. Vector carrying human TAP1 (10 µg) was incubated with Lipofectamine reagent (8 µl) (Life Technologies) in 200 µl of serum-free media for 15 min. Then the mixture was overlayed on $4\times10^5$ metastatic 148-1 LMD in a total of 1 ml of serum-free media and incubated 4 hr further. Then FCS was added to a final of 10% concentration and the cells were incubated for an additional 48 hr. The selection of stable transfectants was carried out by incubating the cells in 200 µg/ml hygromycin with regular passage for one month.

Fluorescence Activated Cell Sorting (FACS) machine (BD-FACScalibur) was used to measure the expression of MHC class I expression on the cell surface. Clones were isolated and examined for their expression of MHC Class I by staining the cells with Y3 followed by washing and staining with FITC conjugated goat anti-mouse IgG. Y3 anti H2-Kb antisera is a conformational dependent antisera that binds to MHC class I only in the presence of bound antigenic peptide. As a control for non-specific fluorescence the primary antibody was omitted from the staining protocol.

Results and Discussion

Figure 30A:
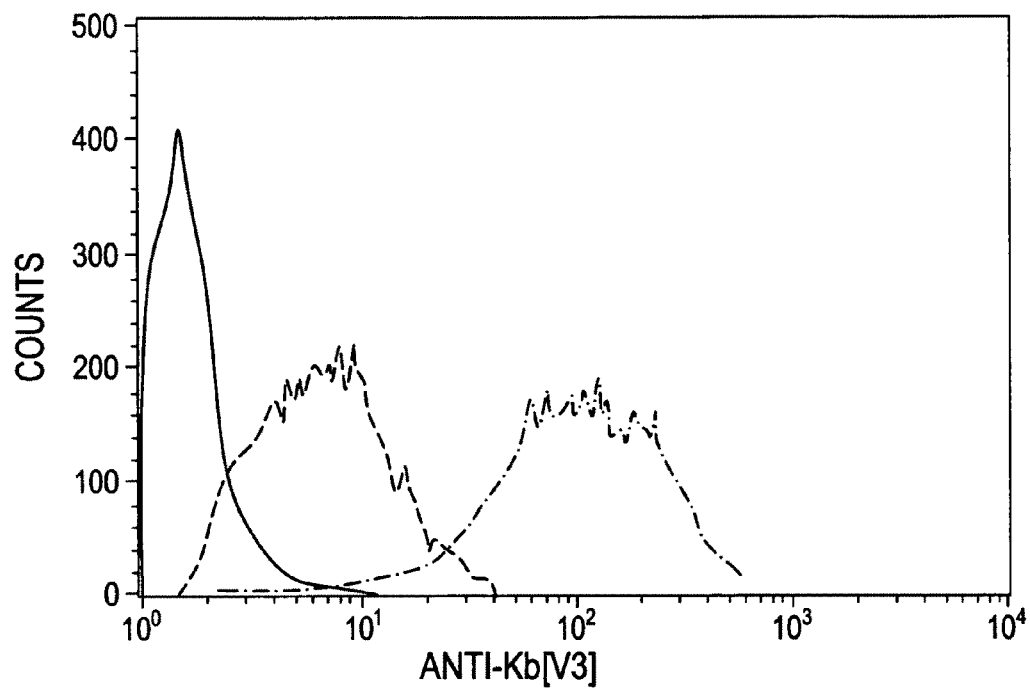
FIG. 30 is a FACS analysis showing reconstitution of the MHC Class I level on the surface of mouse prostate cells using Interferon-γ or TAP1 gene therapy. (A) 148-1 LMD metastatic cancer cells untransfected (green) or transfected with TAP1 (red) were examined by FACS for the level of expression of MHC Class I by staining with the Y3 anti-H2 Kb antibody. (B) 148-1 PA untreated (green) or treated with 400 U/ml Interferon-γ (red) were examined by FACS for the level of expression of MHC Class I by staining with the Y3 anti-H2 Kb antibody. Purple indicates the staining control.
Figure 30B:
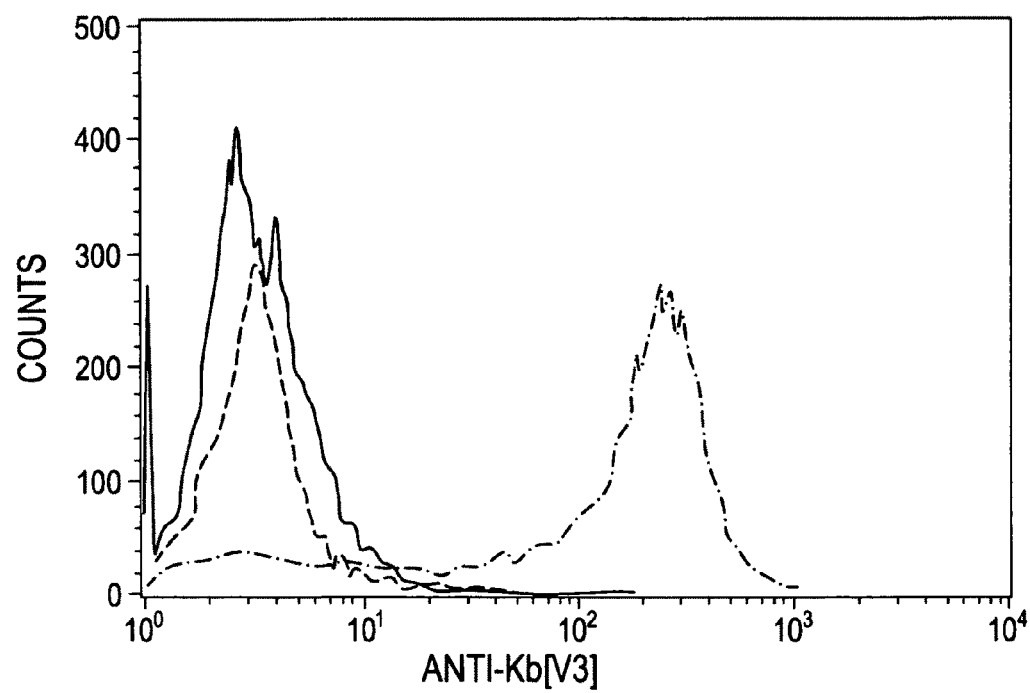

The examination revealed a severely impaired expression of MHC Class I on the cell surface in both the metastatic and primary cell lines. The inventors were able to reconstitute the expression of MHC Class I on the cell surface by transfecting these cells with TAP1 (FIG. 30A) or, in the absence of TAP1, by treating the cells with interferon-γ (FIG. 30B).

FIG. 21

TAP1 Augmenting B16F10 Tumor Antigenicity And Immunogenicity

Background

B16F10 is a well-studied melanoma cell line derived from C57BL/6 mice. The cell line expresses the tumor-associated antigens TRP-1. TRP-2, and gp100. B16F10 is not immunogenic and is resistant in vivo to IL-2 treatment and adoptive transfer of CTL. In vivo, immune responses are not elicited even when the cells are transfected with the accessory molecule B7.1 or when mice are vaccinated with cells mixed with BCG.

The non-immunogenicity of B16 F10 can be attributed to defects in MHC class I restricted antigen presentation. MHC class I, TAP1, TAP2, tapasin, proteasome LMP2, LMP7 and PA28 are down regulated in this cell line (25).

The inventors show that transfection and expression of TAP1 alone, restores the presentation of melanoma tumor associated antigen (TRP-2) in the context of MHC class I, despite the multiple defects in the antigen presentation pathway. In addition to the TRP-2 antigen, TAP1 transfection of B16F10 cells also facilitates the presentation of the viral antigen, VSV-NP.

The increase in MHC class I antigen presentation is sufficient for both tumor and viral antigens in the context of MHC I to makes TAP1 transfected B16 F10 susceptible to killing by TRP-2 specific and VSV-NP, cytotoxic T-cells respectively. Also, mice bearing pre-existing, non-immunogenic B16 F10 tumors generate specific anti-tumor immune responses when treated in vivo with a vector containing TAP1.

Materials and Methods

Transfection

The transfection of melanoma cell line B16 F10 with rat TAP1 and net TAP2 followed the protocol outlined in Materials and Methods for Examples 1-8.

Defection of MHC Class I Molecules

Surface expression of the H-2$K^b$ allele was detected by indirect immunofluorescence using the conformational-dependent mouse monoclonal antibodies (mAbs), Y-3 (ATCC), which is specific for $K^b$-$b_2$M complexes. Fluorescein isothiocynate-conjugated (FITC) rabbit anti-mouse IgG (Dakopatts, DK) was used as the secondary antibody. A FACScan analyzer (Becton and Dickinson, Mountain View, Calif.) measured the mean logarithmic fluorescence intensity.

Detection of Rat TAP Genes

RT-PCR analysis of rat TAP mRNA expression was performed in B16F10 TAP-transfectants. Total RNA was extracted by using the RNeasy Kit (Qiagen) according to manufacturer's protocol. Random-primed cDNA was generated using the RETRO script, RT-PCR Kit (Ambion) following the manufacturer's instructions. The inventors then used 0.5 μg of cDNA from each spleen to amplify sequences corresponding to rat TAP1 and TAP2 using the following primer sets: GACCGGACTCTGGACAGC and GTAAATTC-CGGGGCATCTCCT corresponding to rat TAP1: AGGAAGCAGATTTCAGAACTC and AGTCCT-GAGAGGGCTCAGTGT corresponding to rat TAP2 respectively. The β-actin subunit primer set was obtained from Ambion. For all targets, the PCR reaction consisted of 30 cycles of amplification at an annealing temperature of 56° C. using Platinum Taq polymerase (Invitrogen), according to manufacturer's instructions. One tenth of the product of each PCR reaction was examined by agarose gel electrophoresis. The inventors measured the intensity of β-actin product in order to ensure that the reaction kinetics and starting material of cDNA in each reaction was equivalent.

Generation of Effector Cell Populations

Virus-specific CTL populations were generated by infecting mice intraperitoneally (ip) with $10^7$ tissue culture infection dose (TCID) units of VSV. CTL were collected on day 5 post immunization from immunized spleen and stimulated with 1 μM VSV-NP peptide (amino acids 52-59) in RPMI-1640 medium containing 10% HI HyClone FBS (Gibco), 20 mM Hepes, 2 mM L-glutamine, 0.1 mM essential amino acids, 1 mM sodium pyruvate, 50 μM mercaptoethanol (ME), and penicillin/streptomycin (henceforth referred to as RPMI complete medium). Seven days later, this bulk population was used in a CTL assay.

For tyrosinase-related protein 2 (TRP-2) specific CTL generation, the specificity of splenocytes was generated by injecting mice intraperitoneal with $3 \times 10^6$ γ-irradiated RMA-S cells pulsed with 5 μM, $K^b$-restricted TRP-2 peptides (SVYDFFVWL) for 5 days. Upon removal the splenocytes were cultured with 1 μM TRP-2 for 6 days and used for bulk-culture CTLs in a standard 4 h $^{51}$Cr release assay.

Cytotoxicity Assays

Target cells (B16F10 and rat TAP1-transfectant. B16.TAP1) for the CTL assays were loaded with $^{51}$Cr by incubating $10^6$ cells with 100 μCi of $^{51}$Cr (as sodium chromate, Amersham) in 250 μl of CTL medium (RPMI-1640 containing 10% HI FBS, 20 mM Hepes) for 1 hour. Following three washes with RPMI, 2% FBS, the target cells were incubated with the effector cells at the indicated ratios for 4 hours. 100 μl of supernatant from each well was collected and the $^{51}$Cr release was measured by a O-counter (LKB Instruments). The specific $^{51}$Cr release was calculated as follows: [(experimental−media control)/(total−media control)]× 100%. The total release was obtained by lysis of the cells with a 5% Triton-X 100 (BDH) solution.

Inoculation of Mice with Tumor Cell Lines and Tumor-Therapy $1.5 \times 10^5$ B16F10 cells in PBS were injected subcutaneously (s.c.) into C57B1/6 syngeneic mice. One day after, the mice received s.c. $1 \times 10^6$ (PFU) of either vaccinia vector alone (VV-PJS-5, 5 mice per group) or vaccinia-carrying rat TAP1 (VV-rTAP1, 5 mice per group). This procedure was repeated 7 days later. All mice were killed 17 days after the introduction of the tumor cells. The tumor sizes are measured and the difference between two groups was analysed by a one tailed Student's t-text (p<0.5).

Results and Discussion

Figure 31A:
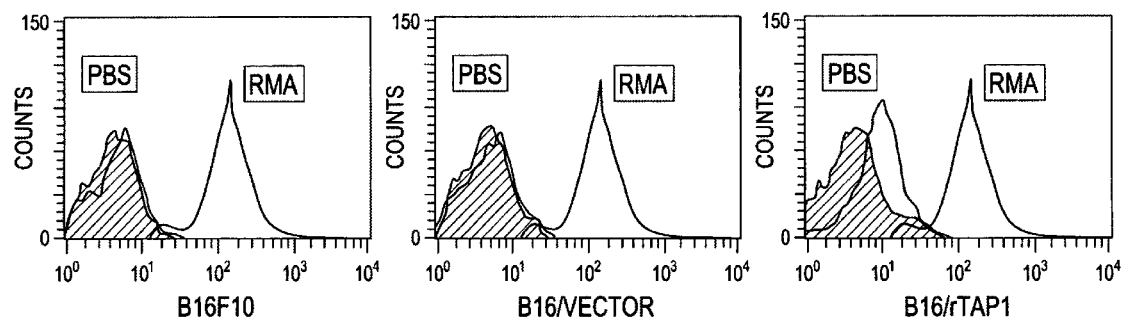
FIG. 31 is a FACS analysis of B16 cells transfected with TAP1 measures an increase in antigen loaded MHC class I on cell surface over untransfected and vector alone transfected cells. Increases in the expression of both a) K$^b$ and b) D$^b$ forms of MHC class I. RMA cells are used as a positive control. The substitution of PBS for the primary antibody for B16 serves as negative control.
Figure 31B:
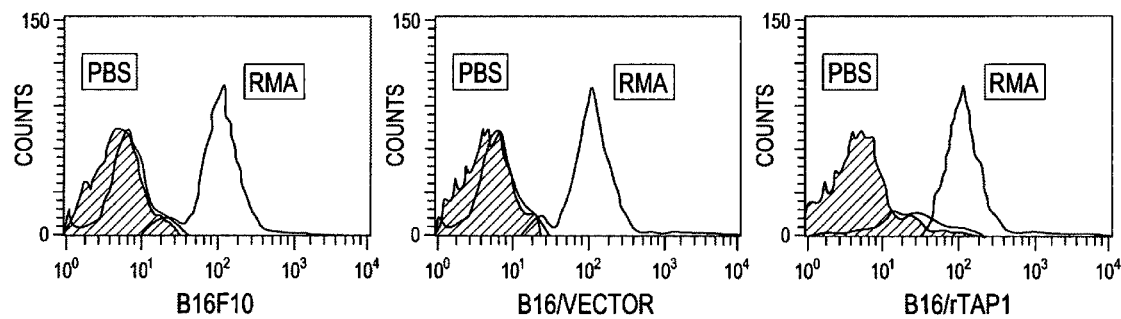
Figure 32A:
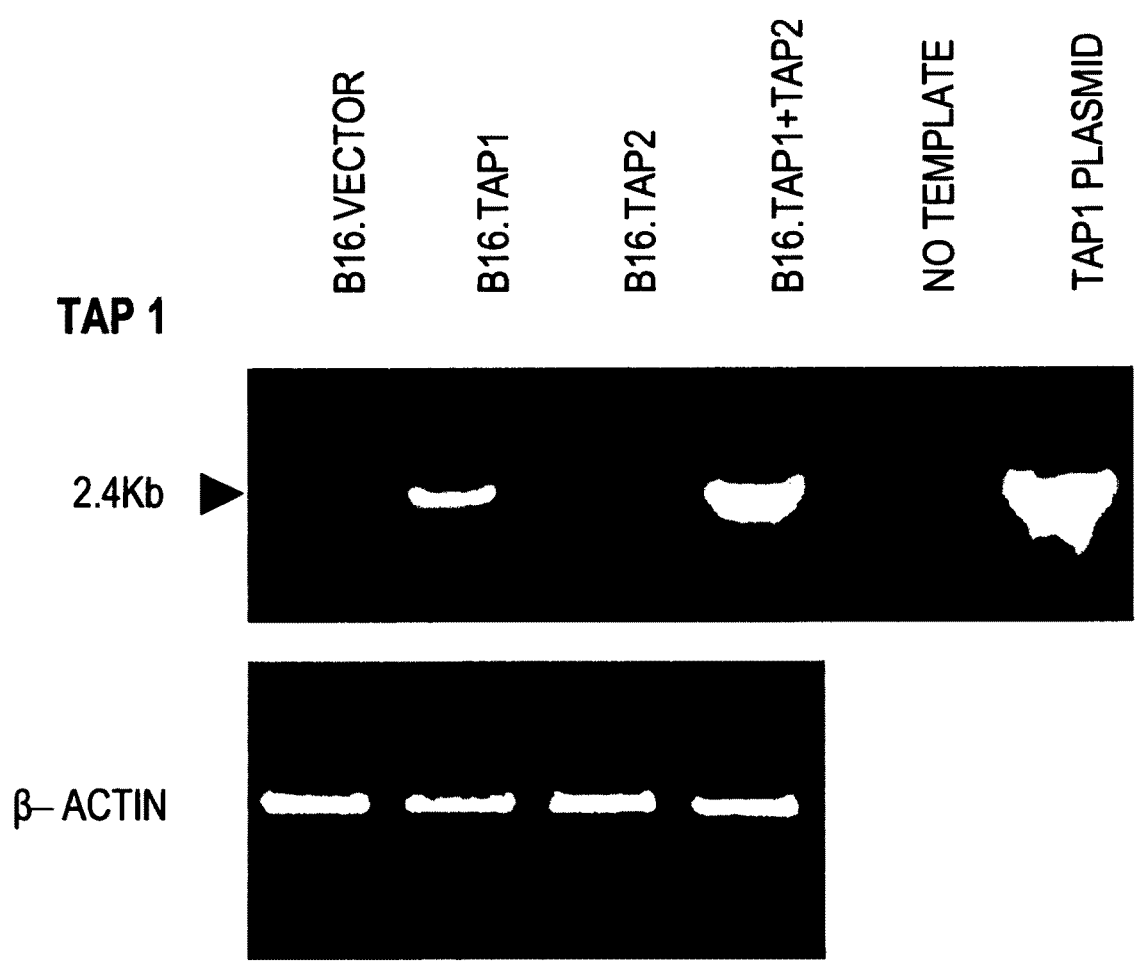
FIG. 32 is an agarose gel electrophoresis of RT-PCR products generated with primers specific for rTAP 1(a), and rTAP 2 (b) is used to confirm the Transfection of B16 F10 cells. β-actin was used to control for reverse transcription and template loading of the PCR.
Figure 32B:
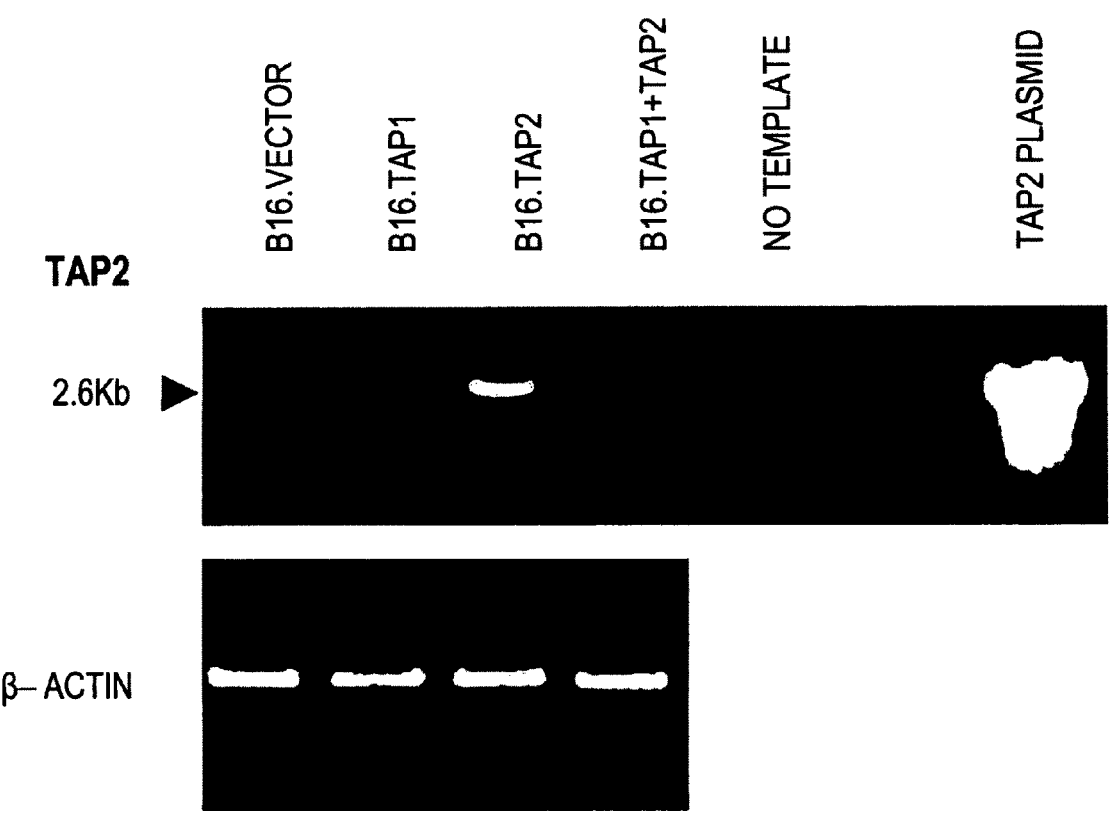

It has been reported that the murine melanoma cell line. B16F10, down-regulates the expression of MHC class I molecules and TAP1 and TAP2 proteins (25). These defects result in cells unable to present tumor antigen for recognition by immune system. In a mouse small cell lung carcinoma cell line. CMT.64, that shows a phenotype similar to B16F10, the inventors transfected rTAP1 gene into the cells and found that the transfectants increased its antigen presentation capacity (26). To see whether the same treatment can also apply to B16F10 cell line, the inventors transfected rat TAP1 and/or TAP2 gene in to the B16F10 cell line. Transfection was confirmed by RT-PCR and all transfectants express the introduced rTAPs (see FIG. 31A,B). B16F10 transfected with rTAP1 expresses higher surface $H-2K^b$ molecules than wild-type and vector-transfected cells (FIG. 32) demonstrating that TAP is essential for antigen presentation despite other deficiencies in the antigen presentation pathway.

Figure 33:
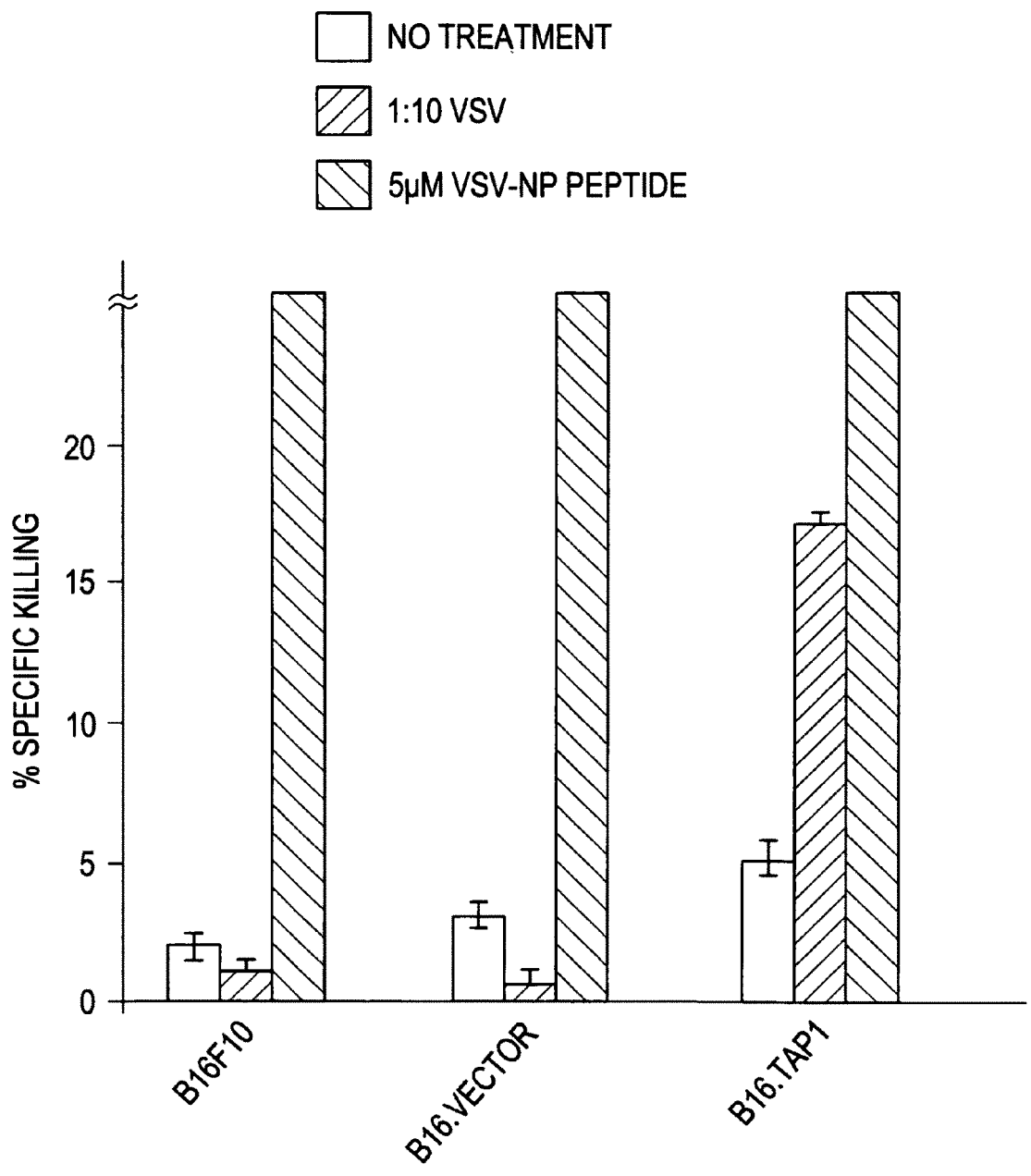
FIG. 33 is a bar graph showing TAP1 expression enhanced the presentation of the tumour associated antigen. TRP-2, by B16 F10 cells. The TRP-2 antigen presentation capability of B16 F10 cells alone was compared with that of B16 F10 cells transfected with TAP1. In $^{51}$Cr release assays, the effectors were obtained by injecting mice with γ-irradiated RMA-S cells pulsed with the TRP-2 peptide epitope. The spleens of the injected mice were taken 5 days later. The splenocytes were then cultured in complete RPMI medium and restimulated by the TRP-2 peptide epitope for 5 days. These restimulated splenocytes were tested to be specific for TRP-2 presented by H2-K$^b$ molecules (data not shown). Standard 4-hour $^{51}$Cr release assays were performed using the restimulated splenocytes as effectors and B16 cells or B16 cells transfected with TAP1 as targets. B16 cells pulsed with the peptide epitope were used as the positive control. The results showed that in TAP1 expressing B16 F10 cells the presentation of TRP-2 was augmented significantly. TAP1 enhanced the presentation of an endogenous tumour associated antigen by B16 F10 tumour cells.

To see if introducing rat TAP1 gene into B16F10 cells restores the antigenicity and immunogenicity of these tumor cells, the inventors performed a cytotoxicity assay to test the cells' capacity on the presentation of $K^b$-restricted epitopes derived from VSV. The susceptibility to specific lysis of TAP transfected B16F10 cells was compared to untransfected B16 F10 cells and B16 F10 cells transfected with vector alone. Each of these 3 cell lines was infected with VSV (1:10 moi) and cell lysis by antigen specific splenocytes was measured with a CTL assay. Cells pulsed with VSV-NP 52-59 peptide acted as a positive control and untreated cells were used as a negative control. The CTL assays demonstrated that only TAP transfected B16 F10 cells infected with VSV were lysed by VSV antigen specific splenocytes (FIG. 33). Untransfected B16 F10 and B16 F10 cells transfected with vector alone were not lysed by VSV specific splenocytes. The results of the CTL assay shows that antigen presentation and immunogenicity is significantly increased in TAP transfected B16 F10 cells compared to wild type or vector transfected B16 F10 cells. Only cells transfected with rTAP1 gene are able to present VSV-NP epitope significantly (FIG. 33).

Figure 34:
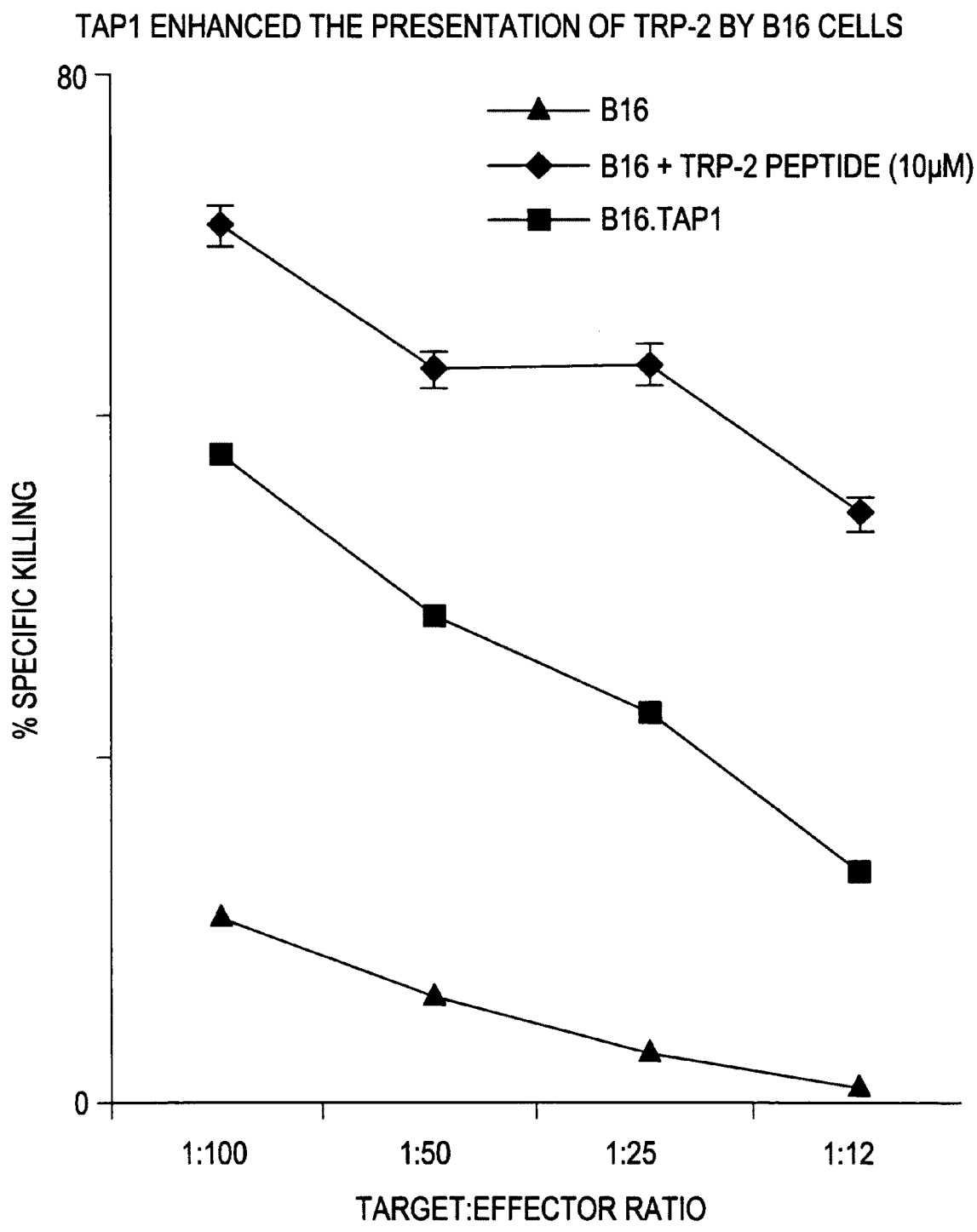
FIG. 34 is a graph showing increased specific killing of B16 cells transfected with TAP1 compared with B16 F10 cells not transfected with TAP1. Cytoxic T lymphocytes are specific for the melanoma-associated antigen. Untransfected B16 cells pulsed with TRP-2 antigen are used as a positive control.

Since B16F10 cell line express tumor-associated antigens, TRP1. TRP2 and gp100. It is important to test whether TAP1-transfected B16F10 can also present the tumor-associated antigen TRP-2, one of these tumor-associated antigens. The TRP-2-specific CTLs were generated by the splenocytes of the mice injected with the synthetic epitope peptide pulsed RMA-S cells. The lysis of TAP1-transfected B16F10 cells (B16.TAP1) by splenocytes specific for TRP-2 antigen is dramatically increased over untransfected B16 F10 cells as demonstrated by CTL assay (FIG. 34). This result indicates that TAP1 enhanced the presentation of an endogenous tumor-associated antigen in B16F10 cells.

Figure 35:
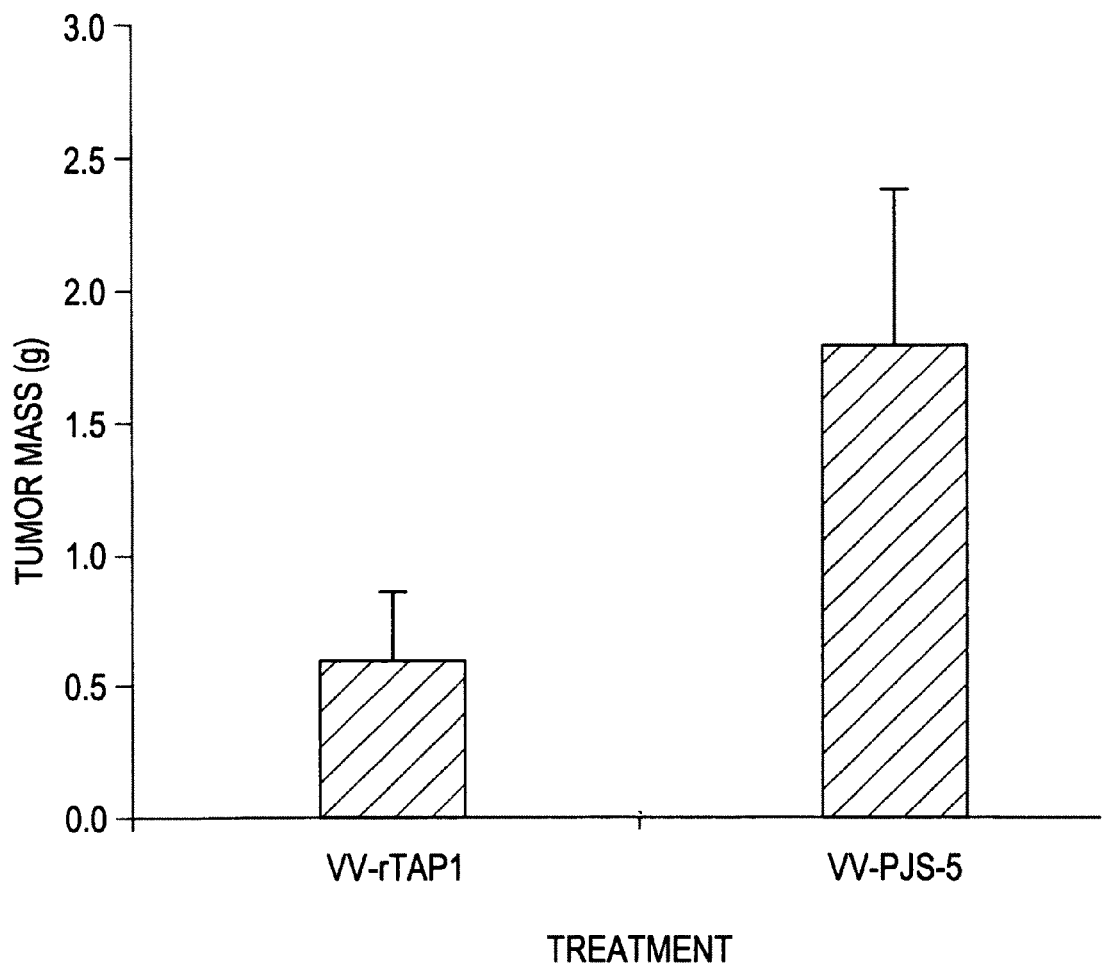
FIG. 35 is a bar graph showing subcutaneous injection of a vaccinia vector containing TAP1 inhibits significantly (one tail Student's t-test, p<0.5) the growth of established B16 melanoma tumors 3 fold when compared to tumor growth in mice treated with subcutaneous injections of vaccinia vector alone. The experiment used mice syngeneic with B16 cell line.

Next, the inventors investigated the ability of TAP1 to act as a therapeutic by in mice bearing B16 melanoma tumors. Wild-type B16 F10 cells were introduced into the flanks of mice causing tumors to grow. A vaccinia vector containing the TAP1 gene was injected subcutaneous on the same flank as the tumor on two occasions separated by seven days. The mice were killed 17 days after the tumors were introduced and the tumor mass was measured. Analysis (Student's t-test, p<0.5) of tumor mass demonstrated that mice receiving the vaccinia TAP vector (VV-rTAP1) had significantly smaller tumors than mice that received a vaccinia vector not containing TAP (VV-PJS-5 (vector alone)) (FIG. 35).

In conclusion increased TAP1 expression increases the amount of MHC class I bearing both exogenous and endogenous antigen on the surface of B16 F10 cells making them antigenic and immunogenic. This resultant increase in immunogenicity is capable of inhibiting B16 tumor growth in vivo.

Example 22

Tap Expression Improves Immune Recognition of and Protection Against Malignant Cells In Vivo Background Neoplastic cells arise frequently in the body due to a variety of external and internal influences and the inventors depend on the immune system to recognize and destroy these cells before they develop into tumors. However, malignant transformations may be accompanied by phenotypic changes resulting in the ability of the cancer cells to escape the immunosurveillance mechanism. As the phenotypic changes vary with each neoplasm the inventors are unable to develop one treatment for all cancers. Fortunately, many tumors fall into one of several larger groups of phenotypes. One such group presents with increased tumorigenicity due to a decrease in MHC class I expression (27-31). A decrease in cell surface expression of MHC class I can be due to a defect anywhere in the MHC class I biosynthetic pathway (30, 32). There are many cellular proteins that contribute to MHC class I assembly (33-36). The TAP complex is one of the most important components. The function of the TAP complex is to supply endogenously-processed peptides from the cytosol into the ER for binding to relevant MHC class I, resulting in cell surface presentation of these complexes to CTLs. Loss of the TAP complex is highly correlated with loss of HLA expression in cervical carcinoma (37). In addition, a higher frequency of downregulation of this complex has been observed for metastatic lesions than for primary lesions (29). Particularly, the TAP complex has been implicated in tumorigenicity of several cancers such as melanomas, cervical carcinomas, and renal cell carcinomas (29, 38, 39). These findings suggest that TAP downregulation may represent an important mechanism for immune escape of malignant cells in a variety of tumors.

The immune system has evolved a very intricate recognition mechanism to eliminate diseased cells. In order for a tumor to proliferate it has to evade the cells involved in tumor recognition. The major anti-tumor effector mechanisms are the CD8$^+$ CTLs and NK cells (reviewed in 30). The functions of both effectors are controlled by MHC class I. CD8$^+$ CTLs recognize surface MHC class I restricted tumor associated antigens (TAA) and destroy tumor cells (40), whereas NK cells only lyse the targets with absence or downregulation of surface MHC class I.

Small cell lung carcinomas (SCLCs) are highly malignant in humans and are generally fatal. SCLCs in mice have similar characteristics. The CMT.64 cell line is one of the SCLCs which arose spontaneously in a C57BI/6 mouse (41). This cell line is lacking in both MHC class I surface expression and endogenous antigen presentation. IFN-γ treatment corrects these deficiencies. However, the underlying defect remains unknown (42, 43). The inventors have recently shown that CMT.64 cells have many defects of components in antigen presentation pathway, such as MHC class I heavy chain, $\beta_2$-m, proteasome subunits (LMP 2 and LMP 7), and TAP-1 and -2 (44). These defects can be rescued by INF-γ treatment (18). Although the CMT.64 cells are very poor at antigen presentation, reconstitution with rTAP1 and rTAP1,2 restores viral antigen presentation in vitro (44, 45). These data demonstrated that the blockage of antigen presentation in the SCLC CMT.64 is at the level of transport of peptide from the cytoplasm to the ER.

It is difficult to treat cancers since many of them have multiple cellular defects. However, if restoring one component will allow the hosts' immune system to recognize and destroy the cancer, then the course of treatment would be less complicated. Many of the tumors lacking surface MHC class I have TAP losses or dysfunctions (29). If CMT.64 transfected with TAP is sufficient for restoring antigen presentation in vitro, does it follow that the immune system recognize the TAP-expressing tumor cells, destroy them and thus prevent metastasis in vivo? To examine this possibility, the TAP-deficient CMT.64 as well as TAP-transfected cell lines derived from CMT.64, were tested to see if TAP could improve the immune response against cancer cells and thus improve survival of animals bearing this tumor.

Materials and Methods

Animals

The mouse strain C57BL/6 (H-2$^b$) was obtained from Jackson Laboratories but housed at the Biotechnology Breeding Facility (University of B.C.). The H-2$^b$ nude mice {B/6 Nu-M (C57BI/6 NTAC-NufDF)} were obtained from Taconic (Hanover, N.Y., USA) and kept in specific pathogen free incubators. The mice were maintained according to the guidelines of the Canadian Council on Animal Care. The mice used in the experiments were between 6 and 12 weeks of age and were sacrificed by $CO_2$ asphyxiation.

Recombinant Vaccinia Virus Construction (VV)

Recombinant VV was constructed by homologous recombination of the wild type VV WR strain by infecting CV-1 cells transfected with the plasmids pJS5, pJS5-rTAP1, pJS5-rTAP2 or pJS5-rTAP1,2 according to previously described protocols (Macket et al., 1989).

Purification of VV Stocks

Crude cell stocks were used for the infection of cells in culture however purified stocks of VV were used when injecting mice. To purify the VV, 3 L batches of VV infected Hela S3 cultures were used. The VV was released from the cells by homogenization with a Dounce Homogenizer before centrifugation at 750×g for 5 minutes at 4° C. The supernatant was trypsinized with 0.1 vol. of 2.5 mg/ml trypsin for 30 minutes at 37° C., then layered onto an equal volume of 36% sucrose in 10 mM Tris-HCl pH 9.0. It was centrifuged for 80 minutes at 4° C. at 25,000×g and the pellet was then resuspended in 1 mM Tris-HCl pH 9.0. The pellet was trypsinized again before being layered onto a 24-40% continuous sucrose gradient and centrifuged for 45 minutes, at 4° C. at 18,750×g. The milky band was collected and saved while the pellet was trypsinized and repurified on another sucrose gradient. All of the bands collected were pelleted by diluting with 2 volumes of 1 mM Tris-HCl pH 9.0 and centrifuging for 60 minutes at 4° C. at 25,000×g. The viral pellet was resuspended in 1 mM Tris-HCl pH 9.0, and 0.5 ml aliquots were stored at −80° C. or −135° C.

Tissue Culture

The small cell lung carcinoma cell line. CMT.64, used in the cancer experiments originated spontaneously from the C57BL/6 mouse strain (41). All of the stable CMT.64 transfectants containing rTAP-1 (CMT.1-4, CMT.1-10), rTAP-2 (CMT.2-1, CMT.2-10), rTAP1,2 (CMT.12-21) and the vector only control (CMT.neo) were created by transfecting CMT.64 cells with the rTAP cDNA in mammalian expression vector pH (Apr-1neo) (44, 45). All cell lines including RMA cell line were grown in either DMEM or RPMI containing 10% fetal bovine serum (FBS).

Generation of Effector Cell Populations

Virus-specific CTL populations were generated by infecting mice intraperitoneally (ip) with 10$^7$ tissue culture infection dose (TCID) units of VSV or at the suggested plaque forming units (pfu) for VV-TAP or VV-pJS5 vector. CTL were collected on day 5 post immunization from the cervical lymph nodes (LN), or spleen and cultured in RPMI-1640 medium containing 10% HI HyClone FBS (Gibco), 20 mM Hepes, 2 mM L-glutamine, 0.1 mM essential amino acids, 1 mM sodium pyruvate, 50 µM β-mercaptoethanol (β-ME), and penicillin/streptomycin (henceforth referred to as RPMI complete medium). The LN cell suspensions were cultured at $4\times10^6$ cells/ml for 3 to 5 days in the absence of stimulation before being used in a CTL assay, whereas the splenocyte suspension was cultured for 7 days with peptide stimulation. Bulk populations of VSV-specific CTL were maintained by weekly restimulation with 1 (M VSV N peptide (amino acids 52-59) plus pulsed irradiated (2200 Rads) stimulator splenocytes. Irradiated stimulator cells and CTL were incubated together at a ratio of 4:1 in RPMI complete medium containing 20 units/ml hIL-2. Seven days later, this bulk population was used in a CTL assay.

Figure 37A:
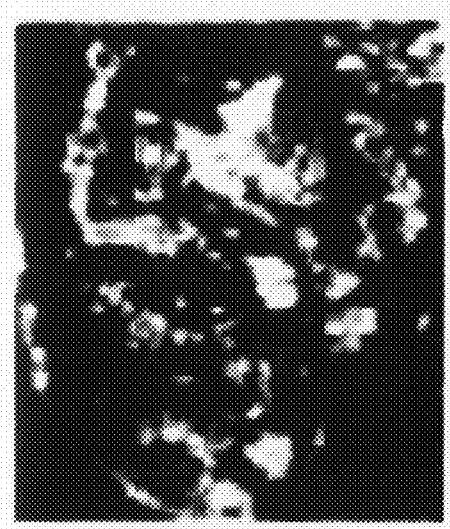
FIG. 37 shows the control of in vivo-tumor-growth and improvement of mice survival by introducing rTAP heterodimer or rTap1 but not rTap2 into CMT.64 tumor cell line. CMT.64, or its tranfectants were injected ip. Into syngeneic mice. A after one month, one representative mouse from each group was sacrificed and the tumor-growth pattern was examined. I-CMT.neo, II-CMT.1-10, III-CMT 2-10 and IV-CMT.12-21. Arrows indicate tumors. B. The time of morbidity in mice survival experiments was recorded for each group. Statistical analysis yields P-value, comparing survival rates of CMT-64-bearying mice (top) or CMT.neo-bearing mice (bottom). C. The specificity of splenocytes from a mouse injected with CMT.neo (left-panel) or CMT 1-4 (right panel) was determined in a CTL assay against the targets CMT.neo and CMT1-4.
Figure 37A:
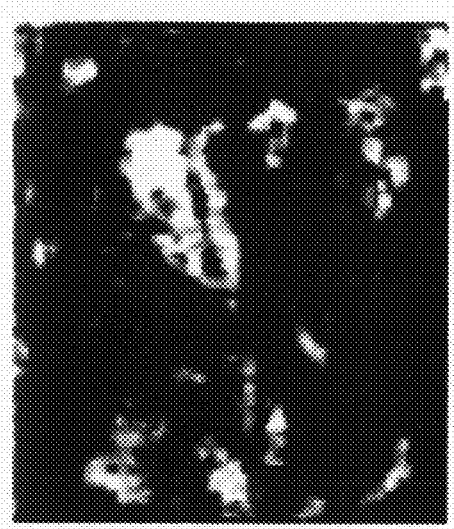
Figure 37A:
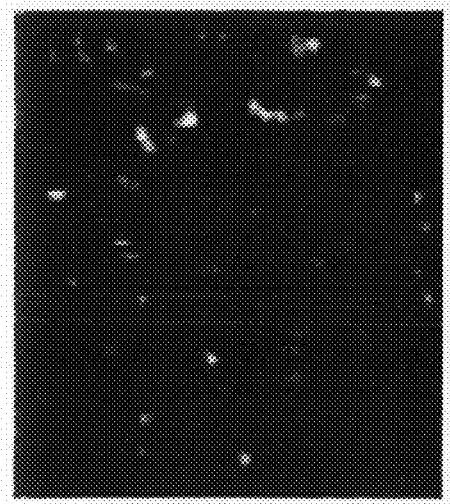
Figure 37A:
Figure 37B:
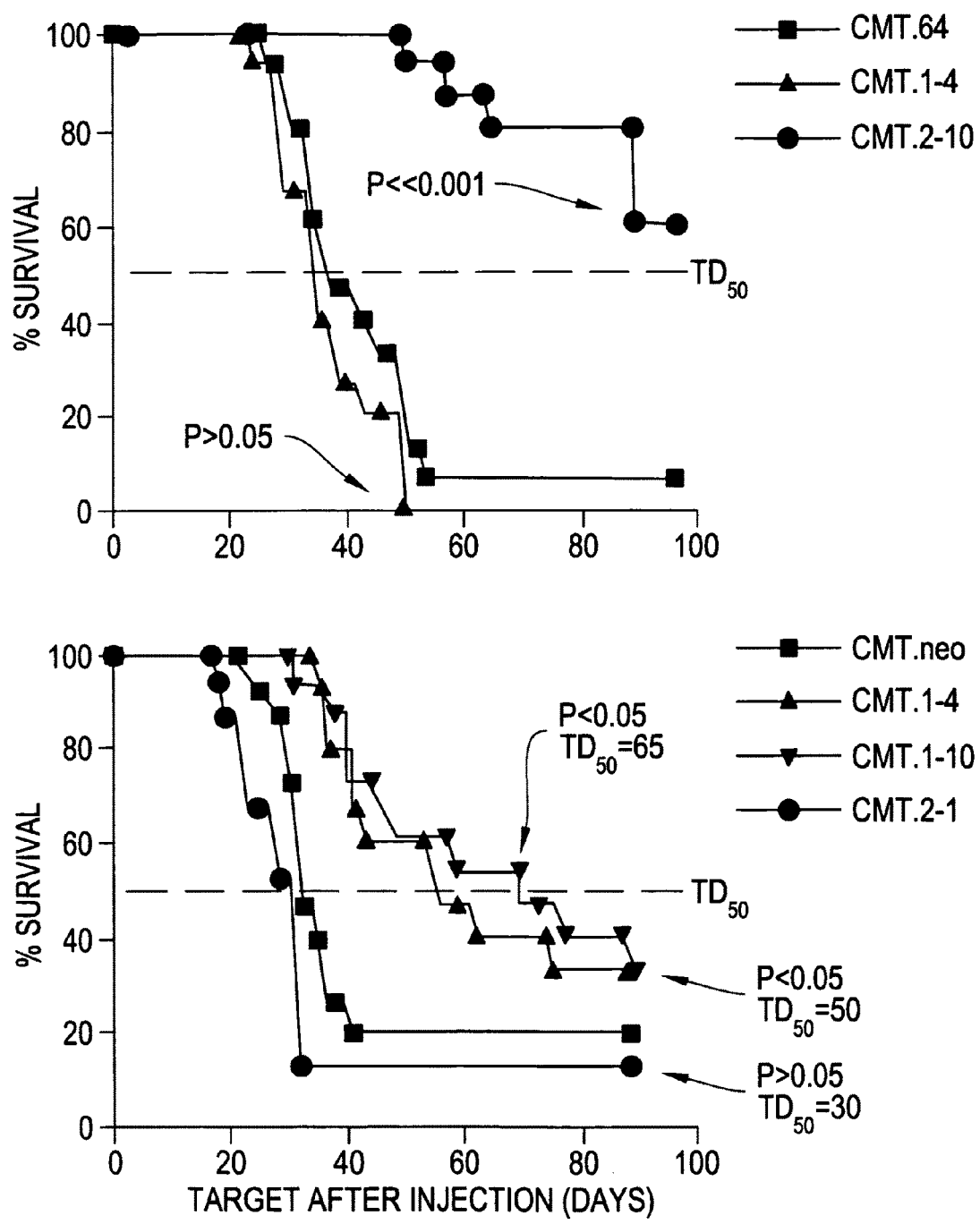
Figure 37C:
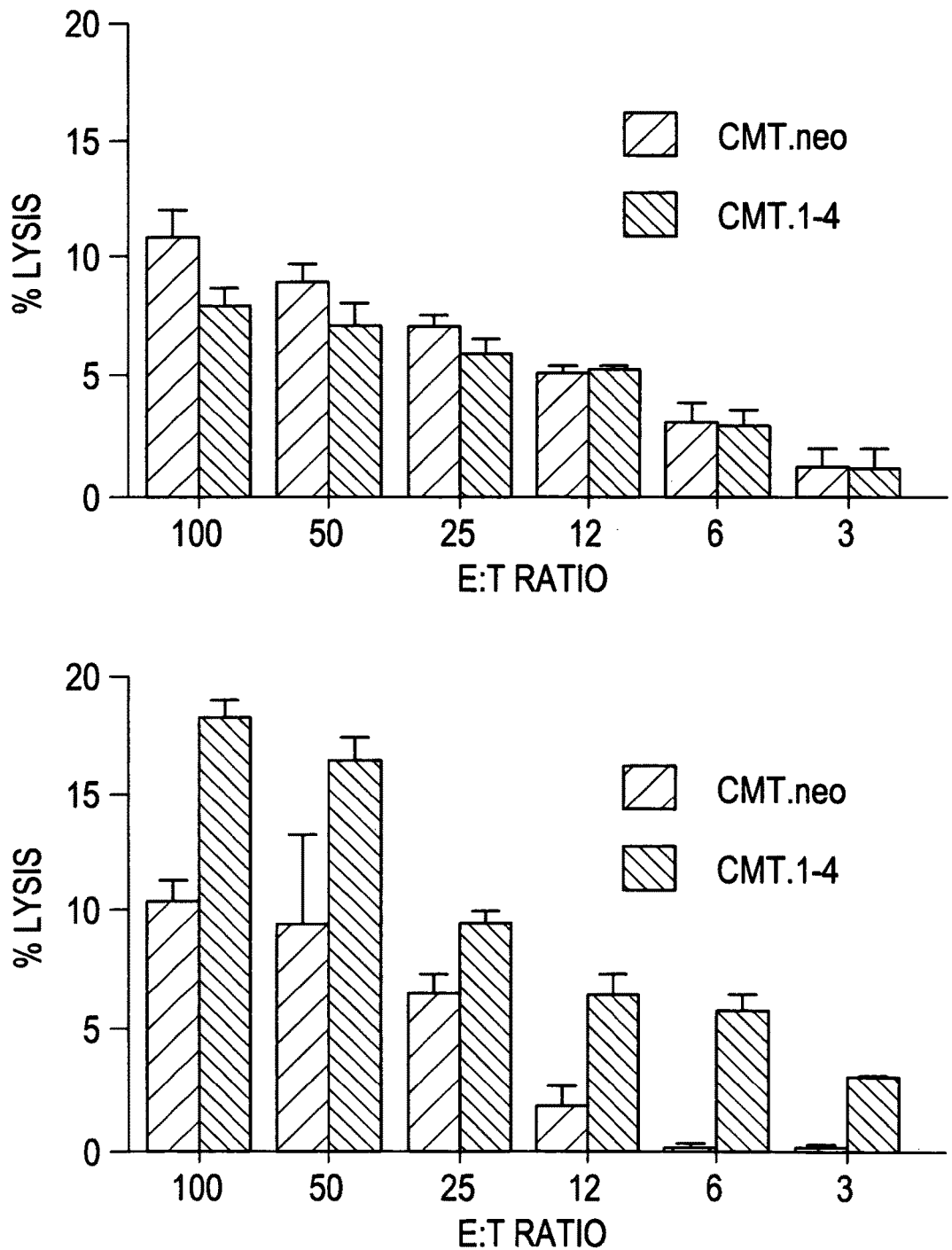

For anti-tumor CTL generation, the specificity of splenocytes was generated by injecting mice intraperitoneally with $1\times10^7$ CMT.neo or CMT.1-4 cells (FIG. 37C). Upon removal the splenocytes were cultured with stimulators at a 3:1 ratio. The stimulators were prepared by incubating CMT1-4 or CMT.neo cells with 30 mg/ml mitomycin C under hypoxic conditions. After incubation of 2 hours the cells were γ-irradiated (10,000 Rads) and washed three times before addition to the splenocyte culture. CMT.neo splenocytes received CMT.neo stimulators, whereas CMT1-4 splenocytes received CMT1-4 stimulators. Six days after in vitro stimulation the splenocytes were tested in a standard 4 hour $^{51}$Cr release assay.

Figure 40A:
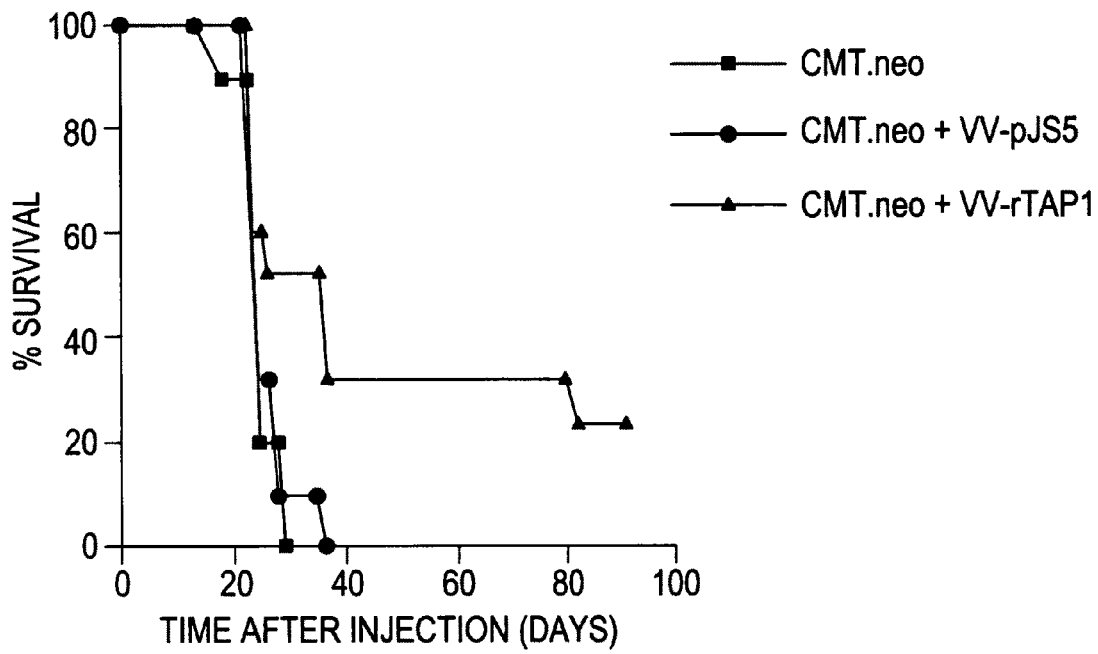
FIG. 40 is graph showing anti-tumor immune therapy by VV-rTAP1. A. Each group of mice were injected ip. with CMT.neo cells. Two out of three groups subsequently received twice treatments of either VV-pJS5 or VV-rTAP1 with 106 pfu in PBS containing 2% mouse serum at 24 hours and at 2 weeks after cell injection. Control group received only PBS containing 2% mouse serum. Statistical analysis shows that VV-rTAP1 treatment of tumor-bearing mice has a significant P-value ($P<0.05$), comparing with both WW-pJS5 and mimic treatment. B. The specificity of splenocytes from two mice injected with CMT.neo and VV-rTAP1 was determined in a chromium release assay against the $^{51}$Cr-labeled targets. CMT.neo, CMT.1-4, and VV-pJS95 infected CMT.1-4 (10:1 m.o.i infection for 3.5 hours).
Figure 40B:
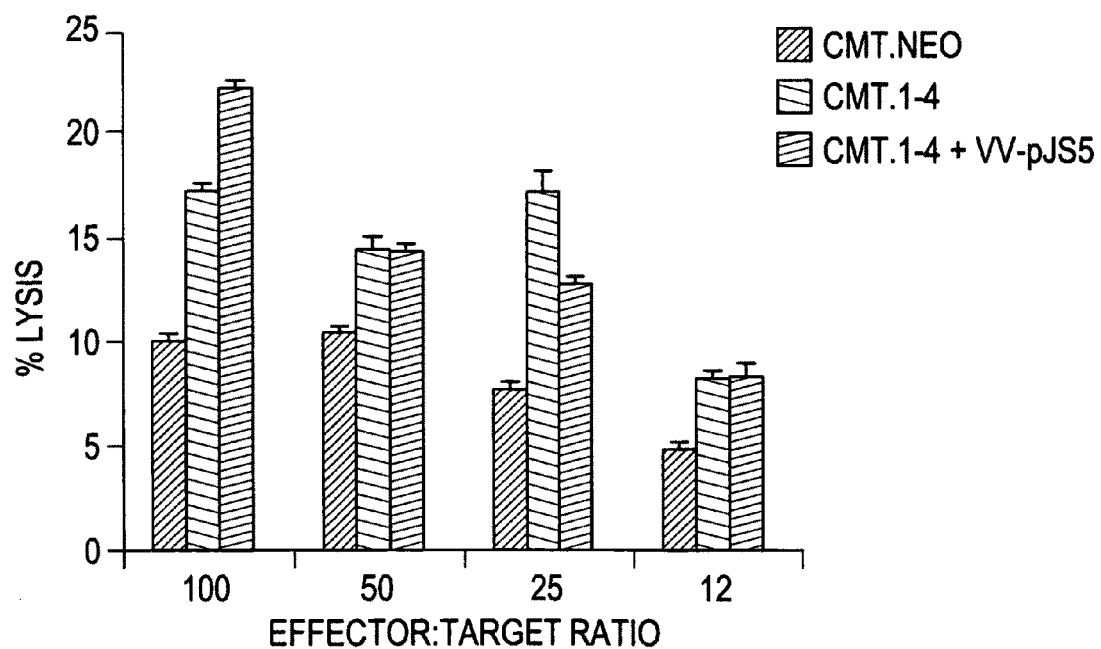

For anti-tumor and VV CTL generation, the specificity of splenocytes was generated by injecting mice intraperitoneally with $1\times10^7$ CMT.neo cells and $1\times10^6$ pfu VV-rTAP1 (FIG. 40B). The splenocytes were a secondary mass culture which were incubated with stimulator cells, plus γ-irradiated (5,000 Rads) naive syngenic splenocytes, at a 5:1:15 ratio. The stimulator cells were prepared by infecting CMT.neo cells with VV-rTAP1 for 3 hours before adding 30 mg/ml mitomycin C under hypoxic conditions. After incubation of 2 hours the cells were γ-irradiated (10,000 Rads) and washed three times before addition to the splenocyte culture. After incubation of six days the splenocytes were tested in a standard 4 hour $^{51}$Cr release assay.

Cytotoxicity Assays

Target cells for the CTL assays were loaded with $^{51}$Cr by incubating $10^6$ cells with 100 (Ci of $^{51}$Cr (as sodium chromate. Amersham) in 250 (I of CTL medium (RPMI-1640 containing 10% HI FBS, 20 mM Hepes) for 1 hour. Following three washes with RPMI, 2% FBS, the target cells were incubated with the effector cells at the indicated ratios for 4 hours. 100 (I of supernatant from each well was collected and the $^{51}$Cr release was measured by a γ-counter (LKB Instruments). The specific $^{51}$Cr release was calculated as follows: [(experimental−media control)/(total−media control)]× 100%. The total release was obtained by lysis of the cells with a 5% Triton-X 100 (BDH) solution.

FACS Assays

Surface expression of the H-2K$^b$ allele was detected by indirect immunofluorescence using the conformational-dependent mouse monoclonal antibodies (mAbs), AF6-88-5.3 (ATCC) and 142.23 (a gift from Dr. Kvist S.), both specific for K$^b$-β$_2$M complexes. Fluorescein isothiocynate-conjugated (FITC) rabbit anti-mouse IgG (Dakopatts, DK) was used as the secondary antibody. The mean logarithmic fluorescence intensity was measured by a FACScan analyzer (Becton and Dickinson, Mountain View, Calif.). Detection of CD4$^+$ T-cells and CD8$^+$ T-cells was used similar protocol as detection of surface MHC class I molecules with minor modification. Briefly, tumors were washed extensively and homogenized into single cells. FITC-conjugated rabbit anti-mouse antibodies (PharMinGen), RM4-5 (against CD4) and 53-6.7 (against CD8) was used.

Western Blots

The proteins of lysates from $5\times10^5$ cells were separated by sodium dodecyl sulfate-polyacrylamide gel electrophoresis (SDS-PAGE) using a 10% resolving gel and then were transferred to a nitrocellulose membrane. The blots were probed with either the rabbit anti-rat TAP1 (D90) or TAP2 (114/2) polyclonal antibody at a dilution of 1:1000 and then incubated with horseradish peroxidase-labelled anti-rabbit antibody at a 1:100,000 dilution. The immunocomplexes were visualized by enhanced chemiluminescence (ECL) according to the instructions of the manufacturer (Amersham, UK) and were quantitatively assessed by a densitometry scan.

Inoculation of Mice with Tumor Cell Lines $5\times10^5$ (otherwise indicated in figure legend) CMT.64 or its transfectants in PBS were injected ip. into C571B1/6 syngeneic mice. For examination of tumor-growth pattern, one representative mouse from each group (4 mice for each group) was sacrificed after one month and photographing in vivo tumors (FIG. 37A). For mice survival experiments, each group contained 15 (FIG. 37B) or 10 (FIGS. 39B and 40A) mice.

Statistics

The statistics for the cancer studies were performed using the Kaplan-Meier log rank survival test or Regression log percentage survival test prior to carry out a paired t-test. The computer software program JMP IN version 3.2.1 (SAS Institute Inc. (1989-97, Duxbury Press, NC. USA). was used to do the computations. The data was considered statistically different if p<0.05.

Results and Discussion

Phenotype of TAP transfectants

Figure 36A:
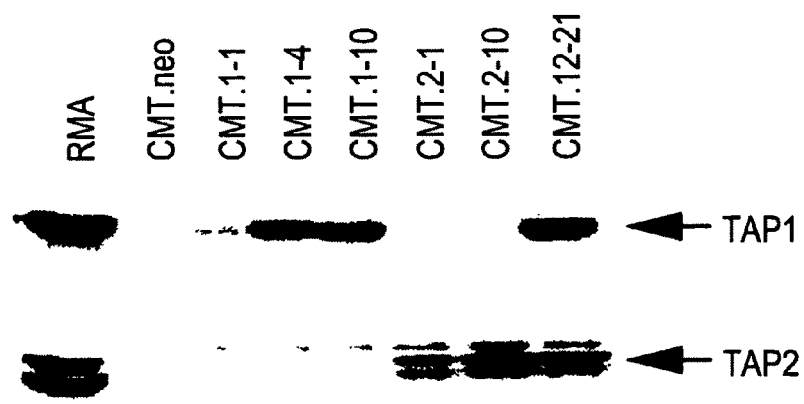
FIG. 36 shows the increase of CMT.64 antigenicity by transfection with TAP1 but not TAP2. A. rTAP1 and rTap2 expression of the transfectants are shown by Western blots. B. Target cells pulsed with VSV-Np peptide with indicated concentrations for 1 hour following performing cytotoxicity assay. 50:1 E:T ratio is shown. C. Target cells were infected with 1:10 m.o.i. VSV overnight prior to examination of antigen presentation capacity with a $^{51}$Cr-release assay. 100:1 ratio is shown.

The phenotype of the CMT.64 cell line has been previously described (44). Transfection of rat-TAPs (rTAP) into this cell line partially restores expression of relevant components in MHC class I-restricted antigen presentation pathway. FIG. 36A shows transfectants expressing rTAP proteins. Two rTAP1-transfectant clones. CMT.1-4 and CMT.1-10, and one rTAP1,2-transfectant. CMT.12-21, express higher levels of rTAP1 protein than the CMT.1-1 clone (one of rTAP1 clone). In comparison with RMA cells, these transfectants reveal a similar rTAP1 expression level (except CMT.1-1): CMT.1-1 express 10-times less, CMT.1-4 and CMT.1-10 express 2.5-times less, and CMT.12-21 expresses 2-times less. The rTAP2 expression levels in the transfectants were also examined in relation to RMA: CMT.2-1 and CMT.2-10 (two rTAP2 transfectant clones) express 4-times and 2-times less respectively, and CMT.12-21 2-times less. Thus, in comparison to RMA all rTAP transfectants, except CMT.1-1, express similar levels of rTAP proteins.

Figure 36B:
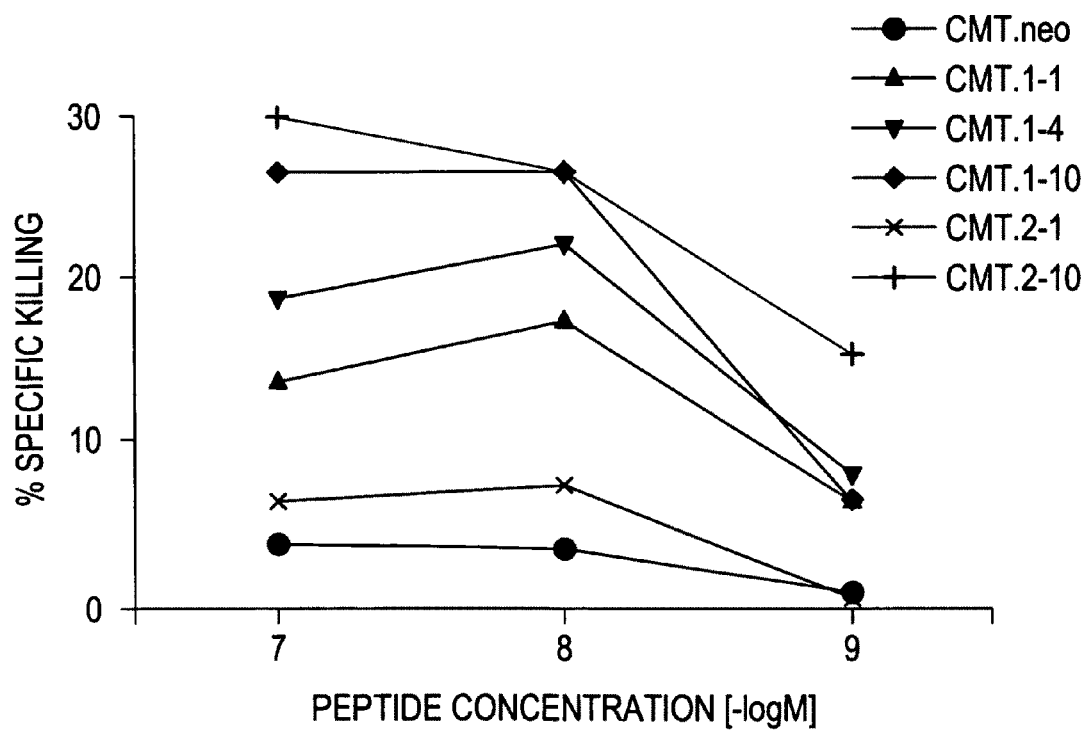

TAP supplies peptides for MHC class I binding and surface expression. Therefore, the inventors examined MHC class I expression on surface of transfectants by FACS analysis. Although TAPs were introduced into the CMT.64 cells, surface expression of MHC class I did not dramatically increase (Table 4), as judged by comparison to IFN-γ treated CMT.64 cells which restored high levels of MHC class I expression. This suggests that downregulation of MHC class I in CMT.64 cells likely occurs at the transcriptional level. However, constitutive expression of TAP rescues some surface MHC class I expression (Table 4). It is noteworthy that these levels of MHC class I expression on surface of TAP-transfectant clones quantitatively predict antigenic peptide binding. Cells pulsed with the immunodominant peptide derived from vesicular stomatitis virus nucleoprotein (VSV-Np) were killed equally well in a cytotoxic CTL assay, demonstrating that functional amounts of MHC class I are expressed on all transfectants, except CMT.neo and CMT.2-1 (FIG. 36B).

Figure 36C:
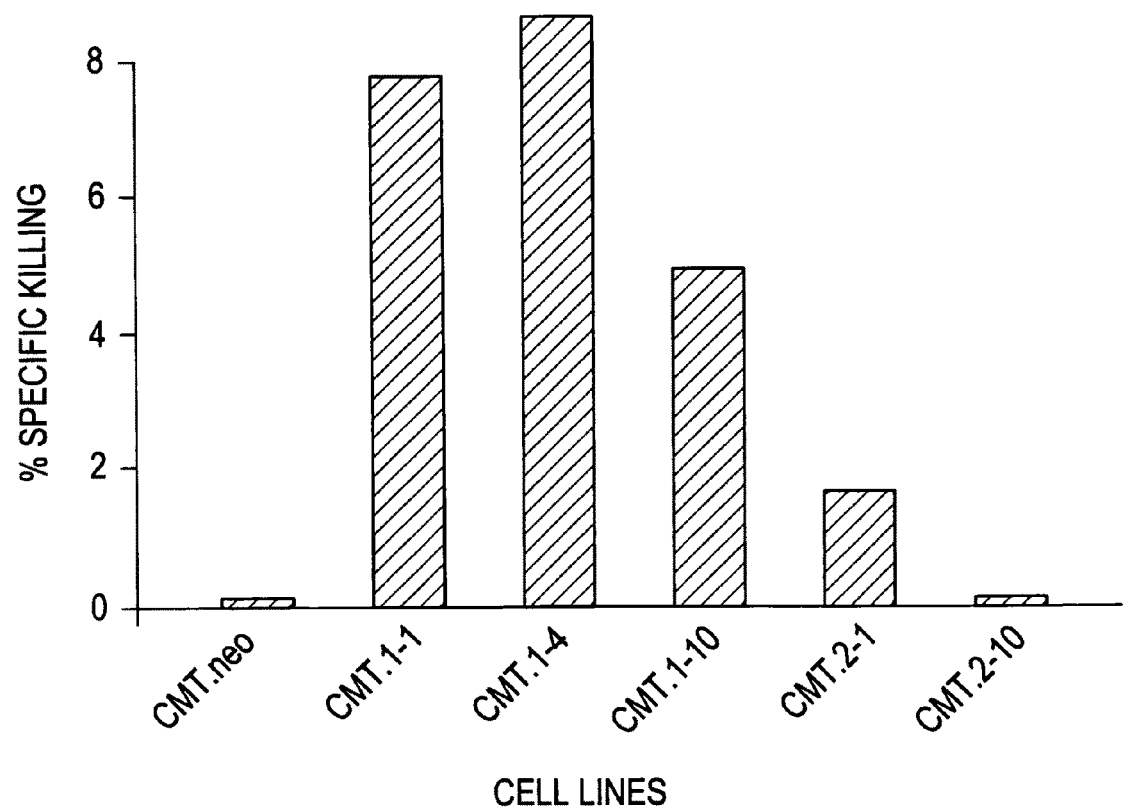

It is well known that the presentation of endogenously-generated antigenic peptides to the cell surface for CTL recognition requires that peptides have the capacity to be transported by TAP and to bind to relevant MHC class I. An additional requirement is there be sufficient quantities of peptides generated in the cytosol. Peptide-pulse experiments only indicate whether surface MHC class I expression for CTL recognition is sufficient but do not confirm the overall antigen presentation capacity. Thus, the inventors infected transfectants with VSV at 10:1 m.o.i overnight and performed cytotoxicity assays. In FIG. 36C, the results demonstrated that three clones of rTAP1 transfectant were able to present the immunodominant epitope. VSV-Np, while two rTAP2 clones and CMT.neo were unable to present this epitope efficiently. In a separate experiment, a clone transfected with rTAP1.2. CMT.12-21, also presented this epitope efficiently (data not shown). Our results suggest that only rTAP1 or rTAP1 and 2, but not rTAP2 transfected clones increase their antigenicity and acquire the ability to process and present foreign antigens. This difference cannot be attributed to levels of rTAP2 expression, since all TAP transfectants, except CMT.1-1 clone, express similar levels of TAP1 and/or TAP2 compared with RMA-TAPs. Taken together, antigen presentation appears to largely depend on TAP1 function or TAP1,2 heterodimer function in CMT.64 transfectants.

TAP1 Improves Immune Recognition of Tumors In Vivo

Since in vitro experiments provide evidence that rTAP is able to improve specific CTL recognition, these results could be applied the immunosurveillance against tumors in vivo. To examine this, the inventors first tested if the host immune system could control the growth of CMT.64 transfectants. Mice were injected with CMT.neo or rTAP-transfected cells. On day 30 after injection, one representative mouse from each group was sacrificed in order to examine tumor-growth pattern. The results are depicted in FIG. 37A. Two rTAP2 transfected cell lines. CMT.2-1 and CMT.2-10 (see FIG. 37A-II, one example), had a tumor-growth pattern identical to control tumor, CMT.neo (FIG. 37A-I). Interestingly, in rTAP1 or rTAP1.2 transfectants, either tumors grew to form one large tumor (CMT.1-1 and CMT.1-10) (FIG. 37A-II, one example) or no tumor was present (CMT.1-4 and CMT.12-21) (FIG. 37A-IV, one example). Furthermore, on day 60, CMT.1-4 tumor had a tumor-growth pattern the same as the other rTAP1-transfected clones (data not shown). These results suggest that tumors with rTAP1 or rTAP1 and 2 have a limited tumor foci or are absent while rTAP2-transfected tumors have the same level of metastasis as the wild-type tumors. This is true for other tumor-bearing mice (data not shown).

In a subsequent set of experiments, the inventors addressed whether or not immune recognition of TAP1-transfected tumors could prolong the survival of tumor-bearing animals. FIG. 37B depicts two independent experiments and summarizes the survival rates of mice injected ip. with CMT.64, or rTAP1- or rTAP2-transfected clones. At day 40-42 post injection, 50% of CMT.64 and CMT.2-10 tumor-bearing group mice had died (FIG. 37B top), and statistical analysis demonstrated no difference between these two groups (P=0.210>>0.05). In contrast, after 100 days 60% of the CMT.1-4 group mice were still alive (P<<0.001) (FIG. 37B top). To confirm increased survival is not due to variation of rTAP1-transfected clones, in a repeated experiment with other clones, the inventors also confirmed protection in another rTAP1 expressing clone (P<0.05) but not rTAP2 (P>0.05) (FIG. 37B bottom). This demonstrates that this effect is not specific to a single TAP1-expressing clone. Autopsied examination of all dead mice shown in FIG. 37B exhibited the patterns noted above (data not shown). As an experimental control, no difference was observed between CMT.64 and CMT.neo cell lines (date not shown). Our results suggest that improvement of the survival rates of rTAP1-tumor-bearing mice may be due to enhancement of tumor's immunogenicity and, therefore, that triggers the anti-tumor immune response of the hosts.

The Nature of Tumor Recognition

Figures 38A, 38B:
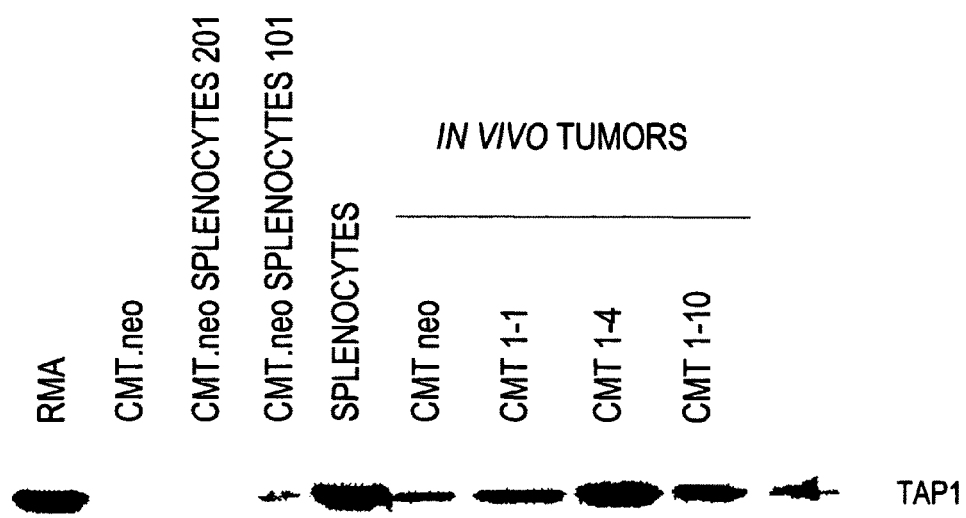
FIG. 38 shows the percentage of tumor-infiltrating lymphocytes and TAP1 expression within growing tumors in mice. A. CD4 and CD6 T-cells in tumors were detected by FACS analysis using monoclonal antibodies. RM4-5 (against CD4) and 53-6.7 (against CD8). a—%=100%×Number of CDs/Number of total cells (including tumor cells). b. TAP1 expression in vivo tumors or cell lines was detected by Western blot using C90 rabbit serum specific for rate and mice TAP1.

T cells are critical factors in the defense against the development of most tumors. The presence of lymphocytic infiltrates within many malignant tumors has been argued as an indication of an in vivo anti-tumor immune response (46). Since in vivo protection from rTAP1-tumors is controlled by the host immune system, the percentage of tumor-infiltrating lymphocytes (TILs) was compared between different tumors. The inventors examined TILs in animals one month or two months after injection of CMT.64 transfectants using flow cytometry. The results are shown in FIG. 38A. The ratio of $CD4^+$ and $CD8^+$ T cells were enhanced by two to eight times in rTAP1-tumors compared with control. CMT.neo, and rTAP2-tumors.

Increases of TIL in TAP1-tumors suggests the presence of specific cytolytic-T cells. This possibility is based on three lines of evidence; 1) TAP1 increases tumor surface MHC class I, 2) TAP1 improves antigen presentation, 3) TAP1 results in tumors being controlled in vivo and improves animal survival. If CMT.64 cells contain a tumor-associate antigen (TAA), then specific CTLs should be generated by antigen presentation in rTAP1-transfectants in vivo. CTL analysis was performed using splenocytes from mice immunized with CMT.neo or CMT.1-4. CMT.neo-stimulated and CMT.1-4-stimulated splenocytes were compared against CMT.neo and CMT.1-4 targets in a standard $^{51}Cr$-release assay. Splenocytes from CMT.1-4-immunized mice were much better than splenocytes from CMT.neo-mice at killing target cells (FIG. 37C). Killing of CMT.neo and CMT1-4 targets by CMT.neo-splenocytes was equivalent (FIG. 37C left-panel). In contrast, killing by CMT.1-4 stimulated splenocytes of CMT.1-4 targets was enhanced at both high and low E:T ratios (FIG. 37C right-panel). These results suggest that CMT.1-4 cells contain an antigenic antigen(s). TAA, and this antigen can be presented by TAP1-expressing tumors, triggering host T cell recognition.

Figure 39A:
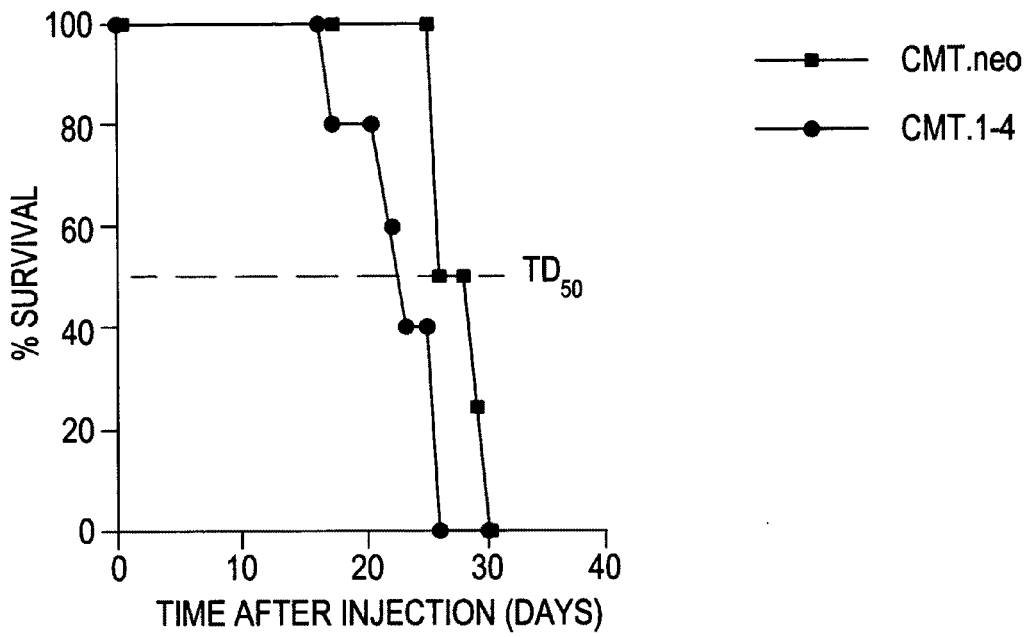
FIG. 39 is bar graph showing the examination of the survival of mice bearing CMT tumors. A rTAP1 does not improve recognition of CMT.64 in nude mice. $5 \times 10^5$ cells of either CMT1-4 (5 mice) or CMT.neo (4 mice) were injected ip. To nude mice ($H\text{-}2^b$). The time of mortidity was recorded for each group. B. Immunization with rTAP-transfected tumors improves the survival of CMT.64-bearing mice. $1 \times 10^7$ cells of either CMT.neo, CMT.1-4 or CMT.1-10 were treated with Mitomycin C (30 mg/ml) for 2 hours and γ-irradiated (10,000 Rads) before injection ip. into 10 C57B1/6 mice. One month later the mice were challenged ip. with $5 \times 10^5$ CMT.64 cells in PBS. The time of morbidity was recorded.

The importance of T cells in anti-tumor immunity has been further confirmed by using athymic mice, which are devoid of T lymphocytes (46). Unlike wild-type animals, the survival rates of athymic mice were not significantly different between CMT.neo- and CMT.1-4-bearing mice groups (FIG. 39A).

Figure 39B:
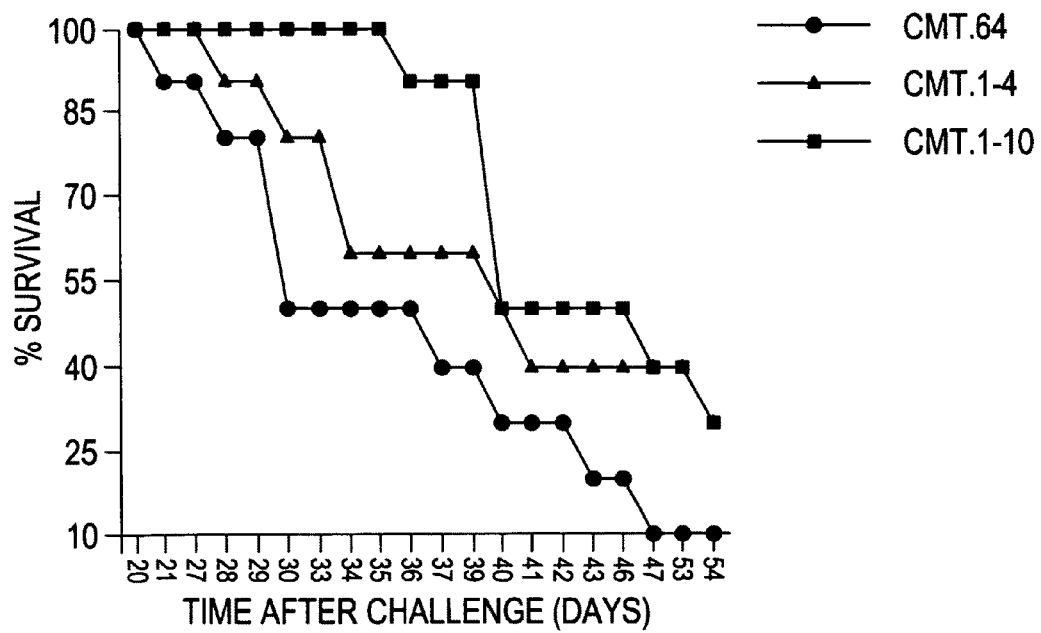

Immunization with rTAP1-Transfected Cells Affords Protection Against Wild-Type Tumor Cells The inventors have confirmed that rTAP1-transfected cells possess antigenicity and immunogenicity. The inventors were interested to test whether or not immunization with TAP1-positive cells affords protection against TAP-deficient CMT.64 cells. Three groups of mice were immunized ip. with mitomycin- and irradiation-treated cells, CMT.neo, CMT.1-4 and CMT.1-10, respectively. One month later the mice were challenged ip. with wild-type cells. CMT.64 and then monitored for survival. The results are shown in FIG. 39B. Mice immunized with both immunogenic rTAP1-transfected clones show a successful challenge with TAP-negative CMT.64, compared with CMT.neo immunization. A statistic analysis of regression logarithmic percentage survival showed this effect to be significant; P<0.001 for CMT.1-10 immunization, and P<0.05 for CMT.1-4 immunization.

Successful challenge of wild-type tumors following immunization with rTAP1 but not CMT.neo tumor cells suggests that the immunization with immunogenic tumors can augment the anti-tumor response. Obviously, specific T cells participate in this immune response. Although it is not clear how T cells, especially CTLs, directly recognize wild-type CMT.64 cells, in vivo they, along with other immune elements, may compose the integral components of the specific anti-tumor response.

Analysis of rTAP1 Expression in In Vivo Growing-Tumors

At this point it became of interest to examine if the rare large tumors of the TAP1 transfectants had become TAP-negative revertants selected by the pressure of the host immune system. A Western blot analysis was performed on the rTAP1-tumors that had grown in mice for one month or two months. Tumors, in vivo, contain normal mouse cells (such as CD4 and CD8 T cells etc) which express mouse TAPs. Our TAP1 specific antibody recognizes both mouse and rat TAP1 and it was initially very difficult to judge the expression of rTAP1 in these solid tumors. The inventors, therefore, included controls that consisted of mixing CMT-.neo cells with 20:1 or 10:1 ratio of the wild-type splenocytes from the mice. The results are shown in FIG. 38B. The CMT-.neo tumor contained a stronger TAP1 signal than the CMT-.neo:splenocytes mixture at 10:1 ratio, suggesting other types of wild-type mouse cells, excluding T cells (CMT.neo tumor contains ~1% T cells, see FIG. 38A), had infiltrated into the tumor. As expected, in comparison with rTAP1-tumors' signal. CMT.neo-tumor's signal was much less (see FIG. 38B). Although it cannot be judged whether the amount of mouse wild-type infiltrating cells induced the differences of levels of TAP expression between CMT.neo-tumor and rTAP1-tumor clones (CMT.1-1 and CMT.1-10), the intensity as judged by gel scanning of TAP1 in CMT.1-4 tumor is identical to that in RMA cells. Since the CMT.1-4 cells express half the amount of rTAP1 protein compared to the RMA cells (see FIG. 36A) and this tumor, in vivo, contains less T cells than CMT.1-10-tumor (see FIG. 38A) (suggesting less contamination by wild-type infiltrating cells), the inventors conclude that the TAP transfected tumors maintain the expression of rTAP1 during two month's growth in vivo.

Our data supported the conclusion that the large tumors are not TAP revertants but also implied a more interesting possibility. The TAP1 levels between the different TAP-expressing clones generally appeared to affect the malignancy of the tumor. The more TAP-1 expressed, the fewer the number of tumors observed. These data lead us to speculate that the reason the inventors see some large tumors in the TAP1 expressers is because the TAP1 expression levels are too low to provide complete protection. Alternatively, in a naive mouse the initial tumor burden has formed a solid foci leading to a late stage metastatic carcinoma that is unable to be controlled by a specific anti-tumor immune response. The latter possibility is supported by our results which showed that all surviving mice which were initially challenged with live rTAP1- or rTAP1,2-tumor cells (non-irradiated) remained healthy after subsequent challenge with rTAP1-tumor cells (data not shown).

Contribution of TAP1 to Cancer Therapy

The inventors have shown that TAP1 improves CMT.64 immunogenicity and host survival rates. This has led us to explore whether TAP1 can form the basis of a tumor immunotherapy. An expression vector of recombinant vaccinia virus carrying rTAP1 gene (VV-rTAP1) was generated for these experiments. A faithful model for viral therapy for tumor-burdened individuals entails infection in vivo after the tumor load had been established. To examine this scenario, $5 \times 10^5$ CMT.neo cells were injected into three mouse groups. After 24 hours, mice received either $10^6$ pfu VV-rTAP1, VV-pJS5 (control vector) or PBS containing 2% C57B1/6 mouse serum. This procedure was performed again at 2 weeks. As expected, the vector only. VV-pJS5 did not increase mice survival, as judged by comparison to the PBS-group (P=0.18>>0.05) (see FIG. 40A). However, the mice receiving VV-rTAP1 treatment had a significantly higher survival rate, as judged by comparison to the PBS-group (P=0.01<<0.05) and the VV-pJS5 group (P=0.04<<0.05) (see FIG. 40A).

The inventors sought to confirm that the improved survival rate of tumor-bearing mice was due to the host immune system recognizing antigens, including tumor antigens, after VV-rTAP1 infection. CTL analysis was performed by using the splenocytes from mice injected with CMT.neo+VV-rTAP1. The targets were CMT.neo. CMT.1-4 and CMT.1-4 infected with 10:1 m.o.i VV-pJS5. If the splenocytes contained TAA-specific CTLs then it would kill CMT.1-4 targets and, therefore, have confirmed the presentation in vivo of tumor antigens in VV/rTAP1 infected CMT.neo. The results are shown in FIG. 40B. In comparison with control CMT.neo, CMT.1-4 targets were killed more efficiently. This suggests tumor antigens are presented in VV-rTAP1 infected CMT.neo tumors in vivo. The inventors conclude that the improved survival is due to the presentation of both tumor and VV antigens after the viral therapy.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

TABLE 1: Peptides (p), h$\beta_2$M ($\beta_2$M), and IFN-$\gamma$ (IFN) Treatment Modifies the Conformation of K$^b$ and D$^b$ expressed on the cell surface of RMA, RMA-S, and CMT.64 Cells.

| | Treatment | | | Antibodies | | |
|---|---|---|---|---|---|---|
| | | | | 142-23.3 | 28-11-5s | BBM.1 |
| Cell lines | IFN 12 | p | $\beta_2$M | K$^b$ spec. | D$^b$ spec, | h$\beta_2$m spec. |
| | | | | Arbiwary fluorescence units | | |
| Experiment 1 | | | | | | |
| CMT 64 | − | − | − | 5 | 3 | ND |
| | − | + | + | 8 | 5 | ND |
| | + | − | − | 26 | 58 | ND |
| | * | + | + | 35 | 53 | ND |
| Experiment 2 | | | | | | |
| RMA | + | − | − | 346 | 430 | 6 |
| | + | + | − | 606 | 449 | 4 |
| | + | − | + | 438 | 549 | 406 |
| | + | + | + | 780 | 515 | 606 |
| RMA-S | + | − | − | 12 | 4 | 14 |
| | + | + | − | 10 | 1 | 14 |
| | + | − | + | 10 | 2 | 76 |
| | + | + | + | 41 | 2 | 262 |

TABLE 1-continued

TABLE 1: Peptides (p), hβ$_2$M (β$_2$M), and IFN-γ (IFN) Treatment Modifies the Conformation of K$^b$ and D$^b$ expressed on the cell surface of RMA, RMA-S, and CMT.64 Cells.

| Cell lines | Treatment | | | Antibodies | | |
|---|---|---|---|---|---|---|
| | IFN 12 | p | β$_2$M | 142-23.3 K$^b$ spec. | 28-11-5s D$^b$ spec. | BBM.1 hβ$_2$m spec. |
| | | | | Arbiwary fluorescence units | | |
| Experiment 3 | | | | | | |
| RMA | – | – | – | 164 | 173 | 1 |
| | – | + | + | 242 | 182 | 274 |
| RMA-S | – | – | – | 12 | 2 | 1 |
| | – | + | + | 70 | 2 | 86 |

TABLE 2

Effect of TAP 1 and TAP 2 on Tumor Survival
Mice were injected with CMT.64, or CMT.12.12 cells ip at 2 × 10$^5$ and 5 × 10$^5$ cells per mouse. The cell lines were resuspended in PBS prior to inoculation into recipient mice.
Preliminary Results

| | CMT.64 SurvJtotal | CMT12.12 survJtotal |
|---|---|---|
| 2 × 10$^5$ | 015 | 2/5 |
| 5 × 10$^5$ | 1/4* | 515 |

*One of the mice was sacrificed and an autopsy clearly revealed the presence of a solid tumor at the site of injection. Furthermore, all mesenteric lymph nodes were grossly enlarged.

TABLE 3

AUTOPSY TUMOR RESULTS FROM CMT.64, CMT.12.12 EXPT. #1

| | C57BL/6 CMT.64 | CMT.12.12 | PBS | Balb/C CMT.64 | CMT.12.12 |
|---|---|---|---|---|---|
| #Mice/exp. | 20 | 20 | 5 | 19 | 20 |
| Survived 90 Days | | 2-none 1-type A | 5-none | 13-none 1-type A | 20-none |
| Died Before 90 Days | 20-type B | 17-type B | | 4-type A 1-? | |

TABLE 4

Comparison of MHC class I expression on surface of the CMT-TAP transfectants

| Cell line | D$^b$ | K$^b$ |
|---|---|---|
| CMT.64 | 18 | 0 |
| CMT.neo | —* | 0.1 |
| CMT.1-1 | — | 62 |
| CMT.1-4 | 164 | 64 |
| CMT.1-10 | 68 | 36 |
| CMT.2-1 | 10 | 3 |
| CMT.2-10 | 39 | 48 |
| CMT.12-21 | 103 | 22 |
| CMT.64 + IFN-γ | 1100 | 590 |

Surface expression of D$^b$ and K$^b$ molecules was performed on the CMT.64 and its TAP transfectants by FACS analysis. The monoclonal antibodies, Y-3 against K$^b$ and 28.14.8.S against D$^b$ were used in this assay. The results are normalized by substracting immunofluorescence intensity of negative controls from each results.
*not done.

FULL CITATIONS FOR REFERENCES REFERRED TO IN THE SPECIFICATION

1. Suh, W.-K., M. F. Cohen-Doyle, K. Fruh, K. Wang, P. A. Peterson and D. B. Williams. 1994. Interaction of MHC class I molecules with the transporter associated with antigen processing. Science 264:1322.
2. Ortmann, B., M. J. Androlewicz and P. Cresswell. 1994. MHC class I/b2-microglobulin complexes associate with TAP transporters before peptide binding. Nature 368:864.
3. Van Bleek, G. M. and S. G. Nathenson. 1990. Isolation of an endogenously processed immunodominant viral peptide from the class I H-2 Kb molecule. Nature 348:213.
4. Fremont, D. N., M. Matsumura, EA. Stura, P. A. Peterson and I. A. Wilson. 1992. Crystal structures of two viral peptides in complex with murine MHC class I H-2 Kb. Science 257:919.
5. Kundig, T. M., A. Althage, H. Hengartner and R. M. Zinkernagel. 1992. Skin test to assess virus-specific cytotoxic T-cell activity. Proc. Natl. Acad. Sci. USA 89:7757.
6. Rotzschke, O., K. Falk, K. Deres, H. Schild, M. Norda, J. Metzger, G. Jung and H.-G. Rammensee. 1990. Isolation and analysis of naturally processed viral peptides as recognized by cytotoxic T cells. Nature 348:252.
7. Byrne, J. A. and M. B. A. Oldstone. 1984. Biology of cloned cytotoxic T lymphocytes specific for lymphocytic choriomeningitis virus: clearance of virus in vivo. J. Virol. 51:682.
8. Harty, J. T. and M. J. Bevan. 1992. CD8+ T cells specific for a single nonamer epitope of *Listeria monocytogenes* are protective in vivo. J. Exp. Med. 175:1531.
9. Feltkamp, M. C. W., M. P. M. Vierboom, W. M. Kast and C. J. M. Melief. 1994. Efficient MHC class I-peptide binding is required but does not ensure MHC class I-restricted immunogenicity. Mol. Immunol. 31:1391.
10. Weidt, G., O Utermohlen, J. Zerrahn, J. Reimann, W. Deppert and F. Lehmann-Grube. 1994. CD8+ T lymphocyte-mediated antiviral immunity in mice as a result of injection of recombinant viral proteins. J. Immunol. 153:2554.
11. Hosken, N. A. and M. J. Bevan. 1992. An endogenous antigenic peptide bypasses the class I antigen presentation defect in RMA-S. J. Exp. Med. 175:719.
12. Takahashi, H., T. Takeshita, B. Morein, S. Putney, R. N. Germain and J. A. Berzofsky. 1989. Induction of CD8+ cytotoxic T cells by immunization with purified HIV-1 envelope protein in ISCOMs. Nature 344:873.
13. Townsend, S and J. P. Allison. 1993. Tumour rejection after direct costimulation of CD8+ T cells by B7-transfected melanoma cells. Science 259:368.
14. Chen, L. P., S. Ashe, W. A. Brady, I. Hellstrom, K. E. Hellstrom, J. A. Ledbetter, P. McGowan and P. S. Linsley. 1992. Costimulation of anti-tumour immunity by the B7 counter receptor for the T lymphocyte molecules CD28 and CTLA 4. Cell 71:1093.
15. Hughes, H. P. A., M. Campos, D. L. Godson, Van Drunen, S. Littel-Van Den Hurk, L. McDougall, N. Rapin, T. Zamb and L. A. Babiuk. 1991. Immunopotentiation of Bovine Herpes Virus subunit vaccination by interleukin-2. Immunol. 74:461.
16. Flexner, C., B. Moss, W. T. London and B. R. Murphy. 1990. Attenuation and immunogenicity in primates of vaccinia virus recombinants expressing human interleukin-2. Vaccine 8:17.
17. Heath, A. W. and J. H. L. Playfair. 1992. Cytokines as immunological adjuvants. Vaccine 10:427.

18. Meuer, S. C., H. Dummann, K. H. Meyer Zum Buschenfelde and H. Kohler. 1989. Low-dose interleukin-2 induces systemic immune responses against HBs antigen in immunodeficient non-responders to hepatitis B vaccination. Lancet. 1:15.
19. Miller, M. A., M. J. Skeen and H. K. Ziegler. 1995. Nonviable bacterial antigens administered with IL-12 generate antigen-specific T cell responses and protective immunity against *Listeria monocytogenes*. Immunol. 155: 4817.
20. Cox, J. C. and A. R. Couler. 1997. Adjuvants-a classification and review of their modes of action. Vaccine 15:248.
21. Melnick, J. L. 1989. Viral vaccines: Achievements and challenges. Acta Virol. 33:482.
22. Arnon, R. and R. J. Horwitz. 1992. Synthetic peptides as vaccines. Cur. Op. in Immunol. 4:449.
23. Dertzbaugh, M. T. 1998. Genetically engineered vaccines: an overview. Plasmid 39:100.
24. Lee, H. M., T. L. Timme, and T. C. Thompson. 2000. Resistance to lysis by cytotoxic T cells: a dominant effect in metastatic mouse prostate cancer cells. Cancer Res. 60:1927-33.
25. Seliger B, Wollscheid U. Momburg F. Blankenstein T, Huber C. Characterization of the major histocompatibility complex class I deficiencies in B16 melanoma. Cancer Research, 16(3): 1095-9, 2001.
26. Alimonti J, Zhang Q J, Gabathuler R, Reid G. Chen S. Jefferies W A. TAP expression provides a general method for improving the recognition of malignant cells in vivo. Nature Biotechnology, vol 18, pp 515-520, May 2000.
27. Tanaka, K., Isselbacher, K. J., Khoury, G. & Jay, G. Reversal of oncogenesis by the expression of a major histocompatibility complex class I gene. Science 228, 26 (1985).
28. Wallid, R. et al. Abrogation of metastatic properties of tumour cells by de novo expression of H-2K antigen following H-2 gene transfection. Nature 315, 301-305 (1985).
29. Seliger, B., Maeurer, M. J. & Ferrone, S. TAP off-Tumors on. Immunol. Today 18, 292 (1997).
30. Garrido, F. et al. Implications for immunosurveillance of altered HLA class I phenotypes in human tumours. Immunol. Today 18, 89 (1997).
31. Hammerling, G. J., Klar, D., Pulm, W., Momburg, F. & Moldenhauer, G. The influence of major histocompatibility complex class I on tumor growth and metastasis. Biochimica et Biophisica Acta 907, 245 (1987).
32. Singel, D. P., Ye, M. & X., O. Molecular basis for lack of expression of HLA class I antigen in human small-cell lung carcinoma cell lines. Int. J. Cancer 68, 629 (1996).
33. Braciale, T. J. & Braciale, V. L. Viral antigen presentation and MHC assembly. [Review]. Seminars in Immunology 4, 81-84 (1992).
34. Rammensee, H. G. Antigen presentation—recent developments. [Review]. International Archives of Allergy & Immunology 110, 299-307 (1996).
35. Momburg, F., Roelse, J., Neefjes, J. & Hammerling, G. J. Peptide transporters and antigen processing. [Review]. Behring Institute Mitteilungen (1994).
36. Neefjes, J. J., Schumacher, T. N. & Ploegh, H. L. Assembly and intracellular transport of major histocompatibility complex molecules. [Review]. Current Opinion in Cell Biology 3, 601-609 (1991).
37. Cromme, F. V. et al. Loss of transporter protein, encoded by the TAP-1 gene, is highly correlated with loss of HLA expression in cervical carcinomas. Journal of Experimental Medicine 179, 335-340 (1994).
38. Maeurer, M. J. et al. Tumour escape from immune recognition: lethal recurrent melanoma in a patient associated with downregulation of the peptide transporter protein TAP-1 and loss of expression of the immunodominant MART-1/Melan-A antigen. J. Clin. Invest. 98, 1633 (1996).
39. Seliger, B. et al. Expression and function of the peptide transporters in escape variants of human renal cell carcinomas. Exp. Hematol. 25, 608 (1997).
40. Wang, R. F. & Rosenberg, S. A. Human tumor antigens recognized by T lymphocytes: implications for cancer therapy. J. Leuk. Biol. 60, 296-309 (1996).
41. Franks, L. M., Carbonell, A. W., Hemmings, V. J. & Riddle, P. N. Metastasizing tumors from serum-supplemented and serum-free cell lines from a C57B1 mouse lung tumour. Cancer Res. 36, 1049 (1976).
42. Klar, D. & Hammerling, G. J. Induction of assembly of MHC class I heavy chains with $b_2$-microglobulin by interferon-gamma. EMBO 8, 475 (1989).
43. Jefferies, W. A., Kolaitis, G. & Gabathuler, R. IFN-γ-induced recognition of the antigen-processing variant CMT.64 by cytolytic T cells can be replaced by sequential addition of $b_2$-microglobulin and antigenic peptides. J. Immunol. 151, 2974-2985 (1993).
44. Gabathuler, R., Reid, G., Kolaitis, G., Driscoll, J. & Jefferies, W. A. Comparison of cell lines deficient in antigen presentation reveals a functional role for TAP-1 alone in antigen processing. J. Exp. Med. 180, 1415-1425 (1994).
45. Reid, G. S. D. Functional relevance and structural requirements of peptide transport in a murine carcinoma cell line. PhD. Thesis, Biotechnology Laboratory, UBC, Vancouver, Canada. (1997).
46. Vose, B. M. & Moose, M. Human Tumor-infiltrating Lymphocytes: a Marker of Host Response. Semin Haematol 22, 27-40 (1985).
47. Inglis, J. R. T Lymphocyte Today. Elsevier Science Publisher, Amsterdam (1983).

We claim:

1. A method of enhancing a cytotoxic T-lymphocyte response in an animal to viral antigens in cells expressing low to non-detectable levels of peptide/MHC molecules on the cell surface, comprising administering to said animal at a location at nor near the cells a vector encoding a TAP-1 and a TAP-2 molecule in a manner which causes uptake of the vector by the cells resulting in expression of TAP-1 and TAP-2 in said cells, and co-administering to said animal at a location at or near the cells a vector encoding a viral antigen, thereby enhancing the cytotoxic T-lymphocyte response in said animal to said viral antigen.

2. The method of claim 1 wherein the viral antigens are selected from the group consisting of VSV, influenza, sendai, HIV, hepatitis B, hepatitis C and human papilloma virus E6 and E7 antigens.

3. The method of claim 2 wherein the viral antigen is VSV or influenza.

4. The method of claim 1 wherein the animal is a human.

5. The method of claim 1, wherein the viral antigen is an influenza antigen, and wherein the method is used to treat a patient having, or at risk of contracting, influenza.

6. The method of claim 1 wherein the vectors are administered in conjunction with another therapeutic agent effective against the viral antigen.

7. The method of claim 1 wherein one or both of the vectors is a viral vector.

8. The method of claim 7 wherein the viral vector is selected from the group consisting of vaccinia based vectors, adenovirus based vectors, lenti virus based vectors and HSV based vectors.

9. The method of claim 1 wherein one or both of the vectors is a plasmid vector.

10. A method of enhancing a cytotoxic T-lymphocyte response in an animal to VSV antigens in cells expressing low to non-detectable levels of peptide/MHC molecules on the cell surface, comprising
  introducing into said cells in said animal a vector encoding a TAP-1 and a TAP-2 molecule in a manner which causes uptake of the vector by the cells resulting in expression of TAP-1 and TAP-2 in said cells, and
  co-introducing to said cells in said animal a vector encoding a VSV antigen,
  thereby enhancing the cytotoxic T-lymphocyte response in said animal to said VSV antigen.

* * * * *

UNITED STATES PATENT AND TRADEMARK OFFICE
CERTIFICATE OF CORRECTION

| | | |
|---|---|---|
| PATENT NO. | : 7,994,146 B2 | Page 1 of 1 |
| APPLICATION NO. | : 12/029080 | |
| DATED | : August 9, 2011 | |
| INVENTOR(S) | : Wilfred Arthur Jefferies et al. | |

It is certified that error appears in the above-identified patent and that said Letters Patent is hereby corrected as shown below:

Column 53, line 61, after "at" second occurrence, delete "nor" and insert therefor -- or --.

Signed and Sealed this
Fourth Day of October, 2011

David J. Kappos
*Director of the United States Patent and Trademark Office*

SEQUENCE LISTING

```
<160> NUMBER OF SEQ ID NOS: 10

<210> SEQ ID NO 1
<211> LENGTH: 40
<212> TYPE: DNA
<213> ORGANISM: Artificial Sequence
<220> FEATURE:
<223> OTHER INFORMATION: vaccinia virus
<220> FEATURE:
<221> NAME/KEY: DNA
<222> LOCATION: (1)..(40)
```

```
<400> SEQUENCE: 1
ctagctcaga ggccttggta gacatatcct ctcatgagct                    40

<210> SEQ ID NO 2
<211> LENGTH: 32
<212> TYPE: DNA
<213> ORGANISM: Artificial Sequence
<220> FEATURE:
<223> OTHER INFORMATION: vaccinia virus
<220> FEATURE:
<221> NAME/KEY: DNA
<222> LOCATION: (1)..(32)

<400> SEQUENCE: 2
catgagagga tatgtctacc aaggcctctg ag                            32

<210> SEQ ID NO 3
<211> LENGTH: 8
<212> TYPE: PRT
<213> ORGANISM: Artificial Sequence
<220> FEATURE:
<223> OTHER INFORMATION: vaccinia virus
<220> FEATURE:
<221> NAME/KEY: Protein
<222> LOCATION: (1)..(8)

<400> SEQUENCE: 3

Arg Gly Tyr Val Tyr Gly Gly Leu
1               5

<210> SEQ ID NO 4
<211> LENGTH: 18
<212> TYPE: DNA
<213> ORGANISM: Artificial Sequence
<220> FEATURE:
<223> OTHER INFORMATION: primer TAP-1
<220> FEATURE:
<221> NAME/KEY: DNA
<222> LOCATION: (1)..(18)

<400> SEQUENCE: 4
gaccggactc tggacagc                                            18

<210> SEQ ID NO 5
<211> LENGTH: 8
<212> TYPE: PRT
<213> ORGANISM: Artificial Sequence
<220> FEATURE:
<223> OTHER INFORMATION: VSV-Np
<220> FEATURE:
<221> NAME/KEY: Protein
<222> LOCATION: (1)..(8)

<400> SEQUENCE: 5

Arg Gly Tyr Val Tyr Gly Gly Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Sendi-Np
<220> FEATURE:
<221> NAME/KEY: protein
<222> LOCATION: (1)..(9)

<400> SEQUENCE: 6

Phe Ala Pro Gly Asn Tyr Pro Ala Leu
```

-continued

```
<210> SEQ ID NO 7
<211> LENGTH: 21
<212> TYPE: DNA
<213> ORGANISM: Artificial Sequence
<220> FEATURE:
<223> OTHER INFORMATION: primer TAP-1
<220> FEATURE:
<221> NAME/KEY: DNA
<222> LOCATION: (1)..(21)

<400> SEQUENCE: 7
gtaaattccg gggcatctcc t                                          21

<210> SEQ ID NO 8
<211> LENGTH: 21
<212> TYPE: DNA
<213> ORGANISM: Artificial Sequence
<220> FEATURE:
<223> OTHER INFORMATION: primer TAP-2
<220> FEATURE:
<221> NAME/KEY: DNA
<222> LOCATION: (1)..(21)

<400> SEQUENCE: 8
aggaagcaga tttcagaact c                                          21

<210> SEQ ID NO 9
<211> LENGTH: 21
<212> TYPE: DNA
<213> ORGANISM: Artificial Sequence
<220> FEATURE:
<223> OTHER INFORMATION: primer TAP-2
<220> FEATURE:
<221> NAME/KEY: DNA
<222> LOCATION: (1)..(21)

<400> SEQUENCE: 9
agtcctgaga gggctcagtg t                                          21

<210> SEQ ID NO 10
<211> LENGTH: 9
<212> TYPE: PRT
<213> ORGANISM: Artificial Sequence
<220> FEATURE:
<223> OTHER INFORMATION: TRP-2 peptide
<220> FEATURE:
<221> NAME/KEY: protein
<222> LOCATION: (1)..(9)

<400> SEQUENCE: 10

Ser Val Tyr Asp Phe Phe Val Trp Leu
1               5
```